United States Patent [19]

Cushman et al.

[11] Patent Number: 5,430,062
[45] Date of Patent: Jul. 4, 1995

[54] STILBENE DERIVATIVES AS ANTICANCER AGENTS

[75] Inventors: Mark S. Cushman, West Layfayette, Ind.; Ernest Hamel, Bethesda, Md.

[73] Assignee: Research Corporation Technologies, Inc., Tucson, Ariz.

[21] Appl. No.: 81,755

[22] Filed: Jun. 23, 1993

Related U.S. Application Data

[63] Continuation-in-part of Ser. No. 887,725, May 21, 1992, abandoned.

[30] Foreign Application Priority Data

May 20, 1993 [WO] WIPO ............... PCT/US93/04807

[51] Int. Cl.⁶ .............. A61K 31/09; A61K 31/135; C07C 43/215; C07C 217/80
[52] U.S. Cl. ..................... 514/646; 514/520; 514/630; 514/651; 514/685; 514/713; 514/716; 514/720; 556/445; 556/446; 564/221; 564/353; 564/354; 564/389; 564/443; 568/39; 568/62; 568/331; 568/465; 568/466
[58] Field of Search ............. 556/445, 446; 564/221, 564/353, 354, 389, 443; 568/39, 62, 331, 465, 466; 514/630, 646, 651, 685, 713, 716, 720

[56] References Cited

U.S. PATENT DOCUMENTS

| | | | |
|---|---|---|---|
| 2,346,049 | 4/1944 | Rohrmann | 568/646 |
| 4,189,610 | 2/1980 | Coleman | 568/646 |
| 4,326,055 | 4/1982 | Loeliger | 542/429 |
| 4,683,087 | 7/1987 | Witiak et al. | 260/396 R |
| 4,940,707 | 7/1990 | Klaus et al. | 514/237.8 |
| 4,940,726 | 7/1990 | Pettit et al. | 514/450 |
| 4,996,237 | 2/1991 | Pettit et al. | 514/720 |
| 5,081,251 | 1/1992 | Bender et al. | 546/350 |

FOREIGN PATENT DOCUMENTS

| | | |
|---|---|---|
| 492111 | 4/1953 | Canada . |
| 0276051 | 7/1988 | European Pat. Off. . |
| 9005952 | 5/1972 | Japan . |

OTHER PUBLICATIONS

Anjaneyulu et al, Chemical Abstracts, vol. 113(1990) 114869X.
Mayer et al, Chemical Abstracts, vol. 106 (1987) 32425r.
Bhandari et al, Chemical Abstracts, vol. 103 (1985) 51168p.
Witiak et al, Chemical Abstracts, vol. 99 (1983) 194554w.
Prakash et al, Chemical Abstracts, vol. 103 (1985) 3717v.
Mervic et al, Chemical Abstracts, vol. 93 (1980) 239078p.
Spencer, Chemical Abstracts, vol. 98 (1983) 53370a.
Giles et al, Chemical Abstracts, vol. 82 (1975) 155944c.
R. M. Letcher et al., Chemical Constituents of the Combretaceae. Part II. Substituted Phenanthrenes and 9,10–Dihydrophenanthrenes and a Substituted Bibenzyl from the Heartwood of Combretum molle, J. Chem. Soc., Perkin I (1972) pp. 206–210.
J. F. Carroll et al., Reactions of Lithium Aluminium Hydride in Hydrocarbon Solvents. Selective Demethylation of Some Substituted Methyl Phenyl Ethers, J. Chem. Soc. Chem, Comm. (1980) pp. 507–508.

(List continued on next page.)

*Primary Examiner*—Richard L. Raymond
*Attorney, Agent, or Firm*—Scully, Scott, Murphy & Presser

[57] ABSTRACT

The present invention relates to stilbene derivatives which possess utility as anti-cancer agents. The compounds can be used to treat cancers which are susceptible to treatment therewith, and can be utilized in a method of treating such cancers. Pharmaceutical compositions containing the compounds are disclosed. Three preferred compounds among those disclosed are (Z)-1-(4-methoxyphenyl)-2-(3,4,5-trimethoxyphenyl)ethene, (Z)-1-(4-methylphenyl)-2-(3,4,5-trimethoxyphenyl)ethene, and 4-methyl-3',4',5'-trimethoxybenzylaniline hydrochloride.

34 Claims, No Drawings

OTHER PUBLICATIONS

R. L. Geahlen et al., Pioeatannol (3,4,3',5'-Tetrahydroxy-Trans-Stilbene) is a Naturally Occurring Protein-Tyrosine Kinase Inhibitor, Biochem. and Biophys. Res. Comm., vol. 165, (1989) pp. 241–245.

M. T. Gill et al., 3,3',5',-Tri-O-Methylpiceatannol and 4, 3',5'-Tri-O-Methylpiceatannol: Improvements Over Piceatannol in Bioactivity, Journ. of Natural Products, vol. 50, No. 1 (1987) pp. 36–40.

M. C. Alley et al., Feasibility of Drug Screening with Panels of Human Tumor Cell Lines Using a Microculture Tetrazolium Assay, Cancer Research, vol. 48 (1988) pp. 589–601.

T. Mosmann, Rapid Colorimetric Assay for Cellular Growth and Survival: Application to Proliferation and Cytotoxicity Assays, Journ. of Immun. Methods, vol. 65 (1983) pp. 55–63.

E. Hammel, et al., Separation of Active Tubulin and Microtubule-Associated Proteins by Ultracentrifugation and Isolation of a Component causing the Formation of Microtubule Bundles, Biochemistry, vol. 23 (1984) pp. 4173–4184.

A. Muzaffar, et al., Antitubulin Effects of Derivatives of 3-Demethylthiocolchicine, Methylthio Ethers of Natural Colchicinoids, and Thioketones Derived from Thiocolchicine. Comparison with Colchicinoids, J. Med. Chem., vol. 33 (1990) pp. 567–571.

L. Jurd, Mannich Base Derivatives of Bioactive Benzyl-1,3-benzodioxo-5-ols, J. Heterocyclic Chem., vol. 22 (1985) pp. 993–995.

L. Jurd, et al., New Types of Insect Chemosterilants. Benzylphenols and Benzyl-1,3-benzodioxole Derivatives as Additives to Housefly Diet, J. Agric. Food Chem, vol. 27, No. 5 (1979) pp. 1007–1016.

P. Nandy, et al., Quantitative Structure-Activity Relationship Analysis of Combretastatins: Class Novel Antimitotic Agents, Pharm. Research, vol. 8, No. 6 (1991) pp. 776–781.

G. R. Pettit et al., Synthesis of Natural (−)-Combretastatin, J. Org. Chem., vol. 50 (1985) pp. 3404–3406.

G. R. Pettit et al., Isolation, Structure, and Synthesis of Combretastatins A-1 and B-1, Potent New Inhibitors of Microtubule Assembly, Derived from Combretum Caffrum, Journ. of Natural Products, vol. 50, No. 1 (1987) pp. 119–131.

G. R. Pettit et al., Isolation and Structure of Combretastatin, Can. J. Chem., vol. 60 (1982) pp. 1374–1376.

G. R. Pettit et al., Isolation, Structure, and Synthesis of Combretastatin A-2, A-3, and B-2, Can. J. Chem., vol. 65 (1987) pp. 2390–2396.

E. Hamel et al., Interactions of Combretastatin, a New Plant-Derived Antimitotic Agent, with Tubulin, Biochemical Pharmacology, vol. 32, No. 24 (1983) pp. 3864–3867.

G. R. Pettit, Isolation and Structure of the Strong Cell Growth and Tubulin Inhibitor Combretastatin A-4, Experientia, vol. 45 (1989) pp. 209–211.

S. E. Drewes et al., Polyhydroxystilbenes from the Heartwood Schotia brachypetala, J. Chem. Soc., Perkin I (1974) pp. 961–962.

A. T. McGown et al., Structural and Biochemical Comparison of the Anti-mitotic Agents Colchicine, Combretastatin A4 and Amphethinile, Anti-Cancer Drug Design, vol. 3 (1989) pp. 249–254.

C. M. Lin et al., Antimitotic Natural Products Combretastatin A-4 and Combretastatin A-2: Studies on the Mechanism of Their Inhibition of the Binding of Colchicine to Tubulin, Biochemistry, vol. 28 (1989) pp. 6984–6991.

A. T. McGown et al., Differential Cytotoxicity of Combretastatins A1 and A4 in Two Daunorbicin-Resistant P388 Cell Lines, Cancer Chemother Pharmacol, vol. 26 (1990) pp. 79–81.

G. R. Pettit et al., Isolation, Structure, Synthesis, and Antimitotic Properties of Combretastatins B-3 and B-4 from Combretum Caffrum, Journ. of Natural Products, vol. 51, No. 3 (1988) pp. 517–527.

C. M. Lin et al., Interactions of Tubulin with Potent Natural and Synthetic Analogs of the Antimitotic Agent Combretastatin: a Structure-Activity Study, Molecular Pharmacology, vol. 34 (1988) pp. 200–208.

G. R. Pettit et al., Antineoplastic Agents, 122. Constituents of Combretum Caffrum, Journ. of Natural Products, vol. 50, No. 3 (1987) pp. 386–391.

M. Cushman et al., Synthesis and Evaluation of Stilbene and Dihydrostilbene Derivatives as Potential Anticancer Agents that Inhibit Tubulin Polymerization, J. Med. Chem. vol. 34 (1991) pp. 2579–2588.

STILBENE DERIVATIVES AS ANTICANCER AGENTS

RELATED APPLICATIONS

The present application is a continuation-in-part of U.S. patent application having Ser. No. 887,725 filed on May 21, 1992, now abandoned.

The present invention relates to the use of stilbene derivatives and stilbene-like derivatives as anti-cancer agents, pharmaceutical compositions of these compounds and to novel compounds thereof.

Tropical and subtropical shrubs and trees of the Combretacae family represent a potentially unexplored source of new compounds which have useful biological properties. For example, the genus Combretrum is known in the medical practices of Africa and India for treating various illness such as leprosy and cancer. However, only a few species like *Combretrum micranthum* and *Combretrum zeyheri* have received any substantial scientific work.

In recent years through the work of the U.S. National Cancer Institute, the African tree *Combretrum caffrum* has been found to contain certain agents which were determined to be highly cytotoxic. These agents isolated from the African tree *Combretrum caffrum* are referred to as combretastatins.

U.S. Pat. No. 4,996,237 to Pettit et al. relates to the isolation and syntheses of a neoplastic substance having the structural formula:

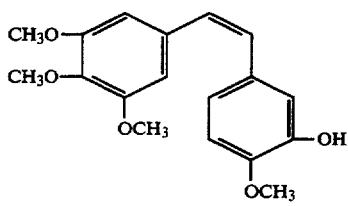

The natural product having such a formula has referred to as "Combretastatin A-4". It has been. observed that this cis-stilbene exhibits strong cytotoxic activity by inhibiting tubulin polymerization.

European Patent Application No. 276,051 to Pettit et al. relates to the isolation, structural elucidation and synthesis of new antineoplastic compounds having tile structural formulas:

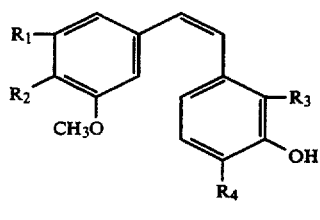

(A)

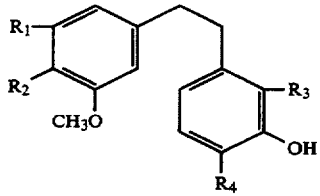

(B)

wherein $R_1$ is OH or $OCH_3$; $R_2$ is H or $OCH_3$; or $R_1$ and $R_2$ taken together is $-OCH_2O-$; $R_3$ is H or OH; and $R_4$ is OH or $OCH_3$ and wherein the configuration of the double bond in formula (A) is cis. These compounds were tested to determine their murine 388 lymphocytic leukemia inhibition.

Despite their potential use as anti-cancer agents, these combretastatin derivatives are limited by their relatively low solubility in water and saline. This has led to an increased interest in the syntheses and evaluation of polymethoxylated stilbenes and dihydrostilbenes as potential anti-cancer agents.

Thus, the present invention is directed to the development of new anti-cancer agents based on these natural products as structural leads. More specifically, the present invention is directed to compounds having two aryl or heteroaryl groups or combinations thereof separated by a bridging unit of at least 1 or 2 atoms, such as $C=O$, alkylene, alkyleneamino, carboxamido (or derivatives thereof), or alkene (e.g., ethenes), in which the aryl or heteroaryl groups are substituted by at least two alkoxy groups. The present invention is also directed to pharmaceutical compositions thereof and their use as anti-cancer agents. In an embodiment, the present invention relates to a series of cis-, trans- and dihydro-stilbenes and N-arylbenzylamines, and aryl benzoamides and the compounds thereof as anti-cancer agents to be administered to animals.

The present invention is directed to the use of compounds having the structural formula (I):

$$(R') \ Ar-X-Ar_1(R'') \qquad (I)$$

and pharmaceutically acceptable salts thereof wherein Ar and $Ar_1$ are independently aryl or heteroaryl; and Ar may be mono, di, tri, or tetrasubstituted with R' and $Ar_1$ may be mono, di, tri, or tetrasubstituted with R";

X is $$-\overset{\overset{O}{\|}}{C}-, \ -NH-CH_2-, \ -CH_2NH-,$$

$$-NH-\overset{\overset{O}{\|}}{C}-, \ -\overset{\overset{O}{\|}}{C}-NH-,$$

$-(Y_2)(Y_3)C-C(Z_2)(Z_3)-$ or cis or trans ethylene radical of the formula $-(Y_1)C=C(Z_1)$, $CH_2$ or CHOH;

$Y_1$, $Y_2$, $Y_3$, $Z_1$, $Z_2$ and $Z_3$ are independently hydrogen, lower alkyl, lower alkoxy, carboxy, lower carbalkoxy, $COONR_{13}R_{14}$, cyano, or $COOQNR_{15}R_{16}$;

$R_{13}$, $R_{14}$, $R_{15}$ and $R_{16}$ are independently hydrogen or lower alkyl;

Q is lower alkylene;

each R' may be the same or different and consists of $R_1$, $R_2$, $R_3$ and $R_4$, and each R" may be the same or different and consists of $R_5$, $R_6$, $R_7$ and $R_8$; wherein each $R_1$, $R_2$, $R_3$, $R_4$, $R_5$, $R_6$, $R_7$ and $R_8$ are independently hydrogen, lower alkyl, aryl, halo, amino, lower alkylamino, diloweralkylamino, lower alkoxy, lower aralkyl, arylkoxy, lower aralkoxy, cyano, aryloxy, mercapto, lower alkylthio, amino lower alkyl, carboxy, carbolower alkoxy, $CONHR_9$, $NHCO(R_9)$, lower alkanoyl, nitro, $CF_3$, lower alkyl carbonyloxy, amino lower alkoxy, lower alkyl amino lower alkoxy, dilower alkylamino lower alkoxy amino lower alkylene oxycarbonyl, lower alkylamino loweralkyleneoxycarbonyl, dilower alkylamino lower alkenene oxy carbonyl, OSi(R$_{10}$R$_{11}$R$_{12}$) or Si(R$_{17}$) (R$_{18}$) (R$_{19}$) and at least two or R$_1$, R$_2$, R$_3$, R$_4$, R$_5$, R$_6$, R$_7$ and R$_8$ is loweralkoxy;

R$_9$ is hydrogen or lower alkyl;

R$_{10}$, R$_{11}$, R$_{17}$, R$_{18}$, and R$_{19}$ are independently lower alkyl; and R$_{12}$ is lower alkyl or lower alkoxy;

and the pharmaceutical composition containing these compounds as the active ingredients thereof. Also, the invention relates to novel compounds encompassed by Formula I.

As described hereinabove, the present invention encompasses compounds of the formula

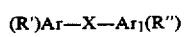

and pharmaceutically acceptable salts thereof wherein R', R", Ar, Ar$_1$ and X are as defined hereinabove. As defined herein, the Ar group is substituted by R$_1$, R$_2$, R$_3$ and R$_4$ while Ar$_1$ is substituted by R$_5$, R$_6$, R$_7$ and R$_8$. In other words, Ar and Ar$_1$ can independently be unsubstituted, monosubstituted, disubstituted, trisubstituted or tetrasubstituted; however the compound of Formula I must contain at least two alkoxy groups and preferably at least three alkoxy groups. The alkoxy groups may be substituted as only Ar or Ar$_1$ or may be substituted as both Ar and Ar$_1$. In an especially preferred embodiment, at least two of the alkoxy groups are substituted on Ar; and in a most preferred embodiment, at least three of the alkoxy groups are substituted on Ar$_1$.

As defined herein, the present invention contemplates employing the compounds in Formula I in compositions to be administered in an effective dosage amount to animals as potential new anti-cancer agents.

The term "aryl", when used alone or in combination, refers to an aromatic group which contains from 6 up to 18 ring carbon atoms and up to a total of 25 carbon atoms and includes the polynuclear aromatics. These aryl groups may be monocyclic, bicyclic, tricyclic or polycyclic and are fused rings. Polynuclear aromatic compound is meant to encompass bicyclic, tricyclic fused aromatic ring systems containing from 10–18 ring carbon atoms and up to a total of 25 carbon atoms. The aryl group includes phenyl, and the polynuclear aromatics e.g., naphthyl, anthracenyl, phenanthrenyl, azulenyl and the like. The preferred aryl group is naphthyl and especially phenyl.

The term "heteroaryl", when used alone or in combination, is a nitrogen, sulfur or oxygen containing heteroaromatic group. The ring heteroatoms are either nitrogen, sulfur or oxygen. The heteroaryl groups may be monocyclic, bicyclic, or polycyclic; but if it contains more than 1 ring, the rings are fused. Furthermore, the heteroaryl groups are planar. The heteroaryl groups contain 1–4 ring heteroatoms and from 5–14 ring atoms. The heteroaryl group contains from 1–13 and preferably 3–13 ring carbon atoms and up to a total of 18 carbon atoms. The heteroaryl includes such groups as thienyl, benzothienyl, naphthathienyl, thianthrenyl, furyl, benzofuryl, pyrrolyl, imidazolyl, pyrazolyl, pyridyl, pyrazinyl, pyrimidinyl, pyridazinyl, indolyl, indazolyl, purinyl, quinolyl, isoquinolyl, thiazolyl, isothiazolyl, oxazolyl, isooxazolyl, benzoxazolyl; benzoxathiazolyl, benzothiazolyl and benzoisothiazolyl, and the like, and the N-oxides of the nitrogen containing heteroaryl, such as the N-oxides of pyridyl, pyrazinyl, pyrimidinyl and the like. The preferred heteroaryl groups contain up to 10 ring atoms and 1 or 2 ring heteroatoms and up to a total of 15 carbon atoms. Preferably, the heterocyclic group contains at least 1 ring nitrogen atom. Preferred heteroaryl groups include pyridyl, pyrimidinyl, pyrazinyl, pyridazinyl, thienyl, furyl, oxazolyl, thiazolyl, benzooxazolyl, imidazolyl, indolyl, quinolyl, isoquinolyl, thiazolyl, benzothiazolyl, benzoxazolyl and pyrrolyl. The especially preferred heteroaryl groups include thienyl, pyrazinyl, pyrimidinyl, pyridyl, thiazolyl, and the N-oxide of pyridyl. The most preferred heteroaryl group is pyridyl.

The alkyl groups when used alone or in combination with other groups, are lower alkyl contain from 1 to 6 carbon atoms and may be straight chained or branched. These groups include methyl, ethyl, propyl, isopropyl, butyl, isobutyl, tertiary butyl, pentyl, hexyl, and the like.

The preferred alkyl groups contain 1–4 carbon atoms; more preferred alkyl groups contain 1–3 carbon atoms. The most preferred alkyl group is methyl. Alkylene as used herein refers to a bridging alkyl group of the formula C$_n$H$_{2n}$. Examples include CH$_2$, —CH$_2$CH$_2$—, —CH$_2$CH$_2$CH$_2$— and the like.

As used herein, the term "lower alkoxy" refers to —O— alkyl groups, wherein alkyl is as defined hereinabove. The alkoxy group is bonded to the main chain, aryl or heteroaryl group through the oxygen bridge. The alkoxy group may be straight chained or branched; although the straight-chain is preferred. Examples include methoxy, ethyloxy, propoxy, butyloxy, t-butyloxy, i-propoxy, and the like. Preferred alkoxy groups contain 1–4 carbon atoms, especially preferred alkoxy groups contain 1–3 carbon atoms. The most preferred alkoxy group is methoxy.

"Lower carbalkoxy" is a group of the formula

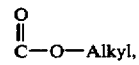

wherein the acyl group is bonded to the main chain and alkyl is as defined hereinabove. Examples include COOMe, COOEt, COOPr, and the like. The preferred group is COOMe.

"Halo" includes fluoro, bromo, chloro or iodo.

"Lower Alkylamino" refers to a group wherein one alkyl group is bonded to an amino nitrogen, i.e., NH(alkyl). The NH is the bridge connecting the alkyl group to the aryl or heteroaryl. Examples include NHMe, NHEt, NHPr, and the like.

Similarly, "lower diloweralkylamino" refers to a group wherein two alkyl groups, which may be the same or different are bonded to an amino nitrogen and the dialkylamino group is bonded to the aryl or heteroaryl through an NH bridge. It is preferred that both alkyl groups are the same. Examples include NMe$_2$, N(Me)(Et), NEt$_2$, and the like, the most preferred is NMe$_2$.

As used herein, "lower arylalkyl", when used alone or in combination, refers to an aryl-alkylene bond, i.e., the aryl alkyl group is bonded as a substituent through the alkylene moiety. Examples include benzyl, phenethyl, phenpropyl, phenisopropyl, phenbutyl, and the like, diphenyl methyl, 1,2-diphenyl methyl, and the like.

The arylalkoxy refers to an O-aryl group wherein the arylalkoxy group is attached as a substituent through an oxygen bridge. Similarly, aralkoxy refers to an O-arylalkyl group wherein the aralkoxy is attached as a substituent through the oxygen atom.

"Alkylthio" refers to an S-alkyl group, wherein the alkylthio is attached as a substituent through the S atom.

The term amino lower alkyl refers to a group of the formula alkylene-$NH_2$, wherein this group is attached as a substituent through the alkylene moiety. Examples include —$CH_2NH_2$, $CH_2CH_2NH_2$ and the like.

As used herein, lower alkenoyl refers to a lower alkyl group, as defined, wherein one of the carbon atoms is replaced by a carbonyl group. It also includes formyl. Examples include acetyl, propanoyl, butanoyl, and the like.

The term "lower alkyl carbonyloxy" refers to a group of the formula O—C-Alkyl, wherein the alkyl is defined herein. In other words, the lower alkyloxycarbonyl is bonded as a substituent through the oxygen atom. Examples include

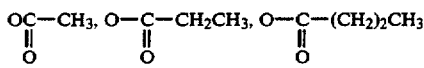

and the like, with the preferred group being OAc.

As used herein the term "amino lower alkoxy" refers to the group —O-Alkylene-$NH_2$—, wherein alkylene is defined hereinabove. This group is attached as a substituent through its oxygen atom. Similarly, the term lower alkylamino loweralkoxy refers to an amino lower alkoxy group, wherein one of the amino hydrogens is replaced by a lower alkyl group. Furthermore, a dilower-alkyl amino lower alkoxy refers to an amino lower alkoxy group wherein both amino hydrogens are replaced by an alkyl group. The alkyl groups in the latter term may be the same or different but it is preferred that the alkyl groups are the same. Examples of the first term include O—$(CH_2)_2NH_2$, $OCH_2NH_2$, and the like; examples of the second term include $OCH_2CH_2NHMe$, $OCH_2CH_2NHEt$, $OCH_2NHMe$, $OCH_2NHEt$, and the like, finally, examples of the latter term include $OCH_2CH_2NMe_2$, $OCH_2CH_2NEt_2$, and the like.

The term "amino lower alkylene oxy carbonyl" as used herein, refers to the group

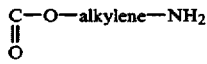

wherein alkylene is as defined herein. Similarly, "lower alkyl amino lower alkylene carbonyl" refers to an amino lower alkylene oxycarbonyl wherein one of the amino hydrogens is replaced by an alkyl group as defined herein. Furthermore, diloweralkyl amino lower alkylene oxycarbonyl refers to an amino loweralkylene oxycarbonyl wherein both amino hydrogens are replaced by a lower alkyl, and the lower alkyls may be the same or different. Examples of the first group include —COO—$(CH_2)_2NH_2$, —$COOCH_2NH_2$ and the like; examples of the second group include $COOCH_2NHMe$, $COOCH_2NHEt$, $COO(CH_2)_2NHMe$, $COO(CH_2)_2NHEt$ and the like, while examples of the latter group include $COOCH_2NMe_2$, $COOCH_2NEt_2$, $COO(CH_2)_2NEt_2$, $COO(CH_2)_2NMe_2$ and the like.

The preferred value of X as used herein is

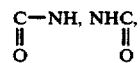

$CH_2NH_2$, $NH_2CH$, cis or trans-$(Y_1)C$=$C(Z_1)$ and $(Y_2)(Y_3)C$—C—$(Z_2)$ $(Z_3)$, wherein $Y_1$, $Y_2$, $Y_3$, $Z_1$, $Z_2$ and $Z_3$ are defined hereinabove. A more preferred value of X is $(Y_1)C$=$C(Z_1)$,

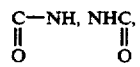

$CH_2NH$ or $CH_2NH$. Especially preferred X is

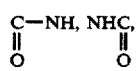

$CH_2NH$, $NHCH_2$ and cis $(Y_1)C$=$C(Z_1)$. A more especially preferred value of X is

$CH_2NH$ and cis $(Y_1)C$=$C(Z_1)$, and the most preferred value of X is cis $(Y_1)C$=$C(Z_1)$ and $CH_2NH$.

The preferred values of $Y_1$ and $Z_1$ in $(Y_1)C$=$C(Z_1)$ in either the trans or cis form are independently hydrogen, carboxy, carboloweralkoxy, $COONHR_{13}$, cyano or $COOQNR_{15}R_{16}$. It is preferred that $Y_1$ is hydrogen, carboxy, carboloweralkoxy, $COONHR_{13}$, or $COOQNR_{15}R_{16}$, and that $Z_1$ is hydrogen or COOH. More especially, it is preferred that Y is COOH, COOMe, COONHMe, COONHEt, COO$(CH_2)_2NEt_2$, $COOCH_2NMe_2$ or H. The most preferred value of $Y_1$ and $Z_1$ is hydrogen.

The most preferred values of $Z_2$, $Z_3$, $Y_2$ and $Y_3$ are independently hydrogen, cyano or carboloweralkoxy (e.g. COOMe). It is most preferred that one of $Y_2$, $Z_2$, $Y_3$ or $Z_3$ is hydrogen and the other is hydrogen, cyano or carboloweralkoxy. It is most preferred that $Y_2$ and $Z_2$ are hydrogen, $Y_3$ is cyano or hydrogen and $Z_3$ is hydrogen, cyano or lower carbalkoxy (e.g., COOMe). It is most especially preferred that $Z_2$, $Z_3$ $Y_2$ and $Y_3$ are all hydrogen.

A preferred value of $R_{13}$ is hydrogen; the preferred values of $R_{14}$, $R_{15}$ and $R_{16}$ are methyl or ethyl. It is preferred that $R_{15}$ and $R_{16}$ are the same and that both are methyl and ethyl.

The preferred value of Q is ethylene.

The preferred values of $R_1$, $R_2$, $R_3$, $R_4$, $R_5$, $R_6$, $R_7$ and $R_8$ are independently hydrogen, $C_1$–$C_4$ lower alkoxy, benzyloxy, acetyloxy, t-butyldimethoxy siloxy, halogen, $C_{1-4}$ lower alkyl, t-butyl dimethyl silyloxy, trimethyl silyl, amino, 3–6 dimethylamino lower alkoxy halo (e.g., chloro, bromo), nitro, $NMe_2$, $C_{1-4}$ alkylthio, $C_{1-4}$ lower alkyl, O$(CH_2)_2NMe_2$, O$(CH_2)_2NEt_2$. It is more preferred that $R_1$, $R_2$, $R_3$, $R_4$, $R_5$, $R_6$, $R_7$ and $R_8$ are independently hydrogen, methoxy, chloro, bromo, nitro, OSi(t-Bu) $(CH_3)_2$, $NMe_2$, OAc, OEt, OPr, SMe, Me, Et, iPr, t-Bu, $NH_2$, $NHCOCH_3$, O$(CH_2)_2NMe_2$, and O$(CH_2)_2NEt_2$.

In the most preferred embodiment, the compounds of Formula I have the formula

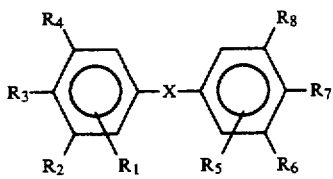

In Formula Ia, it is preferred that at least one of $R_2$, $R_3$ and $R_4$ is lower alkoxy, especially methoxy, it is more preferred that at least two of $R_2$, $R_3$ and $R_4$ is lower alkoxy; especially methoxy and it is most especially preferred that $R_2$, $R_3$ and $R_4$ are lower alkoxy (e.g. methoxy). Further, it is preferred that $R_1$ is hydrogen.

Further, it is preferred that at least one of $R_6$, $R_7$ and $R_8$ is other than hydrogen, and most preferably it is preferred that $R_6$ and $R_8$ are hydrogen. The most preferred values of $R_7$ is hydrogen, halo (e.g., chloro, bromo or iodo), lower alkoxy (e.g., OMe, OEt, OPr), diloweralkylamino (e.g., NMe$_2$), loweralkylthio (e.g., SMe), lower alkyl, or CF$_3$. In addition, it is preferred that $R_5$ is hydrogen; however, if it substituted, it is preferred that $R_5$ may be the 2-substituent, and the preferred $R_5$ value at the 2-position is hydrogen or halo (e.g., Cl). It is most preferred that $R_7$ has the preferred embodiment described herein that $R_6$ and $R_8$ are H and that $R_5$ is hydrogen or 2-halo (e.g., Cl).

An even more preferred embodiment of the present invention has the formula:

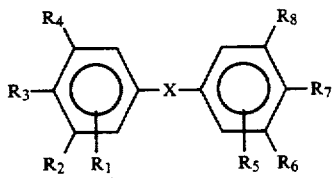

or pharmaceutically acceptable salts thereof wherein $R_1$, $R_2$, $R_3$, $R_4$, $R_5$, $R_6$, $R_7$ or $R_8$ are as defined hereinabove and X is defined as NHCH$_2$ and more preferably CH$_2$NH. In this embodiment, the pharmaceutically acceptable salts are also preferred, i.e, wherein the nitrogen in the bridging group forms a quaternary ammonium ion:

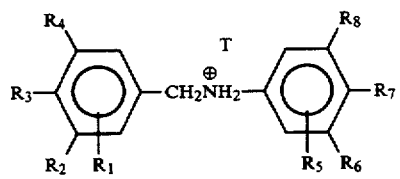

or

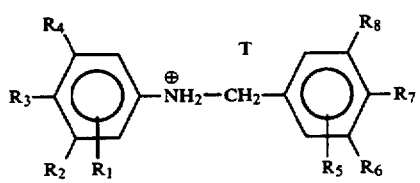

wherein T is the counterion. The counterions include such groups as the halides (I, Cl, Br or F), sulfates, nitrates, benzenesulfonates, toluene sulfonates, acetates, propionates, formates, malates, tartrates, and the like. The most preferred counterions are the halides, especially bromides and more especially chlorides.

In the compounds of the above formulae, it is preferred that $R_5$, $R_6$ and $R_8$ are hydrogen and that $R_7$ is other than hydrogen.

An even more preferred embodiment of the compounds of Formulae Ib, Ib$_1$, and Ib$_2$ is

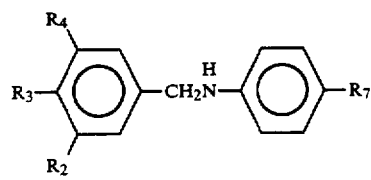

or pharmaceutically acceptable salts thereof wherein $R_2$, $R_3$, $R_4$ and $R_7$ are as defined herein. It is preferred that $R_2$, $R_3$ and $R_4$ are lower alkoxy and $R_7$ is lower alkoxy, lower alkyl, halo, thiolower alkyl, trifluoromethyl, lower carbalkoxy, carboxy, cyano, lower alkanoyl, formyl, nitro or sulfonic acid (SO$_3$H). It is most preferred that $R_2$, $R_3$ and $R_4$ are lower alkoxy, and that $R_7$ is other than hydrogen, especially lower alkoxy, lower alkyl, halo, thio lower alkyl or CF$_3$. It is most preferred that the alkyl group alone, or in combination, contains 1-2 carbons; and that it is especially most preferred that the alkyl group contains 1 carbon atom. Preferred $R_7$ is methyl, ethyl, methoxy, ethoxy, CF$_3$ or thiomethyl. The preferred halo is chloro, bromo and especially iodo.

Especially preferred compounds of the above formulae Ib, Ib$_2$, Ib$_3$, is Ib$_4$

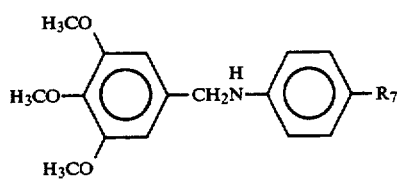

or pharmaceutically acceptable salts thereof wherein $R_7$ is lower alkyl, halo, thioalkyl, CF$_3$ and lower alkoxy as defined hereinabove.

However in all of the above embodiments, the pharmaceutically acceptable salts are the most preferred embodiment, especially since the quaternary cations of Formulae Ib, Ib$_2$, Ib$_3$ and Ib$_4$ are soluble in aqueous solutions.

The most preferred quaternary salt is 4-methyl-3',4',5'-trimethoxybenzylaniline hydrochloride.

It is to be noted that all permutations and combinations of the variables $R_1$–$R_{19}$, Q, $X_1$, $X_2$, $X_3$, $Y_1$, $Y_2$, $Y_3$, T, $Z_1$, $Z_2$ and $Z_3$ are contemplated by the present invention. Further, it is to be noted that, in addition, Markush groupings containing less than all of the elements described hereinabove as well as the various permutations and combinations thereof are also contemplated by the present invention.

Preferred compounds encompassed by Formula I include:

(Z)-1-(4-methoxyphenyl)-2-(3,4,5-trimethoxyphenyl)ethene;
(Z)-1-(3-methoxyphenyl)-2-(3,4,5-trimethoxyphenyl)ethene;

(Z)-1-(2-chloro-4-methoxyphenyl)-2-(2,3,4-trimethoxyphenyl)ethene;

(Z)-1-phenyl-2-(3,4,5-trimethoxyphenyl)ethene;

(Z)-1-(4-chlorophenyl)-2-(3,4,5-trimethyloxyphenyl)ethene;

(Z)-1-(4-bromophenyl)-2-(3,4,5-trimethoxyphenyl)ethene;

(Z)-1-[4-N,N-dimethylamino)phenyl]-2-(3,4,5-trimethoxyphenyl)ethene;

(E)-1-[4-(N,N-dimethylamino)phenyl]-2-(3,4,5-trimethoxyphenyl)ethene;

1-(4-methoxyphenyl)-2-(3,4,5-trimethoxyphenyl)ethene;

1-[4-(dimethylamino)phenyl]-2-(3,4,5-trimethoxyphenyl)ethene;

3,4,5-trimethoxy-N-(4-methoxyphenyl)benzylamine; and (Z)-1-(4-methylphenyl)-2-(3,4,5-trimethoxyphenyl)ethene.

A most preferred compound of Formula I is (Z)-1-(4-methoxyphenyl)-2-(3,4,5-trimethoxyphenyl)ethene.

The compounds of the present invention can be prepared by art-recognized techniques. Although the examples described hereinbelow may be specific, the syntheses are general. For example, in the Wittig reaction described hereinbelow and depicted in Scheme 1, a heteroaryl-arorylmethylene-triphenylphosphonium can in reaction with a heteroaryl or aryl aldehyde under Wittig-like conditions

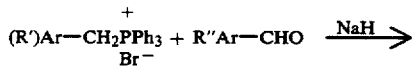

to form the corresponding

Further hydrogenation of the stilbene gives the corresponding dihydro stilbenes. In the scheme, Ar, Ar$_1$, R' and R" are defined herein.

Similarly, the formation of the compound of Formula Ia wherein X is CONH or CH$_2$NH depicted in Scheme 6 is also general and is applicable to compounds of Formula Ia when Ar and Ar$_1$ are other than phenyl. For example, the reaction in Scheme 6 is general for the reaction between an aryl or heteroaryl acid chloride and an aryl or heteroaryl amino reacted under amide forming condition followed by reduction with LiAlH$_p$, as shown hereinbelow:

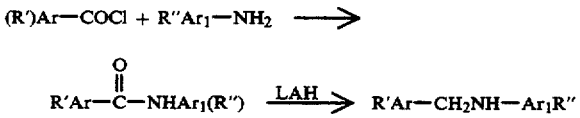

Similarly, the reactions in Scheme II-V + VII-XIII are general and can be depicted to encompass the syntheses of compounds when Ar and Ar$_1$ are as defined herein. Therefore, the syntheses described in those enumerated schemes are to read in that light.

Chemistry

Wittig reaction of phosphonium bromide compounds 3a-b with aryl aldehyde compounds 4a-4n in THF in the presence of sodium hydride followed by preparative thin layer chromatographic separation gave the corresponding cis stilbene compounds 5a-n and trans stilbene compounds 6a-6n (Reaction Scheme I; see Table I). In general all these reactions gave the cis isomers as major components, and, except in a few cases, trans isomers were also isolated as minor products in yields of over 10%. However, in the case of aryl aldehydes with a substituent at the 2-position (compounds 4c, 4d and 4e) and pyridine-2-carboxaldehyde, cis isomers were obtained in very high yields, and the trans isomers were obtained in poor yields. With 2,3,4-trimethoxybenzaldehyde compound (4d) an isolable amount of the trans stilbene was not obtained. Trans-stilbene compounds 6q-6y were prepared by the Wittig-Horner reaction of phosphonate ester compounds 7a-c with the aryl aldehydes 4d and 4o-4t in DMF using sodium methoxide as the base (Scheme II). Under these reaction conditions, trans isomers were obtained exclusively. 4'Hydroxystilbene compounds 5o and 6o were prepared from the corresponding O-silyloxylated stilbenes 5m and 6m by the action of tetra-n-butylammonium fluoride in THF. In another set of reactions, the 4'-acetoxystilbenes 5p and 6p were prepared by acetylation of 4'-hydroxystilbenes 5o and 6o (Scheme III). Cis or trans geometries of most of these compounds were confirmed by their characteristic coupling constants for the olefinic protons of about 12 Hz for cis and 16.0–16.5 Hz for trans isomers. The two olefinic protons of compounds 5d, 5m, 6g and 6p gave singlets and those of compounds 5o and 6b gave multiplets, and the geometries of these compounds were assigned relative to their isomers, which gave distinct doublets with characteristic coupling constants. Catalytic hydrogenation of E-stilbene compounds 6 at about 40 psi in the presence of 10% palladium on charcoal gave dihydrostilbene compounds 8 (Scheme IV). Lithium aluminum hydride reduction of (E)-4'-nitro-3,4,5-trimethoxystilbene (6l) provided (E)-4'-amino-3,4,5-trimethoxystilbene (6z). Catalytic hydrogenation of compound 6l in EtOAc at 40 psi in the presence of 10% palladium on charcoal gave 4'-amino-3,4,5-trimethoxydihydrostilbene (8z), which on subsequent reaction with acetyl chloride gave the acetamido compound 8m (Scheme V). Scheme VI describes the general method adopted for the preparation of amide compounds 11a–11f and their subsequent reduction to substituted benzylamines 12a–12f.

4-Benzyloxy-3,5-dimethoxybenzaldehyde (13j) was prepared by the reaction of syringaldehyde with benzyl chloride in the presence of K$_2$CO$_3$ in boiling acetone. Similarly, reaction of t-butyldimethylsilyl chloride with syringaldehyde in DMF in the presence of N,N-diisopropylethylamine gave 4-(t-butyldimethylsilyl)-oxy-3,5-dimethoxybenzaldehyde (13k) (Scheme VII). Wittig reaction of phosphonium bromides 14a-b with benzaldehydes 13a-k in THF in the presence of sodium hydride followed by preparative thin-layer chromatographic separation of the crude products afforded the cis stilbenes 15a-k and trans stilbenex 16a-k (Scheme VIII). Reaction of compounds 15k and 16k with tetra-n-butylammonium fluoride and in situ acetylation of the phenols with acetic anhydride gave the acetoxy compounds 15l and 16l (Scheme IX). The cis and trans geometries of the stilbenes were assigned by the characteristic $^1$H NMR coupling constants of the olefinic protons. Catalytic hydrogenation of stilbenes 15 and 16 at about 40 psi in the presence of 10% palladium on charcoal gave the dihydrostilbenes 17a–e (Scheme XIII). The amino ethers 17f-g were prepared by the reaction of 1-(4-hydroxyphenyl)-2-(3,4,5-trimethoxyphenyl)e- thane (18) with dialkylaminoethyl chlorides 19a-b in refluxing acetone in the presence of K₂CO₃ (Scheme X). Compounds 17h and 17i were prepared by the alkylation of 3,4,5-trimethoxyphenyl-acetonitrile (20a) and 4-methoxyphenylacetonitrile (20b) with 4-methoxybenzyl bromide (21a) and 3,4,5-trimethoxybenzyl bromide (21b), respectively, using LDA as the base (Scheme XI). Similarly, alkylation of methyl 4-methoxyphenylacetate (20b) with 3,4,5-trimethoxybenzyl bromide 21b gave product 17j.

Several derivatives containing acidic and basic functional groups, including the previously mentioned amines 17f-g, were prepared in an attempt to make compounds that were more soluble in water and could therefore be formulated more easily. Base catalyzed condensation of phenylacetic acids 22a-b with aryl aldehydes 13l-n in the presence of triethylamine gave the carboxylic acids 23a-c (Scheme XII). Esterification of compounds 23a-b with methanol using a catalytic amount of H₂SO₄ gave products 24a-b (Scheme XII). Reaction of thionyl chloride with the carboxylic acids 23a-b in refluxing benzene gave the corresponding acid chlorides, which on subsequent reaction with appropriate amines and alkylaminoalcohol gave compounds 24c-f (Scheme XII).

The effect of shortening the distance between the two aromatic rings was investigated by preparing compound 29, having a methylene unit separating the rings. Friedel-Crafts acylation of anisole with 3,4,5-trimethoxybenzoyl chloride gave 3,4,4',5-tetraethoxybenzophenone (27, Scheme XIII). Sodium borohydride reduction of compound 27 in methanol afforded 4-methoxy-phenyl-(3,4,5-trimethoxyphenyl)methanol (28), which on catalytic hydrogenolysis in the presence of 10% palladium on charcoal gave 4-methoxyphenyl-(3,4,5-trimethoxyphenyl)methane (29) (Scheme XIII).

Several conformationally rigid analogues of the compound 5a were synthesized in an attempt to gain evidence concerning the biologically active conformation of this substance. Different conformations are available to 5a through rotation about the two bonds connecting the aromatic rings to the alkene unit. This question was investigated by forming a covalent bond between the two aromatic rings of several stilbenes, resulting in the phenanthrenes 32a-d (Scheme XIV). Photocyclization of the cis-trans mixtures of stilbenes 30a-c and 31a-c in the presence of iodine afforded the desired phenanthrenes 32a-d. Conformationally restricted analogues of the active dihydrostilbene 8a were also prepared. Synthesis of one such compound based on the indane system is detailed in Scheme XV. Hydrolysis of the methyl ester 17j under basic conditions gave the acid 33. The indanone 34 was then prepared by an intra-molecular Friedel-Crafts acylation reaction using the acid chloride derived from 33. The desired indane 35 was obtained by treatment of 34 with hydrogen in the presence of palladium on charcoal. Several conformationally restricted congeners of the dihydrostilbene 8a were prepared based on the 1-benzylisoquinoline ring system. In these compounds, the rotation about the trimethoxybenzene ring and the attached carbon of the stilbene moiety is restricted. Compounds 36, 37, 38, and 41 (Scheme XVI) are known compounds that resynthesized by a modification of the route originally published by Kupchan et al. Treatment of 36 with DDQ gave derivative 39, which was methylated using methyl iodine to afford compound 40.

A conformationally rigid tetrahydroprotoberberine analogue of 8a was also synthesized as shown in Scheme (XVII). Acylation of the primary amino group of 42 with acetyl chloride gave the acetamide derivative 43. A Bischler-Napieralski reaction involving the treatment of 43 with phosphorus oxychloride afforded the dihydroisoquinoline 44. Reaction of 44 with the acid chloride 45 yielded 46, which underwent the enamide photocyclization reaction to give the substituted protoberberine 47. Reduction of 47 by sequential treatment with lithium aluminum hydride and sodium borohydride yielded the desired tetrahydroprotoberberine 48. In this compound, each of the three C—C bonds connecting the two aromatic rings of the 1,2-diphenylmethane moiety is conformationally restricted.

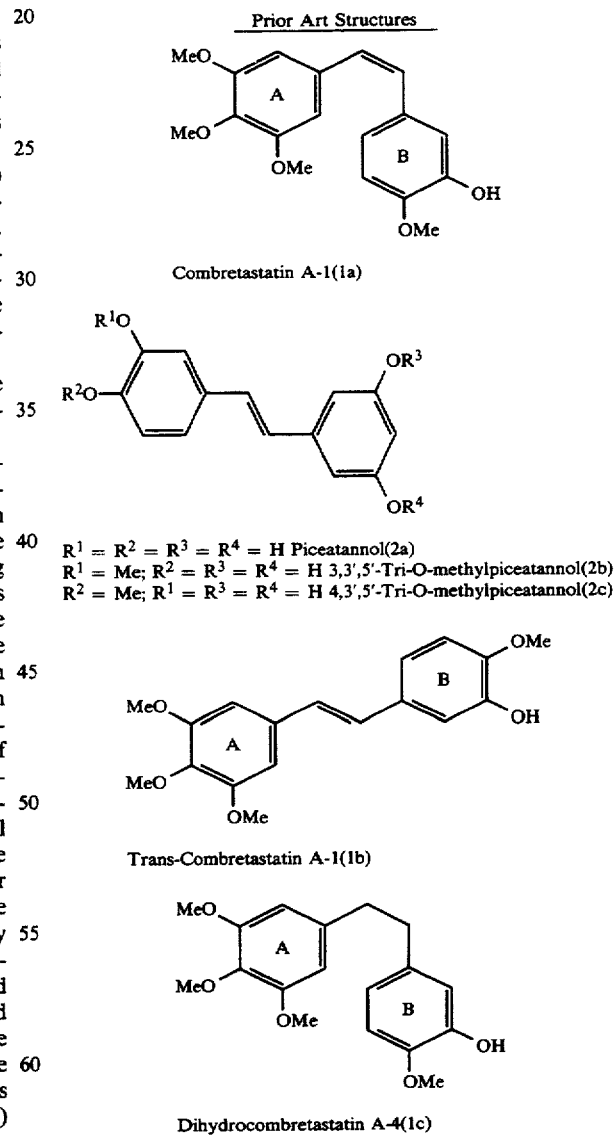

Prior Art Structures

Combretastatin A-1(1a)

$R^1 = R^2 = R^3 = R^4 = H$ Piceatannol(2a)
$R^1 = Me; R^2 = R^3 = R^4 = H$ 3,3',5'-Tri-O-methylpiceatannol(2b)
$R^2 = Me; R^1 = R^3 = R^4 = H$ 4,3',5'-Tri-O-methylpiceatannol(2c)

Trans-Combretastatin A-1(1b)

Dihydrocombretastatin A-4(1c)

Schemes

Scheme I

-continued
Schemes
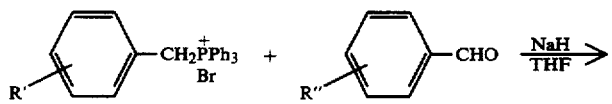
| | 3a-b | | 4a-n | |
|---|---|---|---|---|
| | R' | R'' | | R'' |
| 3a: | 3,4,5-(OMe)₃ | 4a: 4-OMe | 4g: | 4-Cl |
| 3b: | 4-OMe | 4b: 3-OMe | 4h: | 4-Br |
| | | 4c: 2-OMe | 4l: | 4-NO₂ |
| | | 4d: 2,3,4-(OMe)₃ | 4m: | 4-OSi(t-Bu)Me₂ |
| | | 4e: 2-Cl-4-OMe | 4n: | 3-OMe |
| | | 4f: H | | |
4i: R''-C₆H₄ = 4-pyridyl
4j: R''-C₆H₄ = 3-pyridyl
4k: R''-C₆H₄ = 2-pyridyl
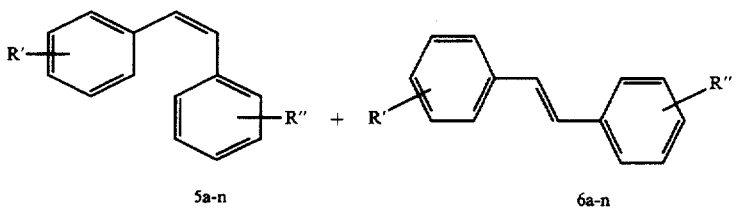
5a-n        6a-n
Scheme II
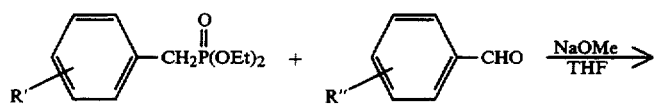
| | 7a-c | | 4d, 4o-t |
|---|---|---|---|
| | R' | | R'' |
| 7a: | H | 4o: | 3,4-(OMe)₂ |
| 7b: | 3,4-(OMe)₂ | 4p: | 3,5-(OMe)₂ |
| 7c: | 3,4,5-(OMe)₃ | 4q: | 3,4,5-(OMe)₃ |
| | | 4r: | 2,4,5-(OMe)₃ |
| | | 4s: | 2,4,6-(OMe)₃ |
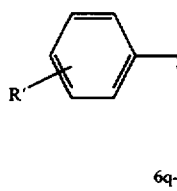
6q-y
Scheme III
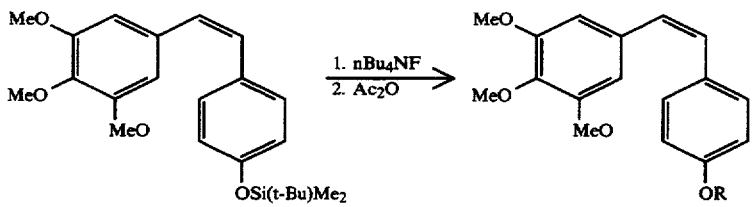
5m        5o R = H
              5p R = Ac
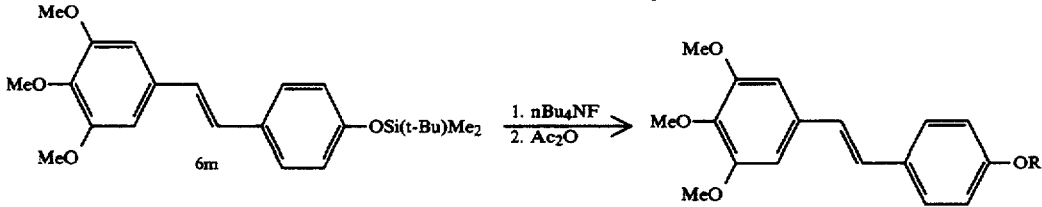
6m        6o R = H
              6p R = Ac

Scheme IV
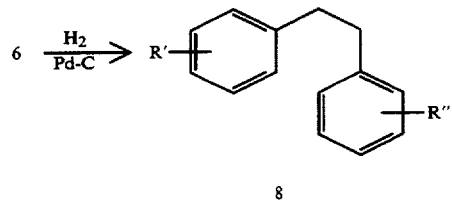
Scheme V
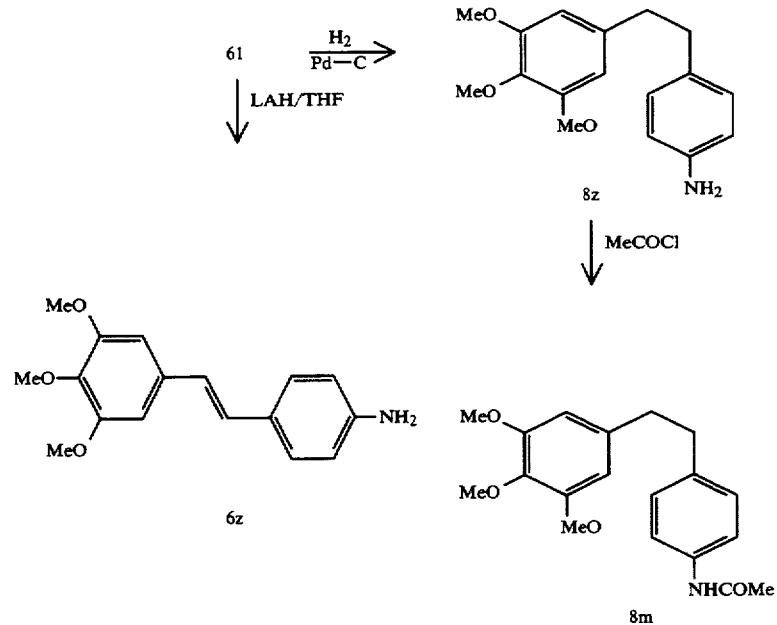
Scheme VI
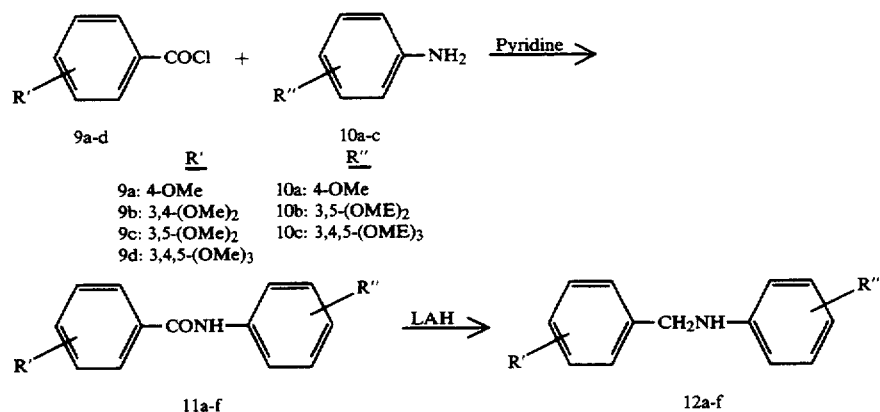
| R' | R'' |
|---|---|
| 9a: 4-OMe | 10a: 4-OMe |
| 9b: 3,4-(OMe)₂ | 10b: 3,5-(OMe)₂ |
| 9c: 3,5-(OMe)₂ | 10c: 3,4,5-(OMe)₃ |
| 9d: 3,4,5-(OMe)₃ | |
Scheme VII
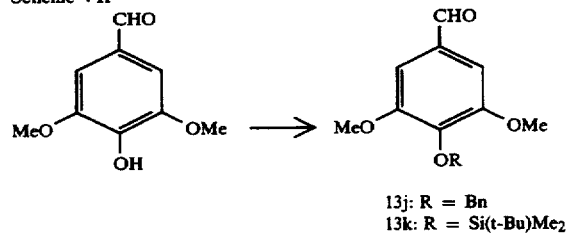
13j: R = Bn
13k: R = Si(t-Bu)Me₂
Scheme VIII -continued
Schemes
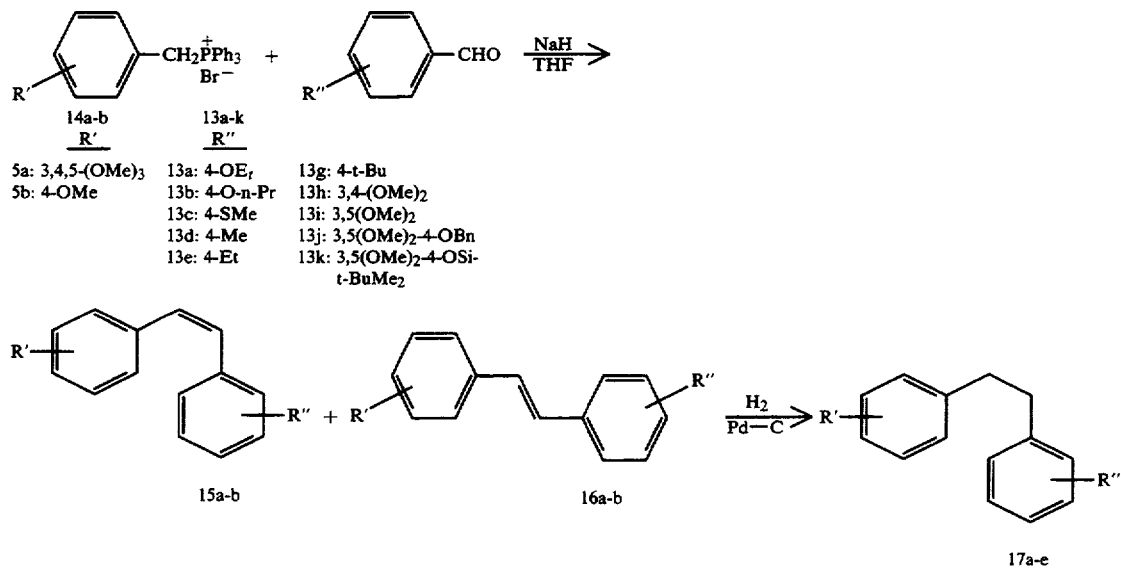
| 5a: 3,4,5-(OMe)₃ | 13a: 4-OEt | 13g: 4-t-Bu |
| 5b: 4-OMe | 13b: 4-O-n-Pr | 13h: 3,4-(OMe)₂ |
| | 13c: 4-SMe | 13i: 3,5(OMe)₂ |
| | 13d: 4-Me | 13j: 3,5(OMe)₂-4-OBn |
| | 13e: 4-Et | 13k: 3,5(OMe)₂-4-OSi-t-BuMe₂ |
Scheme IX
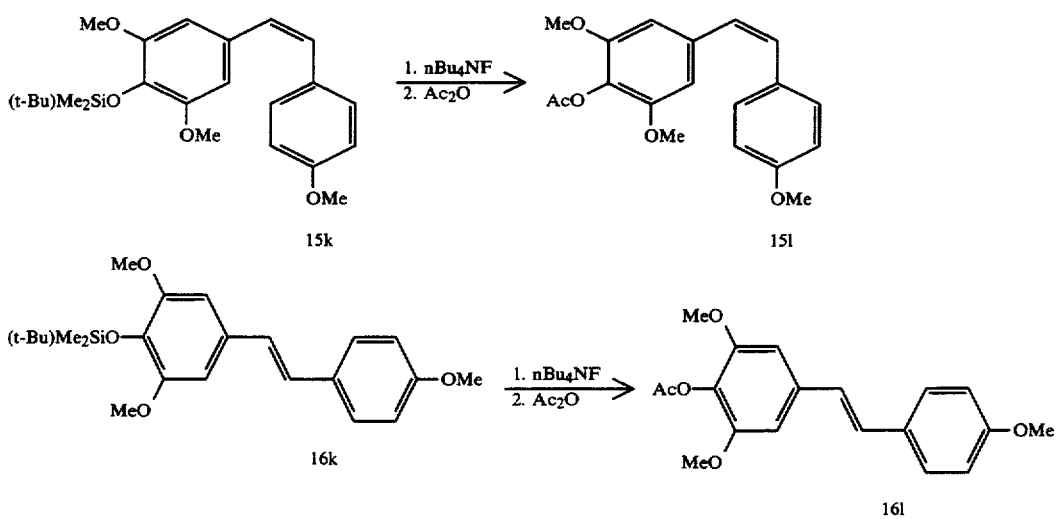
Scheme X
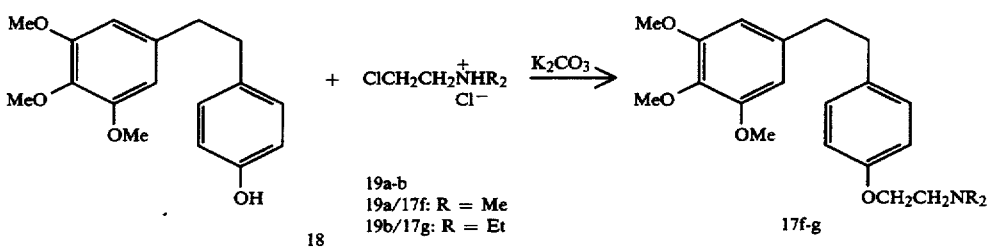
Scheme XI
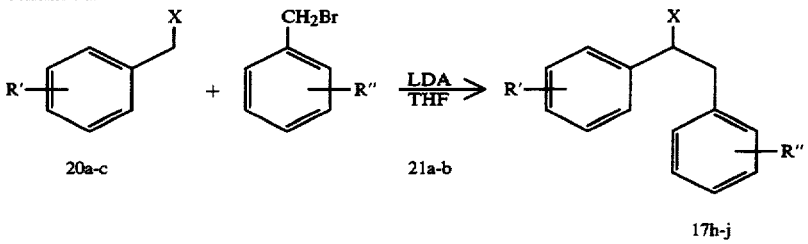

20a: R' = 3,4,5-(OMe)₃, X = CN
20b: R' = 4-OMe, X = COOMe
21a: R'' = 4-OMe
21b: R'' = 3,4,5-(OMe)₃
Scheme XII
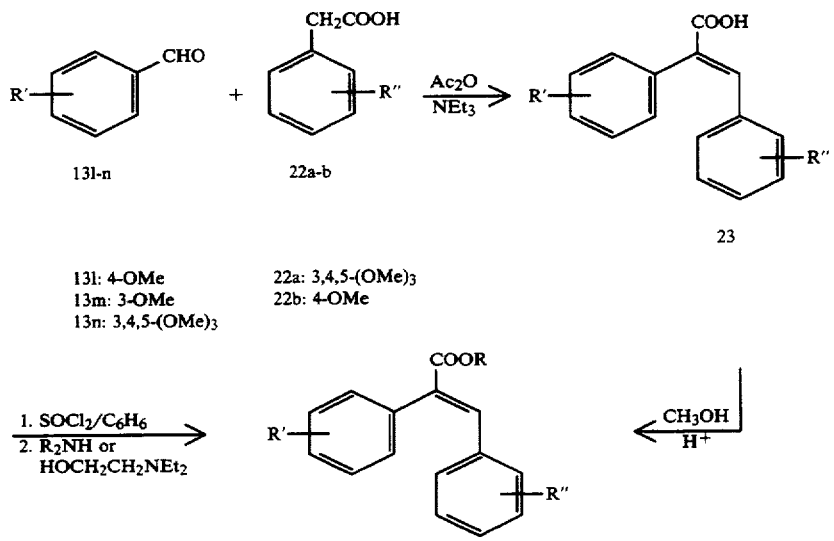
13l: 4-OMe
13m: 3-OMe
13n: 3,4,5-(OMe)₃
22a: 3,4,5-(OMe)₃
22b: 4-OMe
Scheme XIII
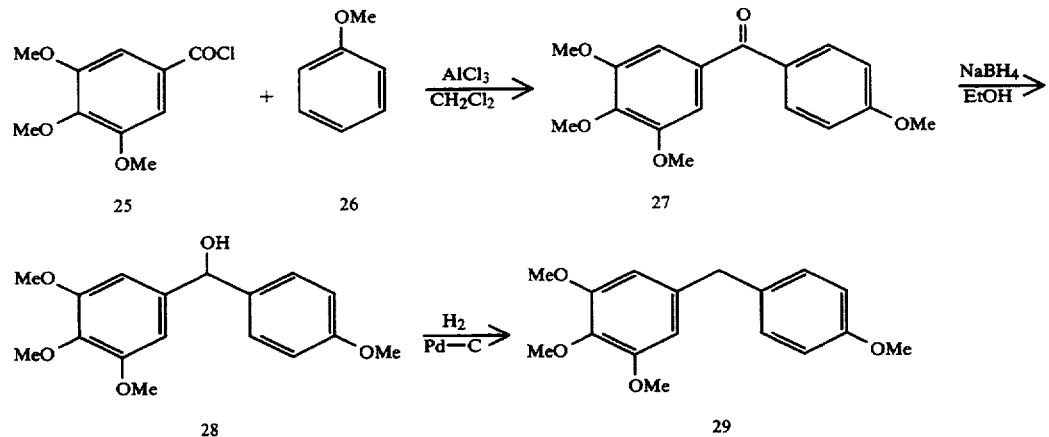
Scheme XIV
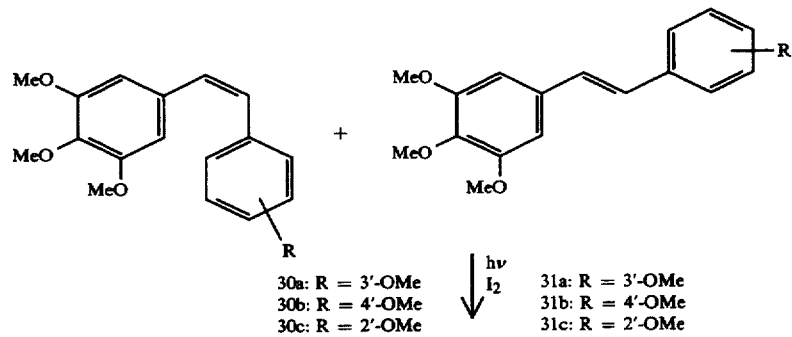
30a: R = 3'-OMe
30b: R = 4'-OMe
30c: R = 2'-OMe
31a: R = 3'-OMe
31b: R = 4'-OMe
31c: R = 2'-OMe

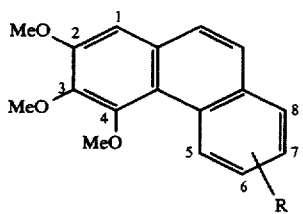
32a: R = 5-OMe
32b: R = 6-OMe
32c: R = 7-OMe
32d: R = 8-Ome
Scheme XV
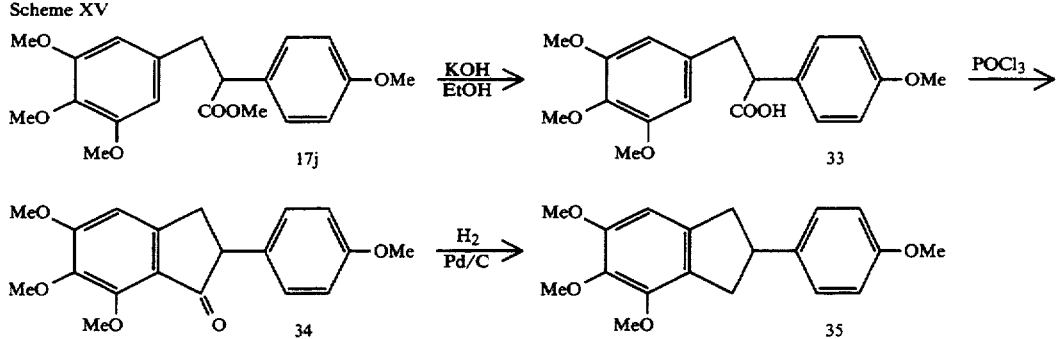
Scheme XVI
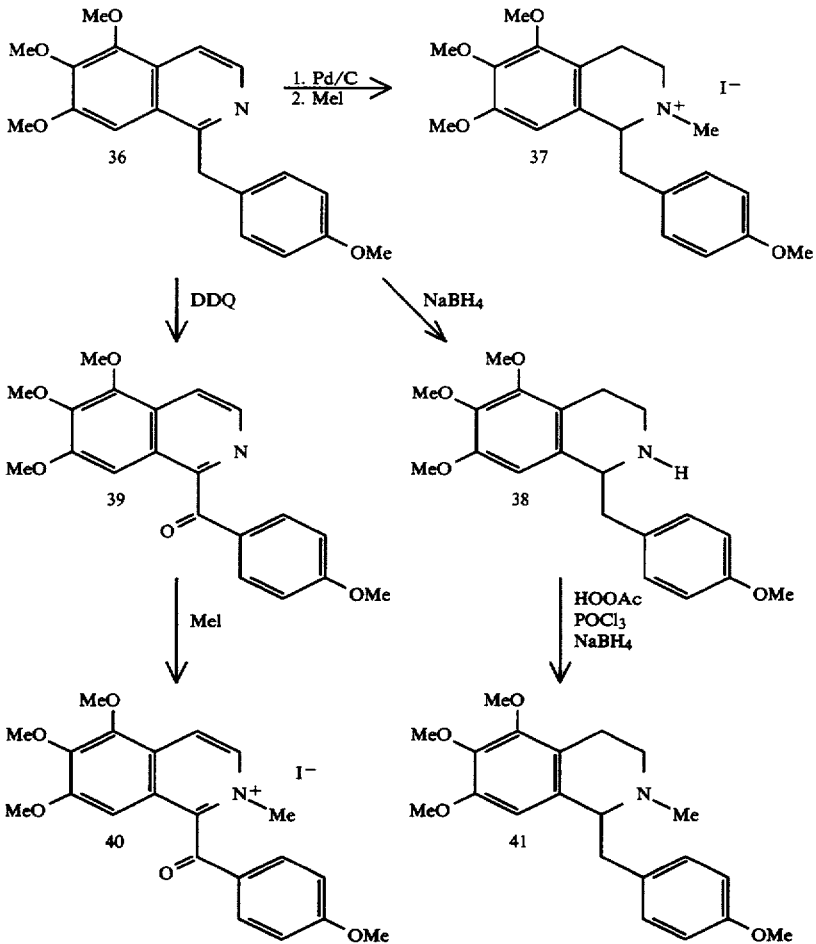
Scheme XVII -continued
Schemes

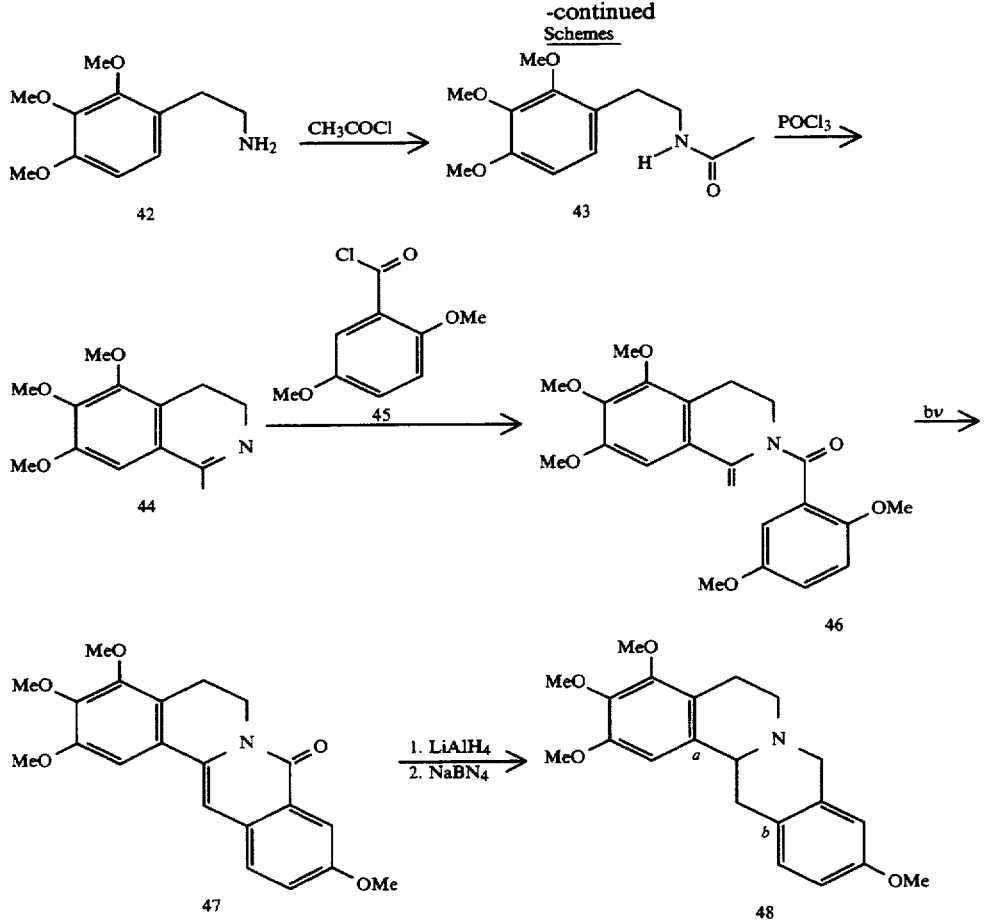

Compounds of the present invention exhibit tubulin polymerization inhibitory activity. They also display anti-tumor, especially anti-cancer activity, and thus, are anti-cancer agents, useful for the treatment of cancer, as shown by the assays described hereinbelow.

Pharmacological Testing

A wide variety of compounds encompassed by Formula I were synthesized and tested against five cancer cell cultures: A-549 lung carcinoma, MCF-7 breast carcinoma, HT-29 colon adenocarcinoma, SKMEL-5 melanoma and MLM melanoma. Pharmacological test results are summarized in Tables I-IX. Pharmacological testing procedures utilized were as follows.

Cytotoxicity Assays

An MTT (3-(4,5-dimethylthiazol-2-4)-2-5-diphenyl-tetrazolium) calorimetric assay was employed according to the established procedure of Alley, et al., Cancer Research, 48, Feb. 1, 1988, pgs. 589–601; and Mosmann, T., J. Immunol Meth., 65, (1983), pgs. 55–63. The description of these assays described therein are incorporated herein by reference. After the addition of the samples to the cell cultures, the cells were incubated for six days before the MTT reagent was added. The assays were performed at Purdue Cell Culture Laboratory. All of the compounds were initially tested once for each of the cell lines listed in Tables I-IV. The active compounds ($ED_{50} < 25$ μM) were tested again, and the values shown for these cytotoxic substances are the averages of two determinations.

Tubulin Polymerization and Colchicine Binding Assays

Electrophoretically homogeneous tubulin was purified from bovine brain as described previously by Hamel et al., Biochemistry, 23, (1984), pg. 4173. Determination of $IC_{50}$ values for the polymerization of purified tubulin was performed as described in detail by Muzaffar et al., J. Med. Chem., 33, (1990), pgs. 567–571, the pertinent contents of which are incorporated herein by reference. In brief, tubulin was preincubated at 37° C. with varying compound concentrations, reaction mixtures were chilled on ice, GTP (required for the polymerization reaction) was added, and polymerization was followed at 37° C. by turbidimetry at 350 nm in Gilford recording spectrophotometers equipped with electronic temperature controllers. Four instruments were used, and two control reaction mixtures were present in each experiment. The extent of polymerization after a 20 min incubation was determined (the values for the two controls were usually within 5% of each other). $IC_{50}$ values were determined graphically. Active compounds were examined in at least three independent assays, while inactive compounds (defined as $IC_{50}$ value $> 50$ μm) were examined in at least two independent experiments. (It is to be noted that the term "inactive", as used herein does not mean that a given compound has no activity. As used herein, the term means that it has activity, but its $IC_{50}$ value in a particular assay is $>50$ μm.) The effect of agents on the binding of [³H]colchicine (obtained from Amersham) to tubulin was measured by the DEAE-filter technique.

Among the first group of compounds tested (i.e., 4a to 12f), eleven of them, 5a, 5b, 5e–h, 5n, 6n, 8a, 8n, and 12a were found to have significant cytotoxicity ($ED_5$-

0<1 μM in at least three cell lines). In general, cis stilbenes were more potent than the other groups of compounds, and (Z)-1-(4-methoxyphenyl)-2-(3,4,5-trimethoxyphenyl)ethene (5a) was the most potent of all. Taking compound 5a as the model compound for a structure-activity relationship discussion, the presence of a 4-methoxy group in the B-ring plays a very important role for this compound to be highly cytotoxic. Transfer of the 4-methoxy group in the B-ring to the 3- or 2-position (compounds 5b and 5c) or substitution of it with H, $NO_2$, OSi(t-Bu)$Me_2$, OH, OAc (compounds 5f, 5l, 5m, 5o and 5p) decreased the activity drastically. Similarly, introduction of a Cl group at the 2-position of 5a (compound 5e) decreased the cytotoxicity. However, when the methoxy group in the B-ring was substituted with a Cl, Br, or $NMe_2$ group (compounds 5g, 5h, 5n), although the potency decreased they were still highly cytotoxic ($ED_{50} < 10^{-1}$ μM). Rotating the three A-ring methoxy groups from the 3,4,5-positions to the 2,3,4-positions reduced the cytotoxicity by more than five orders of magnitude. In another modification we replaced the B-ring of compound 5a with 4-, 3-, or 2-pyridyl rings (compounds 5i, 5j, 5k) and none of them were active ($ED_{50} > 10$ μM). These results show that the exact locations of the four methoxy groups are very important features for the pronounced cytotoxicity of compound 5a and that changes in their locations result in decreased potency. In comparison with combretastatin A-4 (1a), compound 5a was found to be approximately 140 times more cytotoxic against HT-29 cells and about 10 times more cytotoxic against MCF-7 cells than combretastatin A-4 (1a). However, 5a was found to be about 20 times less cytotoxic against A-549 cells, 30 times less cytotoxic against SKMEL-5, and 7 times less cytotoxic against MLM cells than combretastatin A-4 (1a).

Except for compound 6n, trans-stilbenes had lower activity. This includes tetramethylated piceatannol (6y), and its methoxylated derivatives 6s, 6t, 6u and 6v. Only two dihydrostilbenes (compounds 8a and 8n) were found to be highly active, with 8a being the second most cytotoxic agent prepared ($ED_{50}$ values about $2 \times 10^{-4}$ μM). Compound 8a was more cytotoxic than dihydrocombretastatin A-4 (1c) in all five cancer cell lines studied here. When the ethylene bridge in compound 8a was replaced with an amide or an aminomethylene linkage (compounds 11a, 11c, 12a, 12c and other analogues), none of the amides had significant activity ($ED_{50} > 1$ μM), but the N-benzylamine derivative 12a possessing the closest structural analogy to 8a was active. 3,4,5-Trimethoxy-N-(4-methoxyphenyl)-benzylamine (12a) was only an order of magnitude less cytotoxic than 8a ($ED_{50}$ in the $10^{-3}$ μM range).

The mechanism of action of the combretastatins has been shown to be at the microtubule level, since they cause cells to accumulate in apparent metaphase arrest and inhibit in vitro microtubule assembly. They bind specifically to tubulin, the major component of microtubules, at the colchicine binding site, since combretastatin A-4 (1a) has been shown to competitively inhibit the binding of radiolabeled colchicine to tubulin.

Initial investigation of several of the synthetic compounds prepared here revealed that they do in fact cause mitotic arrest in cell culture. A detailed quantitative study of the effects of most of these substances on tubulin polymerization was therefore performed. With the exception of compounds 5p and 12d, noncytotoxic agents had minimal effects on polymerization ($IC_{50}$ values > 50 μM), but significant inhibition of the reaction occurred with ten of the eleven highly cytotoxic compounds and with compounds 5p and 12d. Tubulin polymerization and colchicine binding inhibition data of the compounds encompassed hereby were compared with simultaneously obtained inhibitory data for the effects of combretastatin A-4 (1a; cf. 5a), its trans isomer (1b; cf. 6a), and its dihydro derivative (1c; cf. 8a) (Table VIII). Data are presented as well for podophyllotoxin, a potent tubulin inhibitor which binds at the colchicine site, and for thiocolchicine, a particularly potent colchicinoid which has reproducibly yielded the lowest $IC_{50}$ value in the polymerization assay for agents binding to the colchicine binding site.

Compound 5a is a most potent new agent as an inhibitor of tubulin polymerization, with an $IC_{50}$ value (2.2 μM) essentially indistinguishable from those of combretastatin A-4 and podophyllotoxin and somewhat higher than that of thiocolchicine. This is in agreement both with compound 5a possessing one of the highest cytotoxicity of the new compounds and with its close similarity to combretastatin A-4 (1a) in its overall effects on the cell lines evaluated. The difference in $IC_{50}$ values between the two dihydrostilbene compounds 1c and 8a was more noticeable. The combretastatin A-4 analog 1c had an $IC_{50}$ value of 3.3 μM, only modestly lower than the $IC_{50}$ value of combretastatin A-4, but the corresponding hydrogenation of compound 5a to yield compound 8a resulted in an almost 4-fold increase in the $IC_{50}$ value, from 2.2 to 7.9 μM. Similarly, the modest reduction in activity in the cis stilbene 5n as compared to combretastatin A-4 (1a) (3.5 versus 1.9 μM) was not reflected in the dihydrostilbene analog 8n, which had an $IC_{50}$ value of 29 μM. Cis stilbene compounds 5b, 5e, 5g, and 5h were also active as inhibitors of tubulin polymerization, while the remaining ten cis stilbenes had less activity. It should be noted that, with the exception of the most potent agents (1a and 5a), there was only qualitative agreement between the tubulin polymerization and cell culture assays. For example, while dihydrocombretastatin A-4 (compound 1c) was more effective than compound 8a as an inhibitor of tubulin polymerization, the latter agent was more cytotoxic with the cell lines studied here. Similarly, although the halogenated cis stilbenes 5e, 5g and 5h were not much less active than 1a and 5a as inhibitors of tubulin polymerization, they were about 1000-fold less cytotoxic.

The cytotoxic compounds gave reproducible results in the tubulin polymerization assay with the exception of the trans stilbenes 1b and 6n. Initial evaluation of these compounds in the tubulin polymerization assay yielded results concordant with the cytotoxicity data, although the apparent $IC_{50}$ value obtained in the polymerization assay for 6n was difficult to reproduce and that for 1b initially obtained in the current experiments was lower than that obtained previously. It was found that both 1b and 6n solutions increased in activity with storage, and that, when care was taken to evaluate the solutions immediately after their preparation, neither trans stilbene was able to significantly inhibit tubulin polymerization. This suggested that both compounds were unstable in solution, and that more active agents might be formed during their storage. The cytotoxic properties of these two agents may similarly result from chemical changes in solution. 500 MHz NMR analysis of 6n in solution demonstrated significant formation of the cis isomer 5n. The ratio of 6n:5n was 1:1 after 24 hours the dissolution of pure 6n in DMSO at room temperature. In a separate analysis of the stability of compound 1b in DMSO at room temperature (well protected from light), $^1$H NMR analysis over a period of one month at frequent intervals confirmed the formation of about 3% and 10% of the cis isomer (compound 1a) after two and four weeks, respectively.

Compounds 5a and 8a can be taken as standards for structure activity comparisons of cis stilbenes and dihydrostilbenes, respectively, in the tubulin polymerization assay. Without exception, when the same modified analog was available in both series, a greater loss of activity occurred in the dihydrostilbene than in the analogous cis stilbene (cf. 5b and 6b; 5f and 6f; 5n and 6n; 5p and 6p).

In the cis stilbene series, a shift of a single methoxy group in the A ring, from position 5 to position 2, yielded an inactive agent (5d). When the B ring methoxy group was shifted from position 4' to position 3', there was a 4-fold drop in activity (compound 5b; $IC_{50}$, 8.8 µM). When the B ring methoxy group was eliminated, there was a much larger drop in activity (compound 5f; $IC_{50}$, 36 µM), while its placement at the 2' position yielded the compound 5c, which exhibited low activity. Addition of a Cl at position 2' (compound 5e) or replacement of the methoxy group with a Cl (5g), Br (5h), or NMe$_2$ (5n) group resulted in small reductions in antibutulin activity. Demethylation of the 4'-methoxy group led to compound 5o, and its replacement with an acetyloxy group yielded a weak inhibitor (compound 5p; $IC_{50}$, 29 µM).

Turning to the dihydrostilbene series, replacement of the B ring methoxy group with an amino group (compound 8z) resulted in lower activity, but activity was increased if the amino group was converted to a dimethylamino group (compound 8n; cf. 5n). Addition of one (compound 8s) or two (compounds 8t–8v) additional methoxy groups to the B ring also resulted in lower activity. An enhancement of antitubulin activity in the 5a/8a structure was obtained by modification of the substituents on the B-phenyl ring by the addition of a single hydroxy group at position 3' (as occurs in combretastatin A-4 (1a) and dihydrocombretastatin A-4 (1c)) or addition of two hydroxy groups in a vicinal diol arrangement at positions 2' and 3' (as occurs in combretastatin A-1 and B-1).

Replacement of the ethylene bridge connecting the two aromatic rings in compound 8a with amide or aminomethylene units as represented by compounds 11a, 11d and 12c resulted in lower inhibitory activity in the tubulin polymerization assay. On the other hand, replacement of the ethylene bridge of 8a with an aminomethylene unit with the alternative orientation shown in compound 12a resulted in only a 3-fold loss of activity (increase in the $IC_{50}$ value from 7.9 µM for compound 8a to 23 µM for compound 12a). Comparing compound 12a to compound 12d indicates that only a small loss of activity occurs with elimination of the 4-methoxy group of the A ring ($IC_{50}$ of 29 µM without the methoxy group as opposed to 23 µM). However, the presence of a 4-methoxy group on the aniline partition of the benzylanilines increases activity.

Combretastatin A-4 (1a) and compound 1c inhibit the binding of radiolabeled colchicine to tubulin. Therefore Formula I compounds were evaluated in this assay too. The Formula I compounds relative activity as inhibitors of colchicine binding correlated well with their activity as inhibitors of tubulin polymerization. The mechanism of action of the new compounds, like that of the combretastatins, thus appears to involve an interaction of the drug with the colchicine binding site of tubulin. Only compound 5a, however, approached the nearly total inhibition of colchicine binding observed with equimolar combretastatin A-4 (1a).

With the compounds described here, as with the combretastatins and other classes of antimitotic agents, there is only partial agreement between cytotoxicity and effects on tubulin, the presumptive target molecule. Seven of the most cytotoxic agents (compounds 5a, 5b, 5e, 5g, 5h, 5n and 8a) were strong inhibitors of tubulin polymerization, and, except for the trans-stilbene 6n, no compound indicated to be inactive, as defined herein, as an inhibitor of tubulin polymerization had significant cytotoxic activity. Nevertheless, compounds 8n and 12a were strongly cytotoxic yet had only modest inhibitory effects on tubulin polymerization. Similarly, the structural differences between compounds 12a and 12d yielded only minor differences in antitubulin activity but resulted in major changes in their cytotoxic properties.

Besides the clear analogy of the compounds described here to the combretastatins, the activity observed in compound 5n, and to a lesser extent in compound 8n, suggests a relationship to the benzylbenzodioxole class of agents synthesized by Jurd. (See Jurd et al., J. Argic. Food Chem., 27, 1979, pg. 1007–1016 and Jurd, L., J. Heterocycl. Chem. 22, 1985, pg. 993.) Among the active tubulin inhibitors were compounds 13, 14 and 15 with the latter having the dimethylamino substituent in common with 5n.

The relative potencies 5a > 8a > 6a for these cis, dihydro, and trans compounds as inhibitors of tubulin polymerization are in agreement with the relative potencies previously observed for combretastatin A-4 (1a) and dihydrocombretastatin A-4 (1c) and our finding herein that freshly dissolved trans-combretastatin A-4 (1b) has some activity. Without wishing to be bound, it is assumed that the flexibility of the dihydro compound 8a allows it to adopt a conformation resembling the cis isomer 5a, which explains why compound 8a is more cytotoxic and potent as a tubulin polymerization inhibitor than the trans isomer compound 6a. The relative potencies 5a > 8a > 6a for these cis, dihydro, and trans compounds, respectively, as inhibitors of tubulin polymerization were also reflected in the results of the cytotoxicity assays. These relative potencies of 5a > 8a > 6a in the cytotoxicity assays are also in agreement with the relative cytotoxicities of 1a > 1c previously reported for L1210 murine leukemia cells in the combretastatin series, although in that study 1b was intermediate in cytotoxic activity between 1a and 1c.

As mentioned above, modifications were performed on (Z)-1-(4-methoxyphenyl)-2-(3,4,5-trimethoxyphenyl)ethene (5a) by rotating the four methoxy groups of both A- and B-rings to different positions and it was established that their locations as in compound 5a were essential for the pronounced cytotoxicity and antitubulin activity of 5a. As an extension of that investigation, additional cis stilbene derivatives were synthesized in which the 5-OMe or 4-OMe substituents were removed (compounds 15h and 15i, respectively) and these changes resulted in complete loss (15h:$ED_{50}$>25 µM in all cell lines) or significant reduction (15i:$ED_{50}$ in the $10^{-1}$ µM range) of the cytotoxicity. It is noteworthy that the ability of 15i to inhibit tubulin polymerization ($IC_{50}$ 3.8 µM) is not greatly reduced relative to that of 5a ($IC_{50}$ 2.5 µM), while that of 15h ($IC_{50}$ 18 µM) is about an order of magnitude less than that of 5a. It should be noted that the second series of cytotoxicity and tubulin polymerization experiments were performed independently of the first series in DMSO. Therefore, studies with both 5a and combretastatin A-4 were repeated as internal controls. In the cytotoxicity experiments significantly higher $ED_{50}$ values were obtained for both compounds in the later studies.

Next, major efforts were directed toward replacement of the 4-OMe group of the B-ring. In this line, seven cis stilbenes were prepared by substituting the methoxy group with OEt, O-n-Pr, SMe, Me, Et, i-propyl, or t-butyl groups (compounds 15a, 15b, 15c, 15d, 15e, 15f, and 15g, respectively). Substitution with a large group like t-butyl or O-benzyl (15g and 15j) resulted in the reduction of cytotoxicity by about 3 to 4 orders or magnitude and it greatly diminished ability to inhibit tubulin polymerization ($IC_{50}$ >40 $\mu M$). However, the compounds 15a-f were highly cytotoxic in all five cancer cell cultures, with potencies from 100 times less than to equal to that of combretastatin A-4. Replacement of the OMe of the B-ring with an SMe group (compound 15c) resulted in a compound which was as cytotoxic as the parent compound 15a in the A-549 and MLM cell cultures. However, the thiomethyl compound was about one order of magnitude less cytotoxic than 5a in the MCF cell culture, while being about one order of magnitude more potent that 5a in HT-29 cells and two orders of magnitude more potent in SKMEL-5 cells. The thiomethyl compound 15c is an analogue of thiocolchicine, which is more potent as a tubulin polymerization inhibitor and is more cytotoxic in certain cell cultures than colchicine. Substitution with i-propyl (compound 15f) decreased the cytotoxicity somewhat ($ED_{50}$ $7.0 \times 10^{-2}$ to $4.7 \times 10^{-4}$ $\mu M$ range), as did substitution with an O-n-propyl group (compound 15b). In addition to cytotoxicity, compounds 15a-f retained significant tubulin polymerization inhibitory activity relative to 5a. The decreased anti-tubulin activity of the 4-isopropyl compound 15f and the lack of activity of the 4-tert-butyl compound 15g demonstrates that an increase in steric bulk at this position results in a decrease in activity. Of particular interest is the enhancement of antitubulin activity which occurred with a reduction in size of the 4-substituent in the B-ring. The only new compound more effective than the parent compound 5a as an inhibitor of tubulin polymerization was 15d, in which a methyl group replaced the 4-methoxy group of 5a. The potency of this agent as a tubulin polymerization inhibitor was equivalent to combretastatin A-4 (1b), the natural product, even though it lacks the adjacent hydroxyl group in the B-ring.

Consistent with earlier observations, all the trans stilbenes (compounds 16a-1) were less potent than their corresponding cis isomers. Compounds 16a, 16c and 16f showed moderate cytotoxicity (in $1.0 \times 10^{-1}$ $\mu M$ range) in at least three cell lines and the other compounds were less potent.

Turning to the cis stilbenes with substitution on the olefinic bridge (Table V), introduction of substitutions on either the 1 or 2 position of the olefin reduced the cytotoxicity by from one to at least 5 orders of magnitude. In separate experiments, a COOH group was introduced on position 1 or 2 of the olefinic linkage and this resulted in the formation of compounds 23a and 23c ($ED_{50}$ 1.9 to >25 $\mu M$). However, when the COOH group of compound 23a was converted to the methyl ester (compound 24a) or the N-methylamide (compound 24c), the cytotoxicity increased 2 to 3 orders of magnitude in at least four cell cultures (as compared to 23a). Compounds 24a and 24c had $ED_{50}$ values of $5.0 \times 10^{-2}$ to $6.4 \times 10^{-3}$ $\mu M$ in A-549, MCF-7, HT-29, and SKMEL-5 cell cultures. However, the dimethylaminoethyl or diethylaminoethyl esters (compounds 24e and 24f) or the N-ethylamide (compound 24d) of compound 23a did not show considerable cytotoxicity. Transfer of the B-ring methoxy group in compound 23a to the 3-position (compound 23b) resulted in about 10 to 100-fold increase in the cytotoxicity in three cell lines and similar movement in compound 24a (compound 24b) reduced the cytotoxicity by 100 to 1000-fold.

Among the dihydrostilbene analogues of 8a (Table III), five compounds (17a, 17c-e and 17h) had $ED_{50}$ values of less than 1 $\mu M$ in at least four cell lines, with 3-(4-methoxyphenyl)-2-(3,4,5-trimethoxyphenyl)-propanonitrile (17h) being the most potent, both as a cytotoxic agent and as a tubulin polymerization inhibitor. However, this compound was about 10 to 100-fold less cytotoxic than 1-(4-methoxyphenyl)-2-(3,4,5-trimethoxyphenyl)ethane (8a), although its activity as a tubulin polymerization inhibitor ($IC_{50}$ 11 $\mu M$) was not decreased much relative to that of 8a ($IC_{50}$ 7.9 $\mu M$). While in the cis stilbene series, substitution of the B-ring methoxy with ethoxy, methyl, of ethyl reduced cytotoxicity by a maximum of two orders of magnitude, similar changes in the dihydrostilbene derivatives (compounds 17a, 17d and 17e) reduced cytotoxicity about 100 to 1000-fold. These dihydro compounds were also less potent as tubulin polymerization inhibitors. In the absence of the 3-hydroxyl group in the B-ring of combretastatin A-4 we have routinely observed a much larger loss of anti-tubulin activity upon reduction of the cis-stilbene to the dihydrostilbene than the approximately 50% loss of activity that occurs when combretastatin A-4 is reduced. Similarly, substitution with O-n-propyl, SMe, $O(CH_2)_2NMe_2$ or $O(CH_2)_2NEt_2$ groups (compounds 17b, 17c, 17f and 17g) also decreased cytotoxicity. Introduction of a CN group adjacent to the A-ring of 8A (compound 17h) reduced cytotoxicity by 10 to 100-fold, but a similar introduction of CN group adjacent to the B-ring (compound 17i) reduced cytotoxicity by 10,000-fold and, in contrast to 17h, the tubulin polymerization inhibitory activity of 17i ($IC_{50}$ >40 $\mu M$) was compromised relative to that of 8a. This relationship is identical to that observed when hydroxyl groups were introduced into corresponding positions in dihydrocombretastatin A-4. Conversion of the cyano group in compound 17i to a COOMe group resulted in the formation of a compound 17j ($ED_{50}$ >25 $\mu M$ in all cell cultures, $IC_{50}$ >40 $\mu M$ in the tubulin polymerization inhibition assay).

Several stilbenes and dihydrostilbenes containing acidic and basic groups were synthesized in an effort to obtain substances that could be more readily formulated. Included were 17f-g, 23a-c and 24e-f. None of these compounds inhibited tubulin polymerization significantly, and they were also in general not particularly cytotoxic.

In another set of modifications, the two-carbon bridge in 1-(4-methoxyphenyl)-2-(3,4,5-trimethoxyphenyl)ethane (8a) was reduced to a one carbon bridge (compounds 27, 28 and 29, Table VI). All of these compounds were less potent than 8a. 3,4,4',5-Tetra-methoxybenzophenone (27) was about 100 times less cytotoxic than 8a, although its tubulin polymerization inhibitory activity ($IC_{50}$ 7.4 $\mu M$) was essentially identical to that of 8a (IC$_{50}$ 7.9 μM). Conversion of 27 to the alcohol 28 reduced cytotoxicity by another 100 times and also resulted in lower tubulin polymerization inhibitory activity (IC$_{50}$ >40 μM). Hydrogenolysis of alcohol 28 to 4-methoxyphenyl-(3,4,5-trimethoxyphenyl)methane (29) increased the activity in the MCF-7, HT-29, and SKMEL systems to that comparable with 27, and increased the activity in the A-549 and MLM cell cultures. These effects on cytotoxicities were reflected in the tubulin polymerization inhibitory activity of 29 (IC$_{50}$ 15 μM) relative to that of 28 (IC$_{50}$>40 μM).

The antitubulin activities of the conformationally restricted analogues of the stilbene 5a and the dihydrostilbene 8a are included in Table VII. The data indicate that the active conformation of the stilbene 5a does not approach being planar, and involves a conformation in which at least one of the phenyl rings is twisted out of the plane of the other phenyl ring. In this context, it should be pointed out that the planar conformation of 5a is a high energy species due to a nonbonded interaction between the protons of the two aromatic rings that are ortho to the bridge. Consequently, a totally planar conformation of 5a is not expected to exist to any appreciable extent. The X-ray structure of combretastatin A-1 reveals that the normals to the least squares planes of the two phenyl rings are inclined 66° to each other. This likely represents a low energy conformation which may be involved in binding at the receptor site. Consistent with this hypothesis is the well documented and recognized fact that the planes of the trimethoxy-benzene ring and the other oxygen-substituted ring in podophyllotoxin, colchicine, steganacin, and combretastatin A-4 exist in similar dihedral relationships, so that these natural products resemble each other structurally to some extent when bound at the receptor site.

The results also imply that in the active conformation of 8a the dihedral angle between the two bridge bonds connected to the aromatic rings approaches 0°, so that the conformation would resemble the structure of the cis alkene 5a. This might explain the lower activity of the indane derivative 35, since in this case the dihedral angle between the relevant bonds would be closer to 120°. The lower inactivity of the benzylisoquinolines shown in Scheme XVI is more difficult to rationalize on conformational grounds because the benzyl group is more conformationally mobile. However, the tetrahydroprotoberberine system 48 is more conformationally restricted, with a dihedral angle between the relevant bonds labeled "a" and "b" in structure 48 of about 165°.

The low activity of the compounds in Table VII as tubulin polymerization inhibitors was reflected in their low cytotoxicites. None of these compounds had ED$_{50}$ values of less than 1 μM in any of the cell cultures.

Modifications can be made in the structure of combretastatin A-4 (1b) and its tetramethoxy analogue (5a) without substantially comprising cytotoxic and antitubulin activity. The cis-stilbene and benzylaniline configuration is most preferred, and all bridge substituents that have been tried to date reduce activity. The methoxy groups at positions 3, 4 and 5 in the A ring is preferred and substitution at positions 4 in the B ring is also highly preferred.

TABLE I

Cis Stilbenes

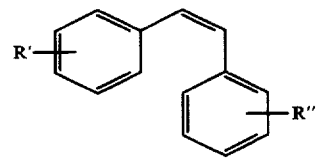

5

| No. | R' | R'' | A-549 | MCF-7 | HT-29 | SKMEL-5 | MLM | mp °C. |
|---|---|---|---|---|---|---|---|---|
| 5a | 3,4,5-(OMe)$_3$ | 4-OMe | 2.2 × 10$^{-5}$ | 1.2 × 10$^{-6}$ | 2.7 × 10$^{-5}$ | 9.7 × 10$^{-7}$ | 9.3 × 10$^{-5}$ | oil |
| 5b | 3,4,5-(OMe)$_3$ | 3-OMe | 1.3 × 10$^{-1}$ | 1.4 × 10$^{-1}$ | 9.0 × 10$^{-2}$ | 6.0 × 10$^{-2}$ | 1.4 | oil |
| 5c | 3,4,5-(OMe)$_3$ | 2-OMe | 1.1 | 1.3 | 8.7 × 10$^{-1}$ | 1.2 | 8.6 | oil |
| 5d | 2,3,4-(OMe)$_3$ | 4-OMe | 9.7 × 10$^{-1}$ | 2.3 × 10$^{-1}$ | 1.0 | 1.1 | 10.9 | 55-7 |
| 5e | 3,4,5-(OMe)$_3$ | 2-Cl-4-OMe | 5.1 × 10$^{-2}$ | 4.6 × 10$^{-2}$ | 6.6 × 10$^{-2}$ | 1.7 × 10$^{-2}$ | 1.4 × 10$^{-1}$ | oil |
| 5f | 3,4,5-(OMe)$_3$ | H | 1.7 × 10$^{-1}$ | 2.5 × 10$^{-1}$ | 8.4 × 10$^{-2}$ | 1.2 × 10$^{-1}$ | >25 | oil |
| 5g | 3,4,5-(OMe)$_3$ | 4-Cl | 8.0 × 10$^{-2}$ | 1.8 × 10$^{-2}$ | 5.0 × 10$^{-2}$ | 1.0 × 10$^{-2}$ | 1.7 × 10$^{-1}$ | oil |
| 5h | 3,4,5-(OMe)$_3$ | 4-Br | 1.1 × 10$^{-2}$ | 1.6 × 10$^{-2}$ | 8.2 × 10$^{-3}$ | 6.7 × 10$^{-3}$ | 1.4 × 10$^{-2}$ | oil |
| 5i | 1-(4-Pyridyl)-2-(3,4,5-trimethoxyphenyl)ethene | | 14.2 | 17.0 | 12.9 | 14.4 | >25 | oil |
| 5j | 1-(3-Pyridyl)-2-(3,4,5-trimethoxyphenyl)ethene | | 13.7 | 14.7 | 9.8 | 6.0 | >25 | oil |
| 5k | 1-(2-Pyridyl)-2-(3,4,5-trimethoxyphenyl)ethene | | >25 | >25 | >25 | >25 | >25 | oil |
| 5l | 3,4,5 (OMe)$_3$ | 4-NO$_2$ | >25 | >25 | >25 | >25 | >25 | 140-2 |
| 5m | 3,4,5-(OMe)$_3$ | 4-OSi(t-Bu)Me$_2$ | 10.95 | 7.29 | 10.60 | 7.59 | 17.23 | oil |
| 5n | 3,4,5-(OMe)$_3$ | 4-NMe$_2$ | 4.1 × 10$^{-3}$ | 5.8 × 10$^{-3}$ | 8.1 × 10$^{-3}$ | 1.5 × 10$^{-4}$ | 9.4 × 10$^{-3}$ | oil |
| 5o | 3,4,5-(OMe)$_3$ | 4-OH | 12.70 | 5.70 | 1.75 | 2.27 | 12.60 | 148-150 |
| 5p | 3,4,5-(OMe)$_3$ | 4-OAc | 1.7 | 3.0 × 10$^{-1}$ | 6.0 | 6.0 × 10$^{-1}$ | 6.3 | oil |
| 1a | Combretastatin A-4 | | 1.2 × 10$^{-6}$ | 3.8 × 10$^{-6}$ | 1.2 × 10$^{-5}$ | 3.0 × 10$^{-8}$ | 1.4 × 10$^{-5}$ | — |
| | Adriamycin | | 2.9 × 10$^{-2}$ | 3.1 × 10$^{-2}$ | 5.5 × 10$^{-2}$ | 3.2 × 10$^{-2}$ | 1.3 × 10$^{-1}$ | — |
| 15a | 3,4,5-(OMe)$_3$ | 4-OEt | 1.6 × 10$^{-3}$ | 9.6 × 10$^{-2}$ | 1.8 × 10$^{-3}$ | 2.5 × 10$^{-3}$ | 2.9 × 10$^{-2}$ | oil |
| 15b | 3,4,5-(OMe)$_3$ | 4-OPr$^n$ | 3.9 × 10$^{-2}$ | 6.6 × 10$^{-1}$ | 2.8 × 10$^{-2}$ | 1.4 × 10$^{-2}$ | 6.5 × 10$^{-2}$ | oil |
| 15c | 3,4,5-(OMe)$_3$ | 4-SMe | 1.9 × 10$^{-4}$ | 5.4 × 10$^{-3}$ | 1.8 × 10$^{-5}$ | 4.0 × 10$^{-6}$ | 3.3 × 10$^{-3}$ | oil |
| 15d | 3,4,5-(OMe)$_3$ | 4-Me | 9.4 × 10$^{-4}$ | 2.4 × 10$^{-2}$ | 2.3 × 10$^{-3}$ | 8.3 × 10$^{-4}$ | 6.6 × 10$^{-3}$ | oil |
| 15e | 3,4,5-(OMe)$_3$ | 4-Et | 1.2 × 10$^{-2}$ | 7.2 × 10$^{-2}$ | 2.7 × 10$^{-3}$ | 8.6 × 10$^{-4}$ | 7.5 × 10$^{-3}$ | oil |
| 15f | 3,4,5-(OMe)$_3$ | 4-Pr$^i$ | 6.6 × 10$^{-3}$ | 1.4 × 10$^{-3}$ | 2.4 × 10$^{-3}$ | 4.7 × 10$^{-4}$ | 7.0 × 10$^{-2}$ | oil |
| 15g | 3,4,5-(OMe)$_3$ | 4-Bu$^t$ | 1.02 | 1.57 | 8.8 × 10$^{-1}$ | 2.1 × 10$^{-1}$ | 4.32 | oil |
| 15h | 3,4-(OMe)$_2$ | 4-OMe | >25 | >25 | >25 | >25 | >25 | oil |
| 15i | 3,5-(OMe)$_2$ | 4-OMe | 1.3 × 10$^{-1}$ | 1.6 × 10$^{-1}$ | 3.4 × 10$^{-1}$ | 4.2 × 10$^{-1}$ | 9.8 × 10$^{-2}$ | oil |
| 16j | 3,5-(OMe)$_3$; 4-OBn | 4-OMe | 1.04 | 1.92 | 9.5 × 10$^{-1}$ | 6.1 × 10$^{-1}$ | >25 | oil |
| 15k | 3,5-(OMe)$_2$; | 4-OMe | >25 | >25 | 9.0 | >25 | >25 | oil |

TABLE I-continued

Cis Stilbenes

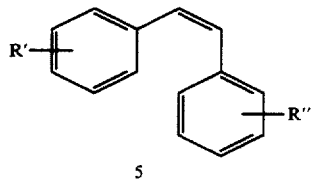

| No. | R' | R'' | A-549 | MCF-7 | HT-29 | SKMEL-5 | MLM | mp °C. |
|---|---|---|---|---|---|---|---|---|
| | | | \multicolumn{5}{c}{Cytotoxicity (ED$_{50}$ in $\mu$M)} | |
| 15l | 4-OSi(t-Bu)Me$_2$ 3,5-(OMe)$_2$; 4-OAc | 4-OMe | 21.5 | >25 | 8.7 | 0.6 | >25 | oil |

TABLE II

Trans Stilbenes

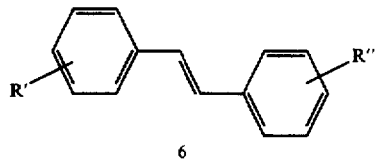

| No. | R' | R'' | A-549 | MCF-7 | HT-29 | SKMEL-5 | MLM | mp °C. |
|---|---|---|---|---|---|---|---|---|
| 6a | 3,4,5-(OMe)$_3$ | 4-OMe | 1.18 | 1.05 | 1.82 | $8.1 \times 10^{-1}$ | 2.07 | 152-5[38,39] |
| 6b | 3,4,5-(OMe)$_3$ | 3-OMe | 9.8 | 12.2 | 7.3 | 10.5 | >25 | 123-5 |
| 6c | 3,4,5-(OMe)$_3$ | 2-OMe | 12.2 | 18.0 | 12.1 | 13.5 | >25 | oil |
| 6e | 3,4,5-(OMe)$_3$ | 2-Cl-4-OMe | >25 | >25 | >25 | >25 | >25 | oil |
| 6f | 3,4,5-(OMe)$_3$ | H | >25 | >25 | >25 | >25 | >25 | 105-6[28] |
| 6g | 3,4,5-(OMe)$_3$ | 4-Cl | >25 | >25 | >25 | >25 | >25 | 147-9 |
| 6h | 3,4,5-(OMe)$_3$ | 4-Br | 6.47 | 9.14 | 12.69 | 6.53 | 5.13 | 155-6 |
| 6i | 1-(4-Pyridyl)-2-(3,4,5-trimethoxyphenyl)ethene | | >25 | >25 | >25 | >25 | >25 | 247-8[47] |
| 6j | 1-(3-Pyridyl)-2-(3,4,5-trimethoxyphenyl)ethene | | >25 | >25 | >25 | >25 | >25 | 103-5[48] |
| 6l | 3,4,5-(OMe)$_3$ | 4-NO$_2$ | >25 | >25 | >25 | >25 | >25 | 192-4[40] |
| 6m | 3,4,5-(OMe)$_3$ | 4-OSi(t-Bu)Me$_2$ | >25 | >25 | >25 | >25 | >25 | oil |
| 6n | 3,4,5-(OMe)$_3$ | 4-NMe$_2$ | $6.1 \times 10^{-3}$ | $8.2 \times 10^{-2}$ | $6.9 \times 10^{-3}$ | $4.6 \times 10^{-3}$ | $1.25 \times 10^{-2}$ | 114-5 |
| 6o | 3,4,5-(OMe)$_3$ | 4-OH | >25 | 18.63 | >25 | 11.55 | 24.15 | 188-90[8] |
| 6p | 3,4,5-(OMe)$_3$ | 4-OAc | 9.7 | 9.6 | 5.4 | 4.6 | 13.0 | oil |
| 6q | 3,4-(OMe)$_2$ | H | >25 | >25 | >25 | >25 | >25 | 106-8[41] |
| 6r | 2,3,4-(OMe)$_3$ | H | >25 | >25 | >25 | >25 | >25 | 79-82 |
| 6s | 3,4,5-(OMe)$_3$ | 3,5-(OMe)$_2$ | >25 | >25 | >25 | >25 | >25 | 132-4[49] |
| 6t | 3,4,5-(OMe)$_3$ | 2,3,4-(OMe)$_3$ | 12.5 | 14.72 | 10.27 | 10.64 | 23.86 | 87-8 |
| 6u | 3,4,5-(OMe)$_3$ | 3,4,5-(OMe)$_3$ | >25 | >25 | >25 | >25 | >25 | 174-5[50] |
| 6v | 3,4,5-(OMe)$_3$ | 2,4,5-(OMe)$_3$ | >25 | >25 | >25 | >25 | >25 | 147-8 |
| 6w | 2,4,5-(OMe)$_3$ | H | >25 | 8.5 | >25 | >25 | >25 | 81-2 |
| 6x | 2,4,6-(OMe)$_3$ | H | >25 | >25 | >25 | >25 | >25 | 57-9[51,52] |
| 6y | 3,4-(OMe)$_2$ | 3,5-(OMe)$_2$ | >25 | >25 | >25 | >25 | >25 | 65-7[49] |
| 6z | 3,4,5-(OMe)$_3$ | NH$_2$ | >25 | >25 | >25 | >25 | >25 | 251-3 |
| | Adriamycin | | $2.9 \times 10^{-2}$ | $3.1 \times 10^{-2}$ | $5.5 \times 10^{-2}$ | $3.2 \times 10^{-2}$ | $1.3 \times 10^{-1}$ | — |
| 16a | 3,4,5-(OMe)$_3$ | 4-OEt | $1.7 \times 10^{-1}$ | $7.5 \times 10^{-1}$ | 1.49 | 1.17 | $2.2 \times 10^{-1}$ | 87-88 |
| 16b | 3,4,5-(OMe)$_3$ | 4-OPr$^n$ | 9.2 | 12.5 | >25 | >25 | >25 | 82-83 |
| 16c | 3,4,5-(OMe)$_3$ | 4-SMe | $4.7 \times 10^{-1}$ | $5.9 \times 10^{-2}$ | $8.3 \times 10^{-2}$ | $2.8 \times 10^{-1}$ | 7.3 | 109-111 |
| 16d | 3,4,5-(OMe)$_3$ | 4-Me | 1.1 | 1.9 | $9.0 \times 10^{-1}$ | $8.0 \times 10^{-1}$ | 6.3 | 125-127 |
| 16e | 3,4,5-(OMe)$_3$ | 4-Et | $1.3 \times 10^{-1}$ | 1.2 | $1.1 \times 10^{-1}$ | $1.7 \times 10^{-1}$ | $2.2 \times 10^{-1}$ | 97-99 |
| 16f | 3,4,5-(OMe)$_3$ | 4-Pr$^i$ | 9.8 | 18.4 | 6.8 | 11.1 | >25 | 74-75 |
| 16g | 3,4,5-(OMe)$_3$ | 4-Bu$^t$ | >25 | >25 | >25 | >25 | >25 | 127-128 |
| 16h | 3,4-(OMe)$_2$ | 4-OMe | 11.7 | >25 | >25 | >25 | >25 | 135-137 |
| 16i | 3,5-(OMe)$_2$ | 4-OMe | 7.5 | 9.7 | 6.9 | $8.8 \times 10^{-1}$ | >25 | 55-56 |
| 16j | 3,5-(OMe)$_3$; 4-OBn | 4-OMe | >25 | >25 | 17.8 | >25 | >25 | 104-105 |
| 16k | 2,3-(OMe)$_2$; 4-OSi(t-Bu)Me$_2$ | 4-OMe | >25 | >25 | >25 | >25 | >25 | 118-120 |
| 16l | 3,5-(OMe)$_2$; 4-OAc | 4-OMe | 16.4 | 19.4 | 11.7 | 10.2 | 21 | 129-131 |

TABLE III

Dihydrostilbenes

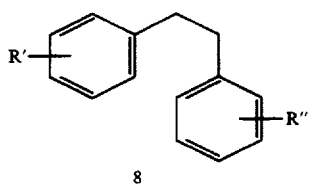

8

| No. | R' | R'' | Cytotoxicity (ED$_{50}$ in μM) A-549 | MCF-7 | HT-29 | SKMEL-5 | MLM | mp °C. |
|---|---|---|---|---|---|---|---|---|
| 8a | 3,4,5-(OMe)$_3$ | 4-OMe | $1.8 \times 10^{-4}$ | $1.6 \times 10^{-4}$ | $2.5 \times 10^{-4}$ | $1.4 \times 10^{-4}$ | $1.8 \times 10^{-4}$ | 73–5[39] |
| 8b | 3,4,5-(OMe)$_3$ | 3-OMe | 11.7 | 12.4 | 7.6 | 9.2 | >25 | oil |
| 8c | 3,4,5-(OMe)$_3$ | 2-OMe | 13.5 | 11.8 | >25 | 20 | >25 | oil |
| 8f | 3,4,5-(OMe)$_3$ | H | >25 | >25 | >25 | >25 | >25 | oil |
| 8i | 1-(4-Pyridyl)-2-(3,4,5-trimethoxyphenyl)ethane | | >25 | >25 | >25 | >25 | >25 | oil |
| 8j | 1-(3-Pyridyl)-2-(3,4,5-trimethoxyphenyl)ethane | | 12.2 | >25 | >25 | >25 | >25 | oil[48] |
| 8m | 3,4,5-(OMe)$_3$ | 4-NHCOCH$_3$ | >25 | >25 | >25 | >25 | >25 | 112–4 |
| 8n | 3,4,5-(OMe)$_3$ | 4-NMe$_2$ | $8.3 \times 10^{-2}$ | $6.4 \times 10^{-2}$ | $7.7 \times 10^{-2}$ | $5.9 \times 10^{-2}$ | $1.2 \times 10^{-1}$ | oil |
| 8o | 3,4,5-(OMe)$_3$ | 4-OH | >25 | >25 | >25 | >25 | >25 | 108–110[8] |
| 8p | 3,4,5-(OMe)$_3$ | 4-OAc | 19.0 | >25 | >25 | >25 | >25 | oil |
| 8q | 3,4-(OMe)$_2$ | H | >25 | >25 | >25 | >25 | >25 | oil |
| 8r | 2,3,4-(OMe)$_3$ | H | >25 | >25 | >25 | >25 | >25 | oil |
| 8s | 3,4,5-(OMe)$_3$ | 3,5-(OMe)$_2$ | >25 | >25 | >25 | >25 | >25 | 76–7[49] |
| 8t | 3,4,5-(OMe)$_3$ | 2,3,4-(OMe)$_3$ | >25 | >25 | >25 | >25 | >25 | oil |
| 8u | 3,4,5-(OMe)$_3$ | 3,4,5-(OMe)$_3$ | >25 | >25 | >25 | >25 | >25 | 137–8[53] |
| 8v | 3,4,5-(OMe)$_3$ | 2,4,5-(OMe)$_3$ | >25 | >25 | >25 | >25 | >25 | 88–9 |
| 8z | 3,4,5-(OMe)$_3$ | 4-NH$_2$ | 12.23 | 11.88 | 24.56 | 12.65 | >25 | 84–5 |
| 1c | Dihydrocombretastatin A-4 | | $1.0 \times 10^{-2}$ | $3.3 \times 10^{-1}$ | $8.1 \times 10^{-3}$ | $2.1 \times 10^{-3}$ | $1.0 \times 10^{-2}$ | — |
| | Adriamycin | | $2.9 \times 10^{-2}$ | $3.1 \times 10^{-2}$ | $5.5 \times 10^{-2}$ | $3.2 \times 10^{-2}$ | $1.3 \times 10^{-1}$ | — |

| No. | R' | Y | Z | R'' | Cytotoxicity (ED$_{50}$ in μM) A-549 | MCF-7 | HT-29 | SKMEL-5 | MLM | mp °C. |
|---|---|---|---|---|---|---|---|---|---|---|
| 17a | 3,4,5-(OMe)$_3$ | H | H | 4-OEt | $1.9 \times 10^{-1}$ | $1.9 \times 10^{-1}$ | $1.8 \times 10^{-1}$ | $1.7 \times 10^{-1}$ | $2.7 \times 10^{-1}$ | oil |
| 17b | 3,4,5-(OMe)$_3$ | H | H | 4-OPr$^n$ | 7.2 | 3.9 | 6.4 | 6.7 | 15.0 | oil |
| 17c | 3,4,5-(OMe)$_3$ | H | H | 4-SMe | $1.5 \times 10^{-1}$ | $2.0 \times 10^{-1}$ | $4.0 \times 10^{-3}$ | $2.4 \times 10^{-1}$ | 1.3 | 52–54 |
| 17d | 3,4,5-(OMe)$_3$ | H | H | 4-Me | $1.8 \times 10^{-1}$ | $2.2 \times 10^{-1}$ | $1.0 \times 10^{-1}$ | $1.1 \times 10^{-1}$ | 1.4 | 51–52 |
| 17e | 3,4,5-(OMe)$_3$ | H | H | 4-Bt | $8.8 \times 10^{-2}$ | $1.6 \times 10^{-1}$ | $1.6 \times 10^{-2}$ | $4.7 \times 10^{-2}$ | $2.7 \times 10^{-1}$ | oil |
| 17f | 3,4,5-(OMe)$_3$ | H | H | 4-O(CH$_2$)$_2$NMe$_2$ | >25 | 10.3 | 9.8 | 11.4 | >25 | oil |
| 17g | 3,4,5-(OMe)$_3$ | H | H | 4-O(CH$_2$)$_2$NEt$_2$ | 6.8 | 4.3 | 5.2 | 8.5 | >25 | oil |
| 17h | 3,4,5-(OMe)$_3$ | CN | H | 4-OMe | $9.6 \times 10^{-3}$ | $1.4 \times 10^{-2}$ | $7.5 \times 10^{-3}$ | $4.1 \times 10^{-3}$ | $1.6 \times 10^{-2}$ | 82–83 |
| 17i | 3,4,5-(OMe)$_3$ | H | CN | 4-OMe | 11.5 | 14.3 | 9.4 | 6.4 | 21.1 | 102–103 |
| 17j | 3,4,5-(OMe)$_3$ | H | COOMe | 4-OMe | >25 | >25 | >25 | >25 | >25 | 84–85 |

TABLE IV

Benzamides and Benzylamines.

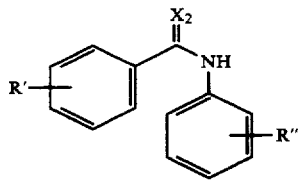

11, 12

| No. | R' | R'' | X$_2$ | Cytotoxicity (ED$_{50}$ in μM) A-549 | MCF-7 | HT-29 | SKMEL-5 | MLM | mp °C. |
|---|---|---|---|---|---|---|---|---|---|
| 11a | 3,4,5-(OMe)$_3$ | 4-OMe | O | 14.07 | 12.21 | 22.65 | >25 | >25 | 160–1[42] |
| 11b | 3,4-(OMe)$_2$ | 3,4,5-(OMe)$_3$ | O | >25 | >25 | >25 | >25 | >25 | 155–6 |
| 11c | 4-OMe | 3,4,5-(OMe)$_3$ | O | >25 | >25 | >25 | >25 | >25 | 159–160 |
| 11d | 3,5-(OMe)$_2$ | 4-OMe | O | 9.02 | 5.47 | 14.52 | 11.88 | >25 | 104–5 |
| 11e | 4-OMe | 3,5-(OMe)$_2$ | O | >25 | >25 | >25 | >25 | >25 | 105–6 |
| 11f | 3,4,5-(OMe)$_3$ | 3,4,5-(OMe)$_3$ | O | >25 | >25 | >25 | >25 | >25 | 211–2 |
| 12a | 3,4,5-(OMe)$_3$ | 4-OMe | H$_2$ | $1.9 \times 10^{-3}$ | $2.4 \times 10^{-3}$ | $1.0 \times 10^{-3}$ | $7.0 \times 10^{-4}$ | $1.6 \times 10^{-3}$ | 73–4 |
| 12b | 3,4-(OMe)$_2$ | 3,4,5-(OMe)$_3$ | H$_2$ | >25 | >25 | >25 | >25 | >25 | oil |
| 12c | 4-OMe | 3,4,5-(OMe)$_3$ | H$_2$ | $8.3 \times 10^{-1}$ | $8.6 \times 10^{-1}$ | 2.24 | 1.13 | >25 | 77–8 |
| 12d | 3,5-(OMe)$_2$ | 4-OMe | H$_2$ | 5.71 | 6.08 | 17.84 | 2.41 | >25 | oil |
| 12e | 4-OMe | 3,5-(OMe)$_2$ | H$_2$ | >25 | >25 | >25 | >25 | >25 | oil |
| 12f | 3,4,5-(OMe)$_3$ | 3,4,5-(OMe)$_3$ | H$_2$ | >25 | >25 | >25 | >25 | >25 | 127–8 |
| | Adriamycin | | | $2.9 \times 10^{-2}$ | $3.1 \times 10^{-2}$ | $5.5 \times 10^{-2}$ | $3.2 \times 10^{-2}$ | $1.3 \times 10^{-1}$ | — |

TABLE V

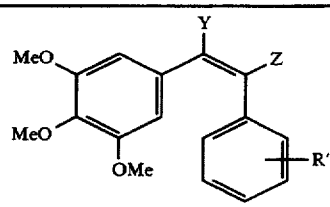

| No. | Y | Z | R' | A-549 | MCF-7 | HT-29 | SKMEL-5 | MLM | mp °C. | Inhibition of Tubulin Polymerization IC$_{50}$ ($\mu$M) ($\pm$S.D.) |
|---|---|---|---|---|---|---|---|---|---|---|
| | | | | Cytotoxicity (ED$_{50}$ in $\mu$M) | | | | | | |
| 23a | COOH | H | 4-OMe | 13.9 | 12.8 | 8.4 | 9.1 | >25 | 187–189 | >40 |
| 23b | COOH | H | 3-OMe | $2.5 \times 10^{-2}$ | >25 | $1.2 \times 10^{-1}$ | $5.0 \times 10^{-2}$ | >25 | 178–180 | >40 |
| 23c | H | COOH | 4-OMe | 5.2 | 1.9 | 5.9 | 2.3 | >25 | 206–207 | >40 |
| 24a | COOMe | H | 4-OMe | $1.1 \times 10^{-2}$ | $2.0 \times 10^{-2}$ | $9.5 \times 10^{-3}$ | $6.4 \times 10^{-3}$ | 9.6 | 74–75 | >40 |
| 24b | COOMe | H | 3-OMe | 1.3 | 1.3 | $7.0 \times 10^{-1}$ | 1.5 | 15.5 | 87–88 | >40 |
| 24c | CONHMe | H | 4-OMe | $2.4 \times 10^{-2}$ | $5.0 \times 10^{-2}$ | $2.6 \times 10^{-2}$ | $2.4 \times 10^{-2}$ | 9.3 | 172–174 | 35 ($\pm$2) |
| 24d | CONHEt | H | 4-OMe | 3.4 | 3.7 | 1.8 | 7.05 | >25 | 152–154 | >40 |
| 24e | COO(CH$_2$)$_2$NEt$_2$ | H | 4-OMe | 1.8 | 2.1 | 2.8 | 2.7 | >25 | oil | >40 |
| 24f | COO(CH$_2$)$_2$NMe$_2$ | H | 4-OMe | 7.7 | 10.4 | >25 | 6.7 | >25 | oil | >40 |
| | H | H | 4-OMe | $3.7 \times 10^{-4}$ | $6.2 \times 10^{-4}$ | $2.6 \times 10^{-4}$ | $2.6 \times 10^{-4}$ | $1.6 \times 10^{-3}$ | oil | 2.5 ($\pm$0.8) |

TABLE VI

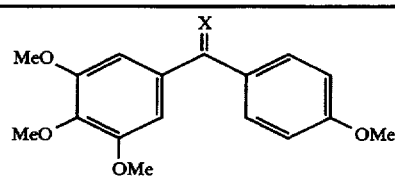

| No. | X | A-549 | MCF-7 | HT-29 | SKMEL-5 | MLM | mp °C. | Inhibition of Tubulin Polymerization IC$_{50}$ ($\mu$M) ($\pm$S.D.) |
|---|---|---|---|---|---|---|---|---|
| | | Cytotoxicity (ED$_{50}$ in $\mu$M) | | | | | | |
| 27 | O | $1.1 \times 10^{-2}$ | $1.5 \times 10^{-2}$ | $1.3 \times 10^{-2}$ | $1.2 \times 10^{-2}$ | $1.3 \times 10^{-2}$ | 72–73 | 7.4 ($\pm$0.4) |
| 28 | H, OH | 1.5 | 1.9 | 1.2 | 1.5 | 16.8 | 104–105 | >40 |
| 29 | H$_2$ | $1.5 \times 10^{-1}$ | $1.9 \times 10^{-2}$ | $1.3 \times 10^{-2}$ | $1.2 \times 10^{-2}$ | $1.3 \times 10^{-1}$ | 84–85 | 15 ($\pm$0.5) |

TABLE VII

| No. | A-549 | MCF-7 | HT-29 | SKMEL-5 | MLM | mp °C. | Inhibition of Tubulin Polymerization IC$_{50}$ ($\mu$M) ($\pm$S.D.) |
|---|---|---|---|---|---|---|---|
| | Cytotoxicity (ED$_{50}$ in $\mu$M) | | | | | | |
| 32a | 5.7 | 1.8 | 1.9 | 1.3 | 21.4 | — | >40 |
| 32b | >25 | >25 | 1.1 | 12.5 | >25 | 68–70 | >40 |
| 32c | >25 | >25 | >25 | >25 | >25 | 142–4 | >40 |
| 32d | >25 | 14.6 | 9.3 | 12.0 | >25 | 80–2 | >40 |
| 33 | 14.3 | >25 | 9.4 | 7.4 | >25 | — | >40 |
| 34 | >25 | >25 | >25 | >25 | >25 | 104–6 | >40 |
| 35 | >25 | >25 | 12.8 | 19.5 | >25 | — | >40 |
| 37 | 19.5 | >25 | 20.5 | 2.1 | >25 | 180–2 | >40 |
| 38 | 19.3 | >25 | 20.2 | >25 | >25 | — | >40 |
| 39 | >25 | >25 | >25 | >25 | >25 | — | >40 |
| 40 | >25 | >25 | >25 | >25 | >25 | — | >40 |
| 41 | 11.4 | 22.7 | 9.7 | 8.8 | >25 | — | >40 |
| 42 | >25 | >25 | >25 | >25 | >25 | 196–8 | >40 |
| 48 | >25 | >25 | >25 | >25 | >25 | 104–6 | >40 |

TABLE VIII

Effects of compounds 5a, 5b, 5e, 5f, 5g, 5h, 5n, 5p, 6a, 6n, 8a, 8n,12a, 12c, and 12d on tubulin polymerization and on the binding of radiolabeled colchicine to tubulin

| compd | Tubulin polymerization IC$_{50}$ ($\mu$M) ($\pm$S.D.) | Colchicine binding % inhibition |
|---|---|---|
| 5a | 2.2 ($\pm$0.07) | 95 |
| 5b | 8.8 ($\pm$1) | 50 |
| 5e | 3.5 ($\pm$0.3) | 73 |
| 5f | 36 ($\pm$1) | 14 |
| 5g | 4.8 ($\pm$0.3) | 55 |
| 5h | 3.1 ($\pm$0.1) | 73 |
| 5n | 3.4 ($\pm$0.1) | 83 |
| 5p | 29 ($\pm$5) | 24 |
| 6a | >50 | — |
| 6n | >50 | — |
| 8a | 7.9 ($\pm$0.8) | 65 |
| 8n | 29 ($\pm$1) | 31 |

TABLE VIII-continued

Effects of compounds 5a, 5b, 5e, 5f, 5g, 5h, 5n, 5p, 6a, 6n, 8a, 8n,12a, 12c, and 12d on tubulin polymerization and on the binding of radiolabeled colchicine to tubulin

| compd | Tubulin polymerization IC$_{50}$ (μM) (±S.D.) | Colchicine binding % inhibition |
|---|---|---|
| 12a | 23 (±0.5) | 34 |
| 12c | >50 | — |
| 12d | 29 (±2) | 39 |
| Combrestastatin A-4 (1a) | 1.9 (±0.2) | 99 |
| 1b | >50 | — |
| 1c | 3.3 (±0.2) | 79 |
| Podophyllotoxin | 2.1 (±0.1) | 88 |
| Thiocolchicine | 1.4 (±0.08) | 57 |

TABLE IX

| Compound No. | Inhibition of Tubulin Polymerization IC$_{50}$ (μM) (±SD) |
|---|---|
| 5a[a] | 2.5 (±0.1) |
| Combretastatin A-4[a] | 2.0 (±0.3) |
| 15a | 2.7 (±0.2) |
| 15b | 6.0 (±0.8) |
| 15c | 6.2 (±0.5) |
| 15d | 2.0 (±0.2) |
| 15e | 3.4 (±0.3) |
| 15f | 12 (±2) |
| 15g | >40 |
| 15h | 18 (±0.6) |
| 15i | 3.8 (±0.3) |
| 15j | >40 |
| 15k | >40 |
| 15l | 24 (±5) |
| 16a–16l | >40 |
| 17a | 10 (±1) |
| 17b | >40 |
| 17c | >40 |
| 17d | 21 (±3) |
| 17e | 18 (±1) |
| 17f | >40 |
| 17g | >40 |
| 17h | 11 (±0.4) |
| 17i | >40 |
| 17j | >40 |
| 23a–23c | >40 |
| 24a, b, d–f | >40 |
| 24c | 35 (±2) |
| 27 | 7.4 (±0.4) |
| 28 | >40 |
| 29 | 15 (±0.5) |
| 32a–32d | >40 |
| 33–35, 37–42, 48 | >40 |

[a]A second set of experiments was performed with these compounds for the studies presented in this Table.

TABLE X

Cytotoxicities and Antitibulin Activities of Schiff Bases, Benzylanilines, and Benzylaniline Hydrochlorides

| no. | cytotoxicity (GI$_{50}$ in μM)[a] | | | | | | | | inhibn of inbulin polymn IC$_{50}$ (μM) (±SD)[b] |
|---|---|---|---|---|---|---|---|---|---|
|  | HL-60(TB) | NCI-H522 | DMS 273 | COLO 205 | SF-295 | M14 | OVCAR-3 | CAKI-1 |  |
| 108b | 21.6 | >100 | >100 | 49.1 | >100 | >100 | >100 | >100 | >40 |
| 108c | 26.8 | >100 | 33.0 | 28.6 | 52.7 | 83.8 | >100 | >100 | >40 |
| 108d | >100 | >100 | >100 | 75.9 | >100 | >100 | >100 | >100 | >40 |
| 108f | >100 | >100 | 52.5 | >100 | >100 | >100 | >100 | >100 | >40 |
| 108g | 22.6 | >100 | >100 | >100 | >100 | >100 | >100 | >100 | >40 |
| 109a | 0.122 | 0.195 | 0.0926 | 0.152 | 0.163 | 0.150 | 0.184 | 0.192 | 6.0 (±0.6) |
| 109b | 0.168 | 0.234 | 0.135 | 0.344 | 0.266 | 0.315 | 0.283 | 0.354 | 3.0 (±0.4) |
| 109c | 0.115 | 0.412 | 0.141 | 0.235 | 0.266 | — | 0.363 | 0.458 | 4.6 (±0.6) |
| 109d | 0.296 | 0.380 | 0.296 | 0.432 | 0.274 | 0.403 | 0.340 | 2.04 | 12 (±1.0) |
| 109e | 3.70 | 4.68 | 3.09 | 3.88 | 7.28 | 5.26 | 5.93 | 32.0 | >40 |
| 110a | 0.0722 | 0.262 | 0.104 | 0.219 | 0.233 | 0.292 | 0.214 | 0.162 | 3.5 (±0.05) |
| 110b | 0.245 | 0.371 | 0.818 | 0.352 | 0.339 | 0.437 | 0.405 | — | 7.2 (±0.4) |
| 110c | 0.834 | 2.76 | 0.534 | 1.66 | 2.32 | 2.38 | 1.96 | 2.50 | 8.9 (±0.5) |
| 110d | 0.448 | 0.574 | 0.961 | 0.538 | 0.418 | 0.532 | 0.464 | 1.05 | 11 (±0.6) |
| 110e | 3.29 | 2.95 | 4.91 | 3.60 | 3.41 | 4.84 | 4.85 | 16.3 | 16 (±2) |
| 110f | 14.4 | 11.1 | 12.9 | 17.9 | 20.9 | 16.9 | 16.3 | 16.9 | >40 |
| 110g | 14.1 | 17.3 | 16.2 | 19.0 | 10.5 | 22.4 | 19.0 | — | >40 |

[a]The cytotoxicity GI$_{50}$ values are the concentrations corresponding to 50% growth inhibition, and they are the averages of two determinations.
[b]The tubulin polymerization assay used in the studies presented here employs 1M monosodium glutamate and GTP to induce the assembly reaction. Although the reaction conditions are identical in the current studies to those described earlier a different glutamate preparation was used. This modification has caused a reduction in all IC$_{50}$ values obtained with antimitotic compounds. The reason for the change is presently not known. Several standard agents were evaluated for comparison with the new compounds described here. The following IC$_{50}$ values were obtained: colchicine (A), 1.9 ± 0.2 um; podophyllotoxin (B), 1.3 ± 0.06 um; combretastatin A-4 (D), 1.0 ± 0.06 um; and compound E, 1.2 ± 0.05 um.

The IC$_{50}$ values of tubulin polymerization was determined as described in the text, with full details presented elsewhere. For the colchicine binding assay, reaction mixtures (in triplicate) contained 1 μM tubulin, 5 μM [$^3$H]colchicine, and 5 μM inhibitor and were incubated for 10 min at 37° C. prior to analysis.

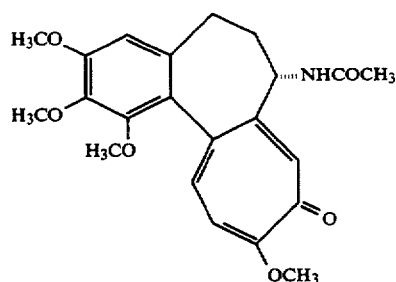

A

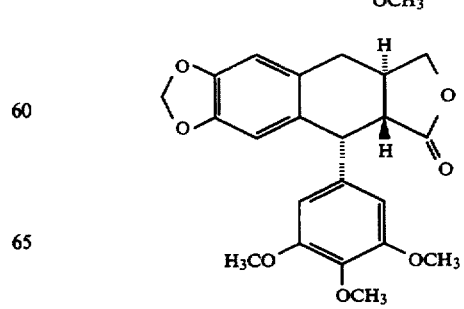

B

-continued

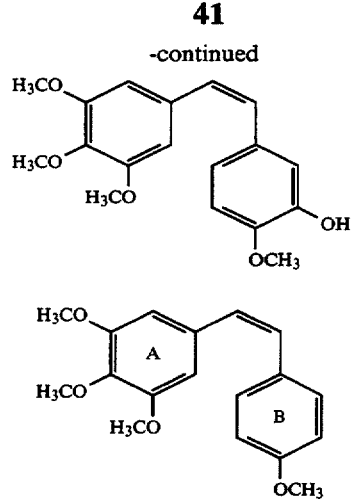

TABLE XI

Cytotoxicities of 4-Methyl-N-(3,4,5-trimethoxybenzyl)aniline hydrochloride (110a)

| Panel/Cell Line | $Log_{10}$ $GI_{50}$ |
|---|---|
| Leukemia | |
| CCRF-CBM | −6.55 |
| HL-60 (TB) | −7.05 |
| K-562 | −7.00 |
| MOLT-4 | −6.37 |
| RPMI-8226 | −6.36 |
| Non-Small Cell Lung Cancer | |
| A549/ATCC | −6.29 |
| EKCK | −6.13 |
| HOP-18 | −4.43 |
| HOP-62 | −6.55 |
| HOP-92 | −4.73 |
| NCI-H23 | −6.39 |
| NCI-H322M | −6.30 |
| NCI-H460 | −6.67 |
| NCI-H522 | −6.69 |
| LXFL 529 | −6.20 |
| Small Cell Lung Cancer | |
| DMS114 | −6.37 |
| DMS 273 | −7.03 |
| Colon Cancer | |
| COLO 205 | −6.67 |
| DLD-1 | −6.24 |
| HCT-116 | −6.24 |
| HCT-15 | −6.61 |
| HT29 | −6.46 |
| KM12 | −6.12 |
| KM20L2 | −6.60 |
| SW-620 | −6.96 |
| CNS Cancer | |
| SF-268 | −6.04 |
| SF-295 | −6.49 |
| SF-539 | −6.50 |
| SNB-19 | −6.53 |
| SNB-75 | −6.41 |
| SNB-78 | −5.96 |
| U251 | −6.48 |
| XF498 | −6.33 |
| Melanoma | |
| LOX IMVI | −6.07 |
| MALME-3M | −6.33 |
| M14 | <−8.00 |
| M19-MEL | −6.48 |
| SK-MEL-2 | −6.88 |
| SK-MEL-5 | −6.04 |
| UACC-257 | >−4.00 |
| UACC-62 | −6.24 |
| Ovarian Cancer | |
| IGROVI | −6.15 |
| OVCAR-3 | −6.71 |
| OVCAR-4 | −4.67 |
| OVCAR-5 | −5.87 |

TABLE XI-continued

Cytotoxicities of 4-Methyl-N-(3,4,5-trimethoxybenzyl)aniline hydrochloride (110a)

| Panel/Cell Line | $Log_{10}$ $GI_{50}$ |
|---|---|
| OVCAR-8 | −6.12 |
| SK-OV-3 | −6.57 |
| Renal Cancer | |
| 786-0 | −6.49 |
| A498 | >−4.00 |
| ACHN | −7.01 |
| CAKI-1 | −7.88 |
| RXF-393 | −6.95 |
| SN12C | −6.07 |
| TK-10 | >−4.00 |
| UO-31 | −6.08 |

Other benzylanilines have also been tested. The results are indicated in Table X. More specifically, the effects on cell growth and tubulin polymerization of five Schiff bases 108, five amines 109, and seven hydrochlorides 110 are summarized in Table X. These compounds were examined for cytotoxicity in the human cancer cell lines HL-60 (TB) leukemia, NCI-H522 non-small cell lung cancer, DMS 273 small cell lung cancer, COLO 205 colon cancer, SF-295 CNS cancer, M14 melanoma, OVCAR-3 ovarian cancer, and CAKI-1 renal cancer using the assays described hereinabove. Inhibitor of tubulin polymerization was examined using electrophoretically homogeneous tubulin from bovine brain, using the assays described hereinabove.

With the amines 109a–e and the corresponding hydrochloride salts 110a–g, potency as a tubulin polymerization inhibitor inversely correlated with the size of the R substituent in the C-4 position of the aniline ring. The smaller the substituent, the higher the potency. Among the highly soluble hydrochloride salts, 4-methyl-N-(3,4,5-trimethoxybenzyl)aniline hydrochloride (110a) was the most potent of the compounds studied ($IC_{50}$ 3.5 μm). The 4-ethyl (110b, $IC_{50}$ 7.2 μm), 4-methoxy (110c, 8.9 μm), 4-ethoxy (110d, 11.0 μm), and 4-thiomethyl (110e, 16.0 μm) analogues had less activity. This trend between the potencies of the compounds as tubulin polymerization inhibitors and the size of the aniline substituent R was reflected remarkably well by the cytotoxicities in all of the cancer cell cultures studied. The smaller the substituent, the higher the cytotoxicity. These relationships generally held for the corresponding free bases 109a–e, except that the compound with the ethyl substituent (109b) was more effective ($IC_{50}$ 3.0 μm) against tubulin polymerization than the analog with the methyl substituent (109a, $IC_{50}$ 6.0 μm).

A more extensive analysis of the cytotoxicities of the most potent benzylaniline hydrochloride 110a is detailed in Table XI. A total of 55 cell lines from the leukemia, non-small cell lung cancer, small cell lung cancer, colon cancer, CNS cancer, melanoma, ovarian cancer, and renal cancer panels were examined. As can be seen from the results in Table XI, the cytotoxicity was broad in scope, although 110a was clearly most cytotoxic ($log_{10}$ $GI_{50}$ < −7.00) in the HL-60 (TB) leukemia, K-562 leukemia, DMS 273 small cell lung cancer, M14 melanoma, ACHN renal cancer, and CAKI-1 renal cancer cell cultures. It therefore appears that benzylaniline hydrochloride salt 110a is an uncommonly simple, water soluble tubulin polymerization inhibitor which is cytotoxic to a variety of animal cancer models.

Without wishing to be bound to any mechanism, the compounds encompassed in Formula I have been determined to be effective inhibitors of tubulin polymerization. In other words, the compounds of the present invention interact effectively with the colchicine binding site of tubulin thus they represent potential antimitotic agents which may inhibit cancer cell proliferation.

Pharmaceutical Formulations

The present new compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluene-sulfonic, acetic, maleic, tartaric and the like which are pharmaceutically acceptable. Basic salts for pharmaceutical use are the Na, K, Ca and Mg salts, and the like.

The pharmaceutical compositions of the present invention comprise the compounds encompassed by Formula I and an acceptable pharmaceutical carrier. The carrier can be any of those conventionally used and is limited only by chemico-physical considerations such as solubility and lack of reactivity with the compound and by the route of administration.

For intravenous administration, the carrier will be aqueous and may contain solubilizing agents, buffers, preservatives, antioxidants, chelating agents, and agents to control the tonicity, such as dextrose or sodium chloride. The requirements for effective pharmaceutical carriers for injectable compositions are well known to one of ordinary skill in this art. (See "Pharmaceutics and Pharmacy Practice", J. B. Lippincott Company, Philadelphia, 1982, edited by Banker and Chalmers, pages 238-250, which are incorporated by reference, also see ASHP "Handbook of Injectable Drugs" 4th Edition by Trissel, pages 622-630, which lists commercially available intravenous infusion solutions, these pages are incorporated by reference.)

The active ingredients of the therapeutic compositions and the compounds of the present invention exhibit excellent anti-cancer activity when administered in amounts ranging from about 0.001 mg to about 10.0 mg per kilogram of body weight per day. A preferred dosage regimen for optimum results would be from about 0.01 mg to about 10 mg per kilogram of body weight per day, and such dosage units are employed that a total of from about 0.1 mg to about 1.0 mg per kilogram of the active compound for a subject of about 70 kg of body weight are administered in a 24-hour period in single or divided doses. This dosage regimen may be adjusted to provide the optimum therapeutic response and is preferably administered one to three times a day. For example, several divided doses may be administered daily or the dose may be proportionally reduced as indicated by the exigencies of the therapeutic situation. A decided practical advantage is that the active compound may be administered in a convenient manner such as by the oral, intravenous (where water soluble), intramuscular or subcutaneous routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between 5 and 1000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, but the use of a coating such as lecithin; by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effect administration in effective amounts with a suitable pharmaceutically acceptable carrier in dosage unit form as hereinbefore disclosed. A unit dosage form can, for example, contain the principal active compound in amounts ranging from about 5 to about 1000 mg, with from about 5 to about 250 mg being preferred. In the case of compositions containing supplementary active ingredients, the dosages are determined by reference to the usual dose and manner of administration of the said ingredients.

For a better understanding of the present invention together with other and further objects, reference is made to the following description and examples.
Experimental Section—Compound Preparation Melting points were determined in capillary tubes on a Mel-Temp apparatus and are uncorrected. Spectra were obtained as follows: CI mass spectra on a Finnegan 4000 spectrometer; $^1$H NMR spectra on a Chemagnetics A-200 or Nicolet QE-300 or Varian VXR-500S spectrometers with TMS as an internal standard in CDCl$_3$ or DMSO-d$_6$; IR spectra were obtained on a Beckman IR-33 spectrophotometer. Microanalyses were performed at the Purdue Microanalysis Laboratory, and all values were within ±0.4% of the calculated composition. All organic solvents were appropriately dried and/or purified prior to use. Diethyl benzylphosphonate 7a, aryl aldehydes 4a-t and 1M solution of tetra-n-butylammonium fluoride in THF were obtained from commercial sources. Compounds 7b-c were prepared by the reaction of the corresponding benzyl bromides and triethyl phosphite. Phosphonium bromides 3a-b were prepared by stirring a mixture of triphenyl phosphine and the corresponding benzyl bromides in toluene. Combretastatin A-4 and its trans isomer were obtained from Prof. G. R. Pettit, Arizona State University. Compound 1c was prepared as described previously. Podophyllotoxin was obtained from Aldrich Chemical Co., and thiocolchicine was from Roussel-Uclaf. Preparative silica gel tlc plates (200 micron) were purchased from Analtech.

General procedure for the preparation of Z-Stilbenes 5a-n and E-Stilbenes 6a-n. Sodium hydride (72 mg, 3 mmol) was added in portions to a well-stirred suspension of phosphonium bromide 3a-b (2.0 mmol) and aryl aldehyde (2.0 mmol) in benzene (20 mL) under argon atmosphere at 0°-5° C., and the mixture was allowed to warm to room temperature. After an additional stirring for 16 h, excess sodium hydride was quenched by the addition of methanol (1 mL). Solvents from the reaction mixture were evaporated at reduced pressure, and the residue was purified by preparative thin layer chromatography using 5% EtOAc in hexane as the eluent. Products 5d and 5l were obtained as solids, and all the other cis stilbenes were obtained as viscous oils.

(Z)-1-(4-Methoxyphenyl)-2-(3,4,5-trimethoxyphenyl)ethene (5a): 400 mg; 66%; oil: $^1$H NMR (CDCl$_3$, 500 MHz) δ7.25 (d, J=9 Hz, 2H), 6.80 (d, J=9 Hz, 2H), 6.53 (d, J=12 Hz, 1H), 6.51 (s, 2H), 6.44 (d, J=12 Hz, 1H), 3.84 (s, 3H), 3.79 (s, 3H), 3.69 (s, 6H); CIMS (isobutane) m/e 301 (MH$^+$, 100). Anal. (C$_{18}$H$_{20}$O$_4$) C, H.

(Z)-1-(3-Methoxyphenyl)-2-(3,4,5-trimethoxyphenyl)ethene (5b): 410 mg; 69%; oil; $^1$H NMR (CDCl$_3$, 200 MHz) δ7.18 (t, J=7.9 Hz, 1H), 6.91-6.83 (m, 2H), 6.78-6.72 (m, 1H), 6.58 (d, J=12.2 Hz, 1H), 6.50 (d, J=12.2 Hz, 1H), 6.49 (s, 2H), 3.83 (s, 3H), 3.70 (s, 3H), 3.67 (s, 6H); $^{13}$C NMR (CDCl$_3$, 50 MHz) δ159.94, 153.29, 139.63, 137.63, 132.84, 130.67, 130.22, 129.63, 121.79, 114.24, 113.46, 106.42, 61.06, 56.01, 55.26; CIMS (isobutane) m/e 301 (MH$^+$, 100). Anal. (C$_{18}$H$_{20}$O$_4$) C, H.

(Z)-1-(2-Methoxyphenyl)-2-(3,4,5-trimethoxyphenyl)ethene (5c): 440 mg; 73%; oil: $^1$H NMR (CDCl$_3$, 500 MHz) δ7.27-7.20 (m, 2H), 6.90 (d, J=8.4 Hz, 1H), 6.82 (t, J=8.4 Hz, 1H), 6.65 (d, J=12.2 Hz, 1H), 6.54 (d, J=12.2 Hz, 1H), 6.47 (s, 2H), 3.84 (s, 3H), 3.82 (s, 3H), 3.63 (s, 6H); CIMS (isobutane) m/e 301 (MH$^+$, 100). Anal. (C$_{18}$H$_{20}$O$_4$) C, H.

(Z)-1-(4-Methoxyphenyl)-2-(2,3,4-trimethoxyphenyl)ethene (5d): 460 mg; 77%; mp 55°-7° C.; $^1$H NMR (CDCl$_3$, 200 MHz) δ7.19 (d, J=8.9 Hz, 2H), 6.94 (d, J=8.7 Hz, 1H), 6.75 (d, J=8.9 Hz, 2H), 6.52 (s, 2H), 6.49 (d, J=8.7 Hz, 1H), 3.90 (s, 3H), 3.88 (s, 3H), 3.84 (s, 3H), 3.78 (s, 3H); CIMS (isobutane) m/e 301 (MH$^+$, 100). Anal. (C$_{18}$H$_{20}$O$_4$) C, H.

(Z)-1-(2-Chloro-4-methoxyphenyl)-2-(2,3,4-trimethoxyphenyl)ethene (5e): 420 mg; 63%; oil; $^1$H NMR (CDCl$_3$, 500 MHz) δ7.21 (d, J=8.5 Hz, 1H), 6.96 (d, J=2.6 Hz, 1H), 6.67 (dd, 1H), 6.59 (d, J=12.1 Hz, 1H), 6.57 (d, J=12.1 Hz, 1H), 6.42 (s, 2H), 3.82 (s, 3H), 3.78 (s, 3H), 3.66 (s, 6H). Anal. (C$_{18}$H$_{19}$ClO$_4$) C, H.

(Z)-1-Phenyl-2-(3,4,5-trimethoxyphenyl)ethene (5f): 270 mg; 50%; oil; $^1$H NMR (CDCl$_3$, 200 MHz)

δ7.35–7.25 (m, 5H), 6.61 (d, J=12.2 Hz, 1H), 6.50 (d, J=12.2 Hz, 1H), 6.47 (s, 2H), 3.83 (s, 3H), 3.65 (s, 6H); $^{13}$C NMR (CDCl$_3$, 50 MHz) δ153.27, 137.86, 137.12, 132.84, 130.48, 130.36, 129.28, 128.62, 127.51, 106.35, 61.09, 55.96; CIMS (isobutane) m/e 271 (MH$^+$, 100). Anal. (C$_{17}$H$_{18}$O$_3$) C, H.

(Z)-1-(4-Chlorophenyl)-2-(3,4,5-trimethoxyphenyl)ethene (5g): 7 mg; 50%; oil; $^1$H NMR (CDCl$_3$, 200 MHz) δ7.23, (s, 4H), 6.55 (d, J=12 Hz, H), 6.49 (d, J=12 Hz, 1H), 6.45 (s, 2H), 3.84 (s, 3H), 3.68 (s, 6H); $^{13}$C NMR (CDCl$_3$, 50 MHz) δ153.43, 137.77, 136.17, 133.19, 132.53, 131.20, 130.74, 128.96, 128.75, 106.26, 61.10, 56.05; Anal. (C$_{17}$H$_{17}$ClO$_3$) C, H.

(Z)-1-(4-Bromophenyl)-2-(3,4,5-trimethoxyphenyl)ethene (5h): 363 mg; 52%; oil; $^1$H NMR (CDCl$_3$, 200 MHz) δ7.38 (d, J=8.6 Hz, 2H), 7.16 (d, J=8.6 Hz, 2H), 6.56 (d, J=12.1 Hz, 1H), 6.47 (d, J=12.1 Hz, 1H), 6.44 (s, 2H), 3.84 (s, 3H), 3.68 (s, 6H); $^{13}$C NMR (CDCl$_3$, 50 MHz) δ153.42, 137.77, 136.63, 132.49, 131.71, 131.28, 131.02, 128.98, 121.29, 106.25, 61.09, 56.05; CIMS (isobutane) m/e 350 (93) 348 (MH$^+$, 100). Anal. (C$_{17}$H$_{17}$BrO$_3$) C, H.

(Z)-1-(4-Pyridyl)-2-(3,4,5-trimethoxyphenyl)ethene (5i): 277 mg; 51%; oil; $^1$H NMR (CDCl$_3$, 500 MHz) δ8.49 (d, J=6.0 Hz, 2H), 7.18 (d, J=6.0 Hz, 2H), 6.69 (d, J=12.2 Hz, 1H), 6.48 (d, J=12.2 Hz, 1H), 6.42 (s, 2H), 3.84 (s, 3H), 3.66 (s, 6H); CIMS (isobutane) m/e 272 (MH$^+$, 100). Anal. (C$_{16}$H$_{17}$NO$_3$) C, H.

(Z)-1-(3-Pyridyl)-2-(3,4,5-trimethoxyphenyl)ethene (5j): 292 mg; 54%; oil; $^1$H NMR (CDCl$_3$, 500 MHz) δ8.53 (s, 1H), 8.43 (d, J=4.8 Hz, 1H), 7.60 (d, J=7.9 Hz, 1H), 7.18 (dd, J$_1$=4.8 Hz, J$_2$=7.9 Hz, 1H), 6.67 (d=12.2 Hz, 1H), 6.53 (d, J=12.2 Hz, 1H), 6.41 (s, 2H), 3.84 (s, 3H), 3.67 (s, 6H); CIMS (isobutane) m/e 272 (MH$^+$, 100). Anal. (C$_{16}$H$_{17}$NO$_3$) C, H.

(Z)-1-(2-Pyridyl)-2-(3,4,5-trimethoxyphenyl)ethene (5k): 351 mg; 65%; oil; $^1$H NMR (CDCl$_3$, 500 MHz) d 8.64 (d, J=4.7 Hz, 1H), 7.58–7.54 (dt, J$_1$=7.5 Hz, J$_2$=1.8 Hz, 1H), 7.32–7.30 (m, 1H), 7.17–7.15 (m, 2H), 6.79 (d, J=12.4 Hz, 1H), 6.58 (s, 2H), 3.89 (s, 3H), 3.74 (s, 6H); CIMS (isobutane) m/e 272 (MH$^+$, 100). Anal. (C$_{16}$H$_{17}$NO$_3$) C, H.

(Z)-1-(4-Nitrophenyl)-2-(3,4,5-trimethoxyphenyl)ethene (5l): 170 mg; 27%; mp 140°–142° C.; $^1$H NMR (CDCl$_3$, 300 MHz) δ8.15 (d, J=8.6 Hz, 2H), 7.56 (d, J=8.6 Hz, 2H), 7.05 (d, J=12 Hz, 1H), 6.95 (d, J=12 Hz, 1H), 6.71 (s, 2H), 3.86 (s, 6H), 3.82 (s, 3H); CIMS (isobutane) m/e 316 (MH$^+$, 100). Anal. (C$_{17}$H$_{17}$NO$_5$) C, H.

(Z)-1-[(4-t-Butyldimethylsilyloxy)phenyl]-2-(3,4,5-trimethoxyphenyl)ethene (5m): 429 mg; 53%; oil; IR (Neat) 2980, 2960, 1610, 1580, 1520, 1470, 1420, 1360, 1330, 1270, 1140 cm$^{-1}$; $^1$H NMR (CDCl$_3$, 300 MHz) d 7.17 (d, J=8.0 Hz, 2H), 6.73 (d, J=8.0 Hz, 2H), 6.51 (s, 2H), 6.41 (s, 2H), 3.84 (s, 3H), 3.79 (s, 6H), 0.99 (s, 9H), 0.14 (s, 6H). Anal. (C$_{23}$H$_{32}$O$_4$Si) C, H.

(Z)-1-[4-(N,N-Dimethylamino)phenyl]-2-(3,4,5-trimethoxyphenyl)ethene (5n): 450 mg; 72%; oil; $^1$H NMR (CDCl$_3$, 500 MHz) δ7.22 (d, J=8.9 Hz, 2H), 6.61 (d, J=8.9 Hz, 2H), 6.58 (s, 2H), 6.41 (d, J=12.1 Hz, 1H), 6.34 (d, J=12.1 Hz, 1H), 3.85 (s, 3H), 3.72 (s, 6H), 2.93 (s, 6H); CIMS (isobutane) m/e 314 (MH$^+$, 100). Anal. (C$_{19}$H$_{23}$NO$_3$) C, H.

(E)-1-(4-Methoxyphenyl)-2-(3,4,5-trimethoxyphenyl)ethene (6a): 67 mg; 11%; mp 152°–5° C.; $^1$H NMR (CDCl$_3$, 500 MHz) δ7.45 (d, J=8.5 Hz, 2H), 6.97 (d, J=16.0 Hz, 1H), 6.91 (d, J=16.0 Hz, 1H), 6.90 (d, J=8.5 Hz, 2H), 6.72 (s, 2H), 3.87 (s, 3H), 3.84 (s, 3H), 3.82 (s, 3H); CIMS (isobutane) m/e 301 MH$^+$, 100). Anal. (C$_{18}$H$_{20}$O$_4$) C, H.

(E)-1-(4-Nitrophenyl)-2-(3,4,5-trimethoxyphenyl)ethene (6l): 280 mg; 44%; mp 192°–4° C.

(E)-1-[(4-t-Butyldimethylsilyloxy)phenyl]-2-(3,4,5-trimethoxyphenyl)ethene (6m): 218 mg; 27%; oil; IR (Neat) 2980, 2960, 1605, 1585, 1520, 1470, 1420, 1340, 1320, 1270, 1170, 1130, 1010 cm$^{-1}$; $^1$H NMR (CDCl$_3$, 300 MHz) δ6.89 (d, J=16.5 Hz, 1H), 6.81 (d, J=16.5 Hz, 1H), 7.31 (d, J=8.5 Hz, 2H), 6.76 (d, J=8.5 Hz, 2H), 6.64 (s, 2H), 3.84 (s, 3H), 3.79 (s, 6H), 0.92 (s, 9H), 0.14 (s, 6H). Anal. (C$_{23}$H$_{32}$O$_4$Si) C, H.

(E)-1-[4-(N,N-Dimethylamino)phenyl]-2-(3,4,5-trimethoxyphenyl)ethene (6n): 145 mg; 23%; mp 114°–5° C.; IR (KBr) 3000, 2980, 2940, 2860, 1600, 1580, 1520, 1340, 1240, 1120, 960 cm$^{-1}$; $^1$H NMR (DMSO-d$_6$, 500 MHz) δ7.42 (d, J=8.85 Hz, 2H), 7.10 (d, J=16.3 Hz, 1H), 6.92 (d, J=16.3 Hz, 1H), 6.86 (d, J=8.8 Hz, 2H), 6.61 (s, 2H), 3.83 (s, 6H), 3.67 (s, 3H), 2.94 (s, 6H); CIMS (isobutane) m/e 314 (MH$^+$, 100), 313 (72). Anal. C$_{19}$H$_{23}$NO$_3$) C, H.

(Z)-1-(4-Hydroxyphenyl)-2-(3,4,5-trimethoxyphenyl)ethene (5o): A solution of N-Bu$_4$NF in THF (1M, 2 mL, 2 mmol) was added to a stirred solution of silyl ether 5 m (372 mg, 1 mmol) in THF (5 mL) at room temperature and the stirring was continued for 30 min. Solvent was removed at reduced pressure, the resulting residue was treated with 20 mL of water and the product was extracted with EtOAc (2×20 mL). The EtOAc solution was dried (MgSO$_4$), concentrated and the residue was crystallized from EtOAc/hexane to give 5n (217 mg, 76%); mp 148°–150° C.; IR (KBr) 3440, 3020, 2940, 2840, 1610, 1580, 1510, 1420, 1330, 1230, 1160, 1120, 980, 790, 750 cm$^{-1}$; $^1$H NMR (CDCl$_3$, 200 MHz) δ7.40 (bs, 1H), 7.24 (d, J=8.1 Hz, 2H), 7.10 (d, J=8.1 Hz, 2H), 6.60–6.30 (m, 4H), 3.80 (s, 6H), 3.76 (s, 3H); CIMS (isobutane m/e 287 (MH$^+$, 100). Anal. (C$_{17}$H$_{18}$O$_4$) C, H.

(E)-1-(4-Hydroxyphenyl)-2-(3,4,5-trimethoxyphenyl)ethene (6o): Using the same procedure described for 5o, compound 6o was prepared from 6 m in 1 mmol scale (228 mg, 80%); mp 188°–90° C.

General procedure for the preparation of acetates (5p & 6p): A solution of n-Bu$_4$NF in THF (1M, 2 mL, 2 mmol) was added to a solution of stilbenes 5m/6m (400 mg, 1 mmol) in THF (5 mL) and the mixture was stirred at 0° C. After 30 min., acetic anhydride (0.5 mL) was added, and the stirring was continued at room temperature for 24 h. Solvents were evaporated at reduced pressure, and the residue was mixed with water (50 mL). The product was extracted with ether (2×25 mL), and the ether solution was washed with water (2×100 mL). Evaporation of the solvents and purification of the crude product by preparative TLC using 40% ethyl acetate in hexanes as the eluent afforded the desired products.

(Z)-1-(4-Acetoxyphenyl)-2-(3,4,5-trimethoxyphenyl)ethene (5p): 93 mg; 28%; oil; $^1$H NMR (CDCl$_3$, 500 MHz) δ7.30 (d, J=8.3 Hz, 2H), 6.98 (d, J=8.3 Hz, 2H), 6.57 (d, J=12.1 Hz, 1H), 6.47 (d, J=12.1 Hz, 1H), 6.45 (s, 2H), 3.83 (s, 3H), 3.67 (s, 6H), 2.29 (s, 3H); CIMS (isobutane) m/e 329 (MH$^+$, 100). Anal. (C$_{19}$H$_{20}$O$_5$) C, H.

(E)-1-(4-Acetoxyphenyl)-2-(3,4,5-trimethoxyphenyl)ethene (6p): 114 mg; 34%; oil; $^1$H NMR (CDCl$_3$, 500 MHz) δ7.51 (d, J=8.7 Hz, 2H), 7.09 (d, J=8.7 Hz, 2H), 6.99 (s, 2H), 6.73 (s, 2H), 3.92 (s, 6H), 3.87 (s, 3H), 2.31 (s, 3H); CIMS (isobutane) m/e 329 (MH+, 100). Anal. $C_{19}H_{20}O_5$) C, H.

General procedure for the preparation of 6q–y: A solution of phosphonate esters 7a–c (12 mmol) in dry DMF (10 mL) was added to a magnetically stirred solution of NaOMe (0.65 g, 12 mmol) in dry DMF (10 mL) at 0° C. and the solution was stirred for 30 min. A solution of aldehyde 4d/4o–t (10 mmol) in dry DMF (10 mL) was added at 0° C., and the reaction mixture was allowed to warm to room temperature over a period of 1.5 h. The mixture was heated at 95°–100° C. for 1 h and left overnight at room temperature. The mixture was poured slowly onto crushed ice, and the precipitated solid was filtered, washed with water, dried and crystallized from EtOAc-hexane.

(E)-1-(3,4-Dimethoxyphenyl)-2-phenylethene (6q): 1.64 g; 68%; mp 106°–8° C.

(E)-1-Phenyl-2-(2,3,4-trimethoxyphenyl)ethene (6r): 2.34 g; 87%; mp 79°–82° C.; IR (KBr) 3020, 3000, 2980, 2940, 2840, 1600, 1510, 1470, 1420, 1300, 1260, 1230, 1090, 1030, 1000, 980 cm$^{-1}$; $^1$H NMR (CDCl$_3$, 500 MHz) $\delta$7.60–7.50 (m, 2H), 7.40–7.20 (m, 5H), 6.9 (d, J=60.5 Hz, 1H), 6.70 (d, J=16.5 Hz, 1H), 3.91 (s, 3H), 3.90 (s, 3H), 3.89 (s, 3H); CIMS (isobutane) m/e 271 (MH+, 100). Anal. ($C_{17}H_{18}O_3$) C, H.

(E)-1-(4-Aminophenyl)-2-(3,4,5-trimethoxyphenyl)ethene (6z): Lithium aluminum hydride (76 mg, 2 mmol) was added to a solution of nitro stilbene 6l (270 mg, 0.87 mmol) in THF (25 mL), and the mixture was stirred at room temperature for 12 h. Solvent was evaporated at reduced pressure, and the residue was decomposed by careful addition of ice water (20 mL) containing 2 mL of glacial acetic acid. The red solid formed was filtered and crystallized from CH$_2$Cl$_2$-ether to give 6z (200 mg, 82%); mp 251°–3° C.; IR (KBr) 3440, 3400, 3000, 2920, 2820, 1600, 1580, 1510, 1340, 1240, 1130, 990, 950, 830 cm$^{-1}$; $^1$H NMR (DMSO-d$_6$, 300 MHz) $\delta$7.87 (d, J=8.3 Hz, 2H), 7.59 (d, J=8.3 Hz, 2H), 7.08 (d, J-16.0 Hz, 1H), 7.01 (d, J=16.0 Hz, 1H), 6.71 (s, 2H), 3.87 (s, 6H), 3 82 (s, 3H); CIMS (isobutane) m/e 286 (MH+, 100). Anal. ($C_{17}H_{19}NO_3$) C, H.

General procedure for the preparation of dihydrostilbenes 8. A solution of stilbene 5 and 6 (1 mmol) in EtOAc (25 mL) was hydrogenated at 40 psi in the presence of 10% Pd-C (30 mg) until the uptake of hydrogen ceased (4h). The solution was filtered and concentrated to obtain the dihydrostilbenes 8 almost as single components.

1-(4-Methoxyphenyl)-2-(3,4,5-trimethoxyphenyl)ethane (8a): 280 mg; 93%; mp 73°–5° C.; $^1$H NMR (CDCl$_3$, 500 MHz) $\delta$7.10 (d, J=8.5 Hz, 2H), 6.83 (d, J=8.5 Hz, 2H), 6.36 (s, 2H), 3.83 (s, 3H), 3.82 (s, 6H), 3.79 (s, 3H), 2.80–2.90 (m, 4H); $^{13}$C NMR (CDCl$_3$, 50 MHz) $\delta$158.53, 153.62, 138.16, 136.68, 134.23, 129.96, 114.22, 105.88, 61.16, 56.31, 55.52, 38.85, 37.33; CIMS (isobutane) m/e 303 (MH+, 100). Anal. ($C_{18}H_{22}O_4$) C, H.

1-[4-(Dimethylamino)phenyl]-2-(3,4,5-trimethoxyphenyl)ethane (8n): 265 mg; 84%; oil; $^1$H NMR (CDCl$_3$, 500 MHz) $\delta$7.08 (d, J=8.7 Hz, 2H), 6.72 (d, J=8.7 Hz, 2H), 6.38 (s, 2H), 3.85 (s, 3H), 3.83 (s, 6H), 2.92 (s, 4H), 2.82 (s, 6H); CIMS (isobutane) m/e 316 (MH+, 100%). Anal. ($C_{19}H_{25}NO_3$) C, H.

1-(4-Aminophenyl)-2-(3,4,5-trimethoxyphenyl)ethane (8z): A solution of nitrostilbene 6l (250 mg, 0.8 mmol) in EtOAc (20 mL) was hydrogenated at 30 psi in the presence of 10% Pd-C (25 mg) at room temperature for 4 h, and the catalyst was filtered off. Evaporation of the solvent and crystallization of the residue from hexanes gave the amine 8z (180 mg, 80%); mp 84°–5° C; IR (KBr) 3450, 3400, 3020, 2920, 2840, 1600, 1580, 1520, 1330, 1240, 1120, 980 cm$^{-1}$; $^1$H NMR (CDCl$_3$, 300 MHz) d 6.98 (d, J=8.2 Hz, 2H), 6.63 (d, J=8.2 Hz, 2H), 6.63 (d, J=8.2 Hz, 2H), 6.37 (s, 2H), 3.83 (s, 9H), 3.57 (bs, 2H), 2.80 (s, 4H); CIMS (isobutane) m/e 288 (MH+, 100). Anal. ($C_{17}H_{21}NO_3$) C, H.

1-(4-Acetamidophenyl)-2-(3,4,5-trimethoxyphenyl)ethane (8m): The amine 8z (0.574 g, 2 mmol) was dissolved in dry benzene (10 mL) containing triethylamine (0.5 mL) and cooled to 0° C. Acetyl chloride (320 mg, 4 mmol) was added dropwise, and the solution was stirred for 30 min. The contents were poured into ice cold water, and the mixture was extracted with ether (25 mL). The organic layer was washed with water, 5% sodiumbicarbonate solution, and dried (MgSO$_4$) and the solvent was evaporated. The residue was crystallized from EtOAc-hexane (0.52 g, 79%); mp 112°–4° C.; IR (KBr) 3450, 3000, 2930, 2840, 1670, 1600, 1580, 1510, 1340, 1120 cm$^{-1}$; $^1$H NMR (CDCl$_3$, 200 MHz) $\delta$7.52 (bs, 1H), 7.42 (d, J=8.4 Hz, 2H), 7.11 (d, J=8.4 Hz, 2H), 6.36 (s, 2H), 3.82, (s, 3H), 3.81 (s, 6H), 2.85 (s, 4H), 2.14 (s, 3H); CIMS (isobutane) m/e 330 (MH+, 100). Anal. ($C_{19}H_{23}NO_4$) C, H.

General procedure for preparation of Benzamides 11a–f. Aroyl chloride 9a–d (20 mmol) was added to a stirred solution of substituted aniline 10a–c (20 mmol) in pyridine (50 mL) at room temperature, and the reaction mixture was stirred for 4 h and poured into a mixture of ice (400 g) and hydrochloric acid (100 mL). The precipitated product was filtered, washed with water, dried and recrystallized from CHCl$_3$-hexane.

3,4,5-Trimethoxy-N-(4-methoxyphenyl)benzamide (11a): 5.83 g; 92%; mp 160°–161° C.; $^1$H NMR (CDCl$_3$, 500 MHz) $\delta$8.22 (bs, 1H), 7.50 (d, J=8.1 Hz, 2H), 7.03 (s, 2H), 6.83 (d, J=8.1 Hz, 2H), 3.85 (s, 3H), 3.80 (s, 6H), 3.77 (s, 3H); CIMS (isobutane) m/e 318 (MH+, 100).

4-Methoxy-N-(3,4,5-trimethoxyphenyl)benzamide (11c): 5.60 g; 88%; mp 159°–160° C.; IR (KBr) 3300, 2980, 2940 1650, 1605, 1515, 1455, 1420, 1340, 1270, 1220, 1020, 1000 cm$^{-1}$; $^1$H NMR (CDCl$_3$, 500 MHz) $\delta$8.18 (bs, 1H), 7.60 (d, J=8.0 Hz, 2H), 6.90 (s, 2H), 6.88 (d, J=8.0 Hz, 2H), 3.92 (s, 3H), 3.80 (s, 6H), 3.76 (s, 3H); CIMS (isobutane) m/e 318 (MH+, 100). Anal. ($C_{17}H_{19}NO_5$) C, H.

General procedure for preparation of N-benzylanilines 12a–f. A solution of benzamide 11a–f (5 mmol) in THF (50 mL) was added to a well-stirred suspension of lithium aluminum hydride (0.285 g, 7.5 mmol) in dry THF (10 mL) at 0° C. under nitrogen atmosphere, and the reaction mixture was allowed to warm to room temperature. After 4 h, the reaction mixture was poured onto ice (200 g), and the mixture was extracted with ether (3×20 mL). The combined extracts were washed with water and dried (K$_2$CO$_3$). Evaporation of ether from the solution afforded amines 12a–f almost as single products. Analytical samples of solid products were prepared by crystallization from ether-hexane, and liquids were purified by preparative thin-layer chromatography using 2% methanol in CHCl$_3$ as eluent.

3,4,5-Trimethoxy-N-(4-methoxyphenyl)benzylamine (12a): 1.42 g; 94%; mp 73°–4° C.; IR (KBr) 3400, 2990, 2920, 2220, 1600, 1510, 1460, 1420, 1330, 1260, 1230, 1120, 1110, 1030, 1000 cm$^{-1}$; $^1$H NMR (CDCl$_3$, 500 MHz) $\delta$6.78 (d, J=8.6 Hz, 2H), 6.62 (d, J=8.6 Hz, 2H), 6.61 (s, 2H), 4.21 (s, 2H), 3.86 (bs, 1H), 3.84 (s, 9H), 3.74 (s, 3H); $^{13}$C NMR (CDCl$_3$, 50 MHz) $\delta$153.98, 152.88, 143.03, 137.50, 136.04, 115.37, 114.66, 104.77, 61.18, 56.39, 56.08, 50.00; CIMS (isobutane) m/e 304 (MH+, 100). Anal. ($C_{17}H_{21}NO_4$) C, H.

4-Methoxy-N-(3,4,5-trimethoxyphenyl)benzylamine (12c): 1.42 g; 94%; mp 77°-8° C.; IR (KBr) 3380, 2980, 2960, 2940, 2820, 1605, 1580, 1520, 1460, 1440, 1255, 1225, 1130, 1110, 1010, 990 cm$^{-1}$; $^1$H NMR (CDCl$_3$, 500 MHz) δ7.29 (d, J=8.6 Hz, 2H), 6.88 (d, J=8.6 Hz, 2H), 5.87 (s, 2H), 4.22 (s, 2H), 3.82 (bs, 1H), 3.80 (s, 3H), 3.79 (s, 6H), 3.76 (s, 3H); CIMS (isobutane) m/e 304 (MH+, 100). Anal. ($C_{17}H_{21}NO_4$) C, H.

4-Benzyloxy-3,5-dimethoxybenzaldehyde (13j). A mixture of syringaldehyde (3.64 g, 20 mmol), benzyl chloride (2.52 g 20 mmol), NaI (2 g) and potassium carbonate (2.76 g, 20 mmol) in anhydrous acetone (60 mL) were refluxed for 5 h and cooled to room temperature. The solid materials were removed by filtration, the filtrate was concentrated and the residue was purified by chromatography on silica gel (230–400 mesh, 50 g) using 5% EtOAc in hexane as the eluent to obtain 13j (4.3 g, 79%); mp 62°-63° C.

4-(t-Butyldimethylsilyloxy)-3,5-dimethoxybenzaldehyde (13k). To a well-stirred solution of syringaldehyde (3.64 g, 20 mmol) and N,N-diisopropylethylamine (4.87 g, 30 mmol) in dry DMF (30 mL) at 0° C., t-butyldimethylsilyl chloride (3 g, 20 mmol) was added, and stirring was continued for 2 h at 0° C. and at room temperature for 10 h. The mixture was poured into icewater (500 mL), and the product was extracted with hexane (3×70 mL). The combined hexane extracts were washed with water (4×70 mL) and dried Na$_2$SO$_4$). Evaporation of solvents gave compound 4k as a white crystalline solid (5.17 g, 87%). An analytical sample was prepared by recrystallization from anhydrous ethanol. mp 70°-71° C.; $^1$H NMR (CDCl$_3$, 200 MHz) δ9.81 (s, 1H), 7.09 (s, 2H), 3.85 (s, 6H), 0.99 (s, 9H), 0.14 (s, 6H). Anal. ($C_{15}H_{24}O_4Si$) C, H.

The following compounds were prepared in accordance with the procedure described herein. More specifically, heating 3,4,5-trimethoxybenzaldehyde with p-substituted anilines 107a-g in refluxing toluene provided the Schiff bases 108a-g. Reduction of the imines 108a-g with sodium borohydride in ethanol at reflux gave the amines 109a-g, which were converted to the corresponding hydrochloride salts 110a-g with HCl gas in ether. All of the hydrochloride salts 110a-g were isolated as stable, crystalline solids.

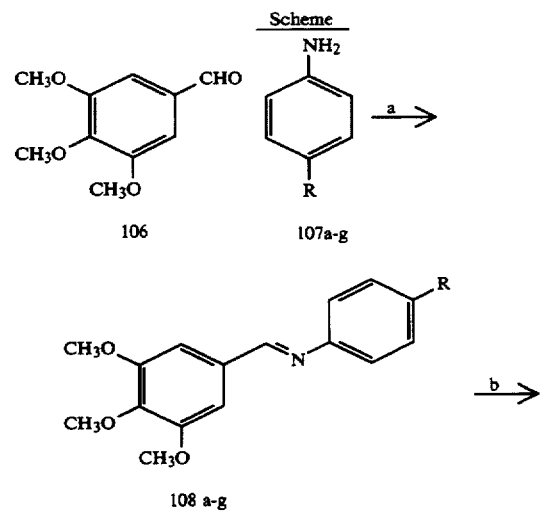

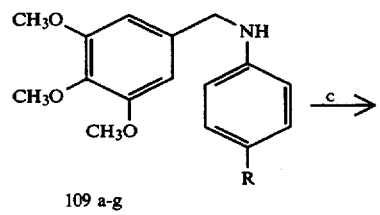

109 a-g

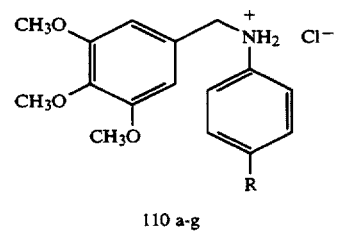

110 a-g a R = CH$_3$
b R = C$_2$H$_5$
c R = OCH$_3$
d R = OC$_2$H$_5$
e R = SCH$_3$
f R = CH(CH$_3$)$_2$
g R = CH$_2$CH$_2$CH$_3$ $^a$Toluene, reflux (3 h). $^b$NaBH$_4$, ethanol, reflux (2 h). $^c$HCl, ether, 0–5° C.(30 min).

4-Methyl-N-(3,4,5-trimethoxybenzylidene)aniline (108a). A mixture of compound 106 (6.0 g, 98%, 31.0 mmol) and 107a (3.21 g, 30 mmol) in ethanol (150 mL) was heated at reflux under argon for 3 h. After evaporation of the solvent, the residual white solid was recrystallized from ethyl acetate and hexane to give 108(a) (7.05 g, 82.4%) as white crystals: mp 74°-6° C. $^1$H NMR (200 MHz, CDCl$_3$) δ8.36 (s, 1H), 7.20 (d, J=8 Hz, 2H), 7.16 (s, 2H), 7.15 (d, J=8 Hz, 2H), 3.95 (s, 6H), 3.92 (s, 3H), 2.36 (s, 3H). EIMS m/e 285 (M+, 100).

4-Ethyl-N-(3,4,5-trimethoxybenzylidene)aniline (108b). A solution of 106 (6.0 g, 98%, 30 mmol) and 107b (3.63 g, 30 mmol) in ethanol (150 mL) was heated at reflux under argon for 3 h. The solvent was evaporated and the residual oil was subjected to flash chromatography (silica gel, 230–400 mesh, ether:hexane, 4:6 by volume) to give 108b (8.1 g, 90.3%) as an oil. $^1$H NMR (200 MHz, CDCl$_3$) δ8.36 (s, 1H), 7.23 (d, J=8 Hz, 2H), 7.16 (s, 2H), 7.15 (d, J=8 Hz, 2H), 3.94 (s, 6H), 3.91 (s, 3H), 2.67 (q, J=8 Hz, 2H), 1.26 (t, J=8 Hz, 3H). EIMS m/e 299 (M+, 100).

4-Methoxy-N-(3,4,5-trimethoxybenzylidene)aniline (108c). A mixture of 3,4,5-trimethoxybenzaldehyde 106 (19.6 g, 100 mmol) and 4-methoxyanaline (107c) (12.3 g, 100 mmol) in ethanol (100 mL) was heated at reflux under argon for 3 h. About half of the solvent was evaporated and the residual solution was filtered through a glass wool pad. The filtrate was left at room temperature overnight to give the crystalline (108c) (28.2 g, 93.7%): mp 78°-86° C. $^1$H NMR (200 MHz, CDCl$_3$) δ8.36 (s, 1H), 7.23 (d, J=8 Hz, 2H), 7.15 (s, 2H), 6.93 (d, J=8 Hz, 2H), 3.94 (s, 6H), 3.91 (s, 3H), 3.83 (s, 3H). CIMS (isobutane) m/e 302 (MH+, 100). Anal. ($C_{17}H_{19}NO_4$)C, H, N.

4-Ethoxy-N-(3,4,5-trimethoxybenzylidene)aniline (108d). From 3,4,5, trimethoxybenzaldehyde 106 (6.0 g, 30 mmol) and 4-ethoxyaniline 107d (4.1 g, 30 mmol), a similar procedure as described for 108a (5.9 g, 97.4%) as yellow crystals: mp 75°-7° C. after recrystallization from ethanol. $^1$H NMR (200 MHz, CDCl$_3$) δ8.37 (s, 1H), 7.21 (d, J=8 Hz, 2H), 7.14 (s, 2H), 6.91 (d, J=8 Hz, 2H), 4.05 (q, J=6 Hz, 2H), 3.94 (s, 6H), 3.91 (s, 3H), 1.43 (t, J=6 Hz, 3H). EIMS m/e 315 (M+, 93).

4-Methylthio-N-(3,4,5-trimethoxybenzylidene)aniline (108e). From compounds 107e (5.0 g, 98%, 35.2 mmol) and 106 (7.04 g, 98%, 35.2 mmol), a similar procedure, as described for 108a gave 108e (11.0 g, 98.2%) as yellow solid. The analytical sample was obtained by preparative TLC (ether:hexane, 1:2 by volume, precoated silica TLC plate, 1000 microns): mp 86°-88° C. $^1$H NMR (200 MHz, DMSO-d$_6$) δ8.54 (s, 1H), 7.31 (d, J=8 Hz, 2H), 7.23 (d, J=8 Hz, 2H), 7.26 (s, 2H), 3.85 (s, 3H), 3.84 (s, 3H), 3.73 (s, 3H), 2.49 (s, 3H), 2.49 (s, 3H). EIMS m/e 317 (M+, 100).

4-Isopropyl-N-(3,4,5-trimethoxybenzylidene)aniline (108f). From compounds 107f (4.2 g, 99%, 31.0 mmol) and 106 (6.0 g, 98%, 31.0 mmol), a similar procedure as described for 108a gave 108f (8.2 g, 84.5%) as a yellow solid: mp 68-70. $^1$H NMR (200 MHz, CDCl$_3$) δ8.37 (s, 1H), 7.25 (d, J=8 Hz, 2H), 7.16 (d, J=8 Hz, 2H), 7.16 (s, 2H), 3.94 (s, 6H), 3.91 (s, 3H), 2.93 (sextet, J=8 Hz, 1H), 1.27 (d, J=8 Hz, 6H). EIMS m/e 313 (M+, 100).

4-n-Propyl-N-(3,4,5-trimethoxybenzylidene)aniline (108g). From compounds 107g (4.2 g, 99%, 31.0 mmol) and 106 (6.0 g, 98%, 31.0 mmol), a similar procedure as described for 108a gave 108g (8.5 g, 87.6%) as a thick oil. $^1$H NMR (200 MHz, CDCl$_3$) δ8.36 (s, 1H), 7.20 (d, J=8 Hz, 2H), 7.16 (s, 2H), 7.14 (d, J=8 Hz, 2H), 3.93 (s, 6H), 3.91 (s, 3H), 2.60 (t, J=8 Hz, 2H), 1.64 (sextet, J=8 Hz, 2H), 0.95 (t, J=8 Hz, 3H). EIMS (M+ 100).

4-Methyl-N-(3,4,5-trimethoxybenzyl)aniline (109a). To a solution of (108a) (6.0 g, 21.1 mmol) in ethanol (100 mL) was added NaBH$_4$ (4.06 g, 98%, 105 mmol) in portions. The reaction mixture was stirred at reflux under argon for 2 h. The solvent was removed under reduced pressure. Saturated aqueous NaCl (30 mL) was added to the residue and the mixture extracted with ether (100, 40 and 40 mL). The combined ether layer was washed with saturated NaCl solution (30 mL), and dried over anhydrous Na$_2$SO$_4$. Evaporation of the filtrate gave 109a (5.6 g, 92.7%) as white crystals: mp 94°-6° C. after recrystallization from ethanol. $^1$H NMR (200 MHz, CDCl$_3$) δ7.00 (d, J=8 Hz, 2H), 6.61 (s, 2H), 6.58 (d, J=8 Hz, 2H), 4.23 (s, 2H), 3.84 (s, 9H), 2.24 (s, 3H). CIMS (isobutane) m/e 288 (MH+ 76).

4-Ethyl-N-(3,4,5-trimethoxybenzyl)aniline (109b). From 108b (7.0 g, 23.4 mmol) and NaBH$_4$ (4.4 g, 117 mmol), a similar procedure as described for 109a gave 109b (5.4 g, 76.6%) as white crystals: mp 64°-6° C. after recrystallization from ethanol. $^1$H NMR (200 MHz, CDCl$_3$) δ7.03 (d, J=8 Hz, 2H), 6.61 (s, 2H), 6.62 (d, J=8 Hz, 2H), 4.24 (s, 2H), 3.84 (s, 9H) 2.55 (q, J=8 Hz, 2H), 1.19 (t, J=Hz, 3H). EIMS m/e 301 (M+, 34).

4-Methoxy-N-(3,4,5-trimethoxybenzyl)aniline (109c). From 108c (10.8 g, 35.8 mmol) and NaBH$_4$ (6.8 g, 179 mmol), a similar procedure as described for 109a gave 109c (10.1 g, 93.5%) as pale purple crystals. $^1$H NMR (200 MHz, CDCl$_3$) δ6.79 (d, J=8 Hz, 2H), 6.62 (d, J=8 Hz, 2H), 6.61 (s, 2H), 4.21 (s, 2H), 3.84 (s, 9H), 3.74 (s, 3H). CIMS (isobutane) m/e 304 (MH+, 20).

4-Ethoxy-N-(3,4,5-trimethoxybenzyl)aniline (109d). From the imine 108d (5.6 g, 17.8 mmol) and NaBH$_4$ (3.4 g, 88 mmol), a similar procedure as described for 109a gave 109d (4.6 g, 81.9%) as white crystals: mp 76°-8° C. after recrystallization from ethanol. $^1$H NMR (200 MHz, CDCl$_3$) δ6.78 (d, J=8 Hz, 2H), 6.62 (d, J=8 Hz, 2H), 6.61 (s, 2H), 4.21 (s, 2H), 3.96 (q, J=6 Hz, 2 Hz), 3.84 (s, 9H), 1.37 (t, J=6 Hz, 3H). CIMS (isobutane) m/e 318 (MH+, 27).

4-Methylthio-N-(3,4,5-trimethoxybenzyl)aniline (109e). From 108e (11.0 g, 35.0 mmol) and NaBH$_4$ (6.6 g, 175 mmol), a similar procedure as described in 109a gave 109e (10.6 g, 94.9%) as an oil: $^1$H NMR (200 MHz, DMSO-d$_6$) δ7.07 (d, J=8 Hz, 2H), 6.67 (s, 2H), 6.57 (d, J=8 Hz, 2H), 6.23 (t, J=6 Hz, 1H), 4.10, (d, J=6 Hz, 2H), 3.73 (s, 6H), 3.62 (s, 3H), 2.31 (s, 3H). EIMS m/e 319 (M+, 69).

4-Isopropyl-N-(3,4,5,-trimethoxybenzyl)aniline (109f). From 108f (8.2 g, 26.0 mmol), a similar procedure as described for 109a gave 109f (7.4 g, 89.8%) as an oil. $^1$H NMR (200 MHz, CDCl$_3$) δ7.06 (d, J=8 Hz, 2H), 6.61 (d, J=8 Hz, 2H), 6.61 (s, 2H), 4.24 (s, 2H), 3.84 (s, 9H), 2.81 (h, J=8 Hz, 1H, 1.21 (d, J=8 Hz, 6H). EIMS 315 (M+, 100).

4-n-Propyl-N-(3,4,5-trimethoxybenzyl)aniline (109g). From 108g (8.5 g, 26.9 mmol), a similar procedure as described for 109a gave 109g (6.0 g, 70.3%) as an oil. $^1$H NMR (200 MHz, CDCl$_3$) δ7.00 (d, J=8 Hz, 2H), 6.61 (s, 2H), 6.60 (d, J=8 Hz, 2H), 4.23 (s, 2H), 3.84 (s, 9H), 2.84 (t, J=8 Hz, 2H), 1.60 (sextet, J=8 Hz, 2H), 0.92 (t, J=8 Hz, 3H). EIMS m/e 315 (M+, 93).

4-Methyl-N-(3,4,5-trimethoxybenzyl)aniline Hydrochloride (110a). A solution of 109a (3.9 g, 13.6 mmol) in ether (150 mL) was treated with HCl gas at 0°-5° C. with stirring for about 0.5 h. Collection of the resulting pale purple crystals and recrystallization from ethanol and methanol gave 109a (3.6 g, 81.8%) as tiny white crystals: mp 162°-4° C. after recrystallization from ethanol. $^1$H NMR (200 MHz, CDCl$_3$) δ7.21 (d, J=2H), 7.09 (d, J=8 Hz, 2H), 6.63 (s, 2H), 4.26 (s, 2H), 3.77 (s, 6H), 3.76 (s, 3H), 2.30 (s, 3H). Anal. (C$_{17}$H$_{22}$ClNO$_3$) C, H, N.

4-Ethyl-N-(3,4,5-trimethoxybenzyl)aniline Hydrochloride (110b). From 109b (4.0 g, 13.2 mmol), a similar procedure as described in 110a gave 110b (3.17 g, 70.7%), as yellow crystals: mp 155°-7° C. after recrystallization from ethanol and methanol. $^1$H NMR (200 MHz, CDCl$_3$) δ7.20 (s, br, 4H), 6.86 (s, 2H), 4.34 (s, 2H), 3.72 (s, 6H), 3.62 (s, 3H), 2.55 (q, J=8 Hz, 2H), 1.13 (t, J=8 Hz, 3H). Anal. (C$_{18}$H$_{24}$ClNO$_3$).

4-Methoxy-N-(3,4,5-trimethoxybenzyl)aniline Hydrochloride (110c). From 109c (9.0 g, 29.7 mmol), a similar procedure as described for 110a gave 110c (8.14 g, 80.7%) as tiny white crystals: mp 182°-4° C. $^1$H NMR (200 MHz, DMSO-d$_6$) δ7.36 (d, J=8 Hz 2H), 6.98 (d, J=8 Hz, 2H), 6.62 (s, 2H), 4.36 (s, 2H), 3.74 (s, 9H), 3.63 (s, 3H). Anal. (C$_{17}$H$_{22}$ClNO$_4$.½H$_2$O)C, H, N.

4-Ethoxy-N-(3,4,5-trimethoxybenzyl)aniline Hydrochloride (110d). From 109d (4.0 g, 12.6 mmol), a similar procedure as described for 110a gave 109d (3.4 g, 76.2%) as white crystals: mp 170°-2° C. after recrystallization from ethanol and methanol. $^1$H NMR (200 MHz CDCl$_3$) δ7.22 (d, J=8 Hz, 2H), 6.57 (d, J=8 Hz, 2H) 6.64 (s, 2H), 4.25 (s, br, 2H), 3.95 (q, J=6 Hz, 2H), 3.79 (s, 6H), 3.77 (s, 3H), 1.38 (t, J=6 Hz, 3 H). Anal. (C$_{18}$H$_{24}$ClNO$_4$), C, H, N.

4-Methylthio-N-(3,4,5-trimethoxybenzyl)aniline Hydrochloride (110e). From 109e (3.0 g, 9.4 mmol), a similar procedure as described for 110a gave 110e (1.80 g, 53.9%) as yellow crystals: mp 194°-6° C. after recrystallization from ethanol:methanol:water. $^1$H NMR (200 MHz, DMSO-d$_6$) δ7.23 (d, J=8 Hz, 2H), 7.07 (d, J=8 Hz, 2H), 6.83 (s, 2H), 4.30 (s, 2H), 3.73 (s, 6H), 3.62 (s, 3H), 3.62 (s, 3H), 2.40 (s, 3H). Anal (C₁₇H₂₂ClNO₃S) C, H, N.

4-Isopropyl-N-(3,4,5-trimethoxybenzyl)aniline Hydrochloride (110f). From 109f (6.0 g, 18.9 mmol), a similar procedure as described for 110a gave 110f (4.4 g, 65.9%), as yellow crystals: mp 160°-2° C. after recrystallization from methanol:ethanol:water. ¹H NMR (200 MHz, CDCl₃) δ7.35 (d, J=8 Hz, 2H), 7.29 (d, J=8 Hz, 2H), 6.92 (s, 2H), 4.37 (s, 2H), 3.73 (s, 6H), 3.63 (s, 3H), 2.88 (h, J=6 Hz, 1H), 1.17 (d, J=6 Hz, 6H). Anal. (C₁₉H₂₆ClNO₃) C, H, N.

4-n-Propyl-N-(3,4,5-trimethoxybenzyl)aniline Hydrochloride (110g). From 109g (6.0 g, 19.0 mmol), a similar procedure as described for 110a gave 110g (5.5 g, 82.5%) as yellow crystals, mp 118°-20° C. after recrystallization from ethyl acetate:methanol:hexane. ¹H NMR (200 MHz, CDCl₃) δ7.21 (d, J=8 Hz, 2H), 7.08 (d, J=8 Hz, 2H), 6.58 (s, 2H), 4.29 (s, 2H), 3.78 (s, 3H), 3.74 (s, 6H), 3.52 (t, J=8 Hz, 2H), 1.56 (sextet, J=8 Hz, 2H), 0.86 (t, J=8 Hz, 3H). Anal. (C₁₉H₂₆ClNO₃) C, H, N.

4-Methoxy-N-(3,4,5-trimethoxybenzylidene)aniline (108c). Anal. calcd for C₁₇H₁₉NO₄: C, 67.76; H, 6.35; N, 4.65. Found: C, 68.11; H, 6.28; N, 4.54.

4-Methyl-N-(3,4,5-trimethoxybenzyl)aniline Hydrochloride (110a). Anal. calcd for C₁₇H₂₂ClNO₃: C, 63.06; H, 7.01; N, 4.33. Found: C, 62.92; H, 7.15; N, 4.37.

4-Ethyl-N-(3,4,5-trimethoxybenzyl)aniline Hydrochloride (110b). Anal. calcd for C₁₈H₂₄ClNO₃: C, 63.99; H, 7.16; N, 4.15. Found: C, 63.96; H, 7.24; N, 3.90.

4-Methoxy-N-(3,4,5-trimethoxybenzyl)aniline Hydrochloride (110c). Anal. calcd for C₁₇H₂₂ClNO₄.½H₂O: C, 58.53; H, 6.64; N, 4.02. Found: C, 58.52; H, 6.31; N, 3.89.

4-Ethoxy-N-(3,4,5-trimethoxybenzyl)aniline Hydrochloride (110d). Anal. calcd for C₁₈H₂₄ClNO₄: C, 61.10; H, 6.84; N, 3.96. Found: C, 61.27; H, 6.91; N, 3.68.

4-Methylthio-N-(3,4,5-trimethoxybenzyl)aniline Hydrochloride (110e). Anal. calcd for C₁₇H₂₂ClNO₃S: C, 57.37; H, 6.23; N, 3.94. Found: C, 57.19; H, 6.33; N, 3.95.

4-Isopropyl-N-(3,4,5-trimethoxybenzyl)aniline Hydrochloride (110f). Anal. calcd for C₁₉H₂₆ClNO₃: C, 64.86; H, 7.44; N, 3.98. Found: C, 64.75; H, 7.51; N, 3.95.

4-n-propyl-N-(3,4,5-trimethoxybenzyl)aniline Hydrochloride (110g). Anal. calcd for C₁₉H₂₆ClNO₃: C, 64.86; H, 7.44; N, 3.98, Found: C, 64.59; H, 7.61; N, 3.94.

General procedure for the preparation of Stilbenes 15a-k. Sodium hydride (0.2 g, 4 mmol) was added to a well-stirred suspension of the phosphonium bromide 14a-b (2 mmol) and the aldehyde 13a-k (2 mmol) in THF (30 mL), and the mixture was stirred at room temperature for 24 h. The mixture was cooled to 0° C., and the excess sodium hydride was quenched by careful addition of methanol (5 mL). Solvents were removed at reduced pressure, and the residue was subjected to preparative thin-layer chromatography on silica gel using 20% EtOAc in hexane as the eluent to get the Z and E isomers in pure form.

(Z)-1-(4-Ethoxyphenyl)-2-(3,4,5-trimethoxyphenyl)ethene (15a): 313 mg; 44%; oil; ¹H NMR (CDCl₃, 200 MHz) δ7.23 d, J=8.8 Hz, 2H), 6.78 (d, J=8.8 Hz, 2H), 6.52 (d, J=12.1 Hz, 1H), 6.51 (s, 2H), 6.41 (d, J=12.1 Hz, 1H), 4.01 (q, J=7.0 Hz, 2H), 3.84 (s, 3H), 3.69 (s, 6H), 1.39 (t, J=7.0 Hz, 3H); CIMS (isobutane) m/e 315 (MH+, 100). Anal. (C₁₉H₂₂O₄) C, H.

(Z)-1-(4-n-Propoxyphenyl)-2-(3,4,5-trimethoxyphenyl)-thene (15b): 346 mg; 53%; oil; ¹H NMR (CDCl₃, 200 MHz) δ7.23 (d, J=8.8 Hz, 2H), 6.78 d, J=8.8 Hz, 2H) 6.52 (s, 2H), 6.52 (d J=12.2 Hz, 1H), 6.41 (d, J=12.2 Hz, 1H) (d, J=12.2 Hz, 1H), 3.88 (t, J=6.6 Hz, 2H), 3.84 (s, 3H), 3.69 (s, 6H), 1.79 (sextet, J=6.6 Hz, 2H), 1.02 (t, J=6.6 Hz, 3H); CIMS (isobutane) m/e 329 MH+, 100). Anal. (C₂₀H₂₄O₄) C, H.

(Z)-1-(4-Methylthiophenyl)-2-(3,4,5-trimethoxyphenyl)ethene (15c): 319 mg; 51%; oil; ¹H NMR (CDCl₃, 200 MHz) δ7.23 (d, J=8.4 Hz, 2H), 7.13 (d, J=8.4 Hz, 2H), 6.50 (bs, 2H), 6.49 (s, 2H), 3.84 (s, 3H), 3.69 (s, 6H), 2.46 (s, 3H); CIMS (isobutane) m/e 317 (MH+, 100). Anal. (C₁₈H₂₀O₃) C, H.

(Z)-(4-Methylphenyl)-2-(3,4,5-trimethoxyphenyl)ethene (15d): 294 mg; 50%; oil; ¹H NMR (CDCl₃, 200 MHz) d 7.20 (d, J=8.0 Hz, 2H), 7.07 (d, J=8.0 Hz, 2H), 6.56 (d, J=12.2 Hz, 1H), 6.49 (s, 2H), 6.45 (d, J=12.2 Hz, 1H), 3.83 (s, 3H), 3.67 (s, 6H), 2.31 (s, 3H); ¹³C NMR (CDCl₃, 50 MHz) δ153.28, 137.56, 137.30, 134.77, 133.14, 130.35, 129.82, 129.22, 106.31, 61.09, 55.99, 21.27; CIMS (isobutane) m/e 285 (MH+, 100). Anal. (C₁₈H₂₀O₃) C, H.

(Z)-(4-Ethylphenyl)-2-(3,4,5-trimethoxyphenyl)ethene (15e): 321 mg; 54%; oil; ¹H NMR (CDCl₃, 200 MHz) d 7.21 (d, J=8.1 Hz, 2H), 7.00 (d, J=8.1 Hz, 2H), 6.57 (d, J=12.1 Hz, 1H), 6.48 (s, 2H), 6.46 (d, J=12.1 Hz, 1H), 3.84 (s, 3H), 3.66 (s, 6H), 2.61 (q, J=7.4 Hz, 2H), 1.20 (t, J=7.4 Hz, 3H); CIMS (isobutane) m/e 299 (MH+, 100). Anal. (C₁₉H₂₂O₃) C, H.

(Z)-[4-(2-Propyl)phenyl]-2-(3,4,5-trimethoxyphenyl)ethene (15f): 340 mg; 55%; oil; ¹H NMR (CDCl₃, 200 MHz) δ7.23 (d, J=8.2 Hz, 2H); 7.13 (d, J=8.2 Hz, 2H), 6.60 (d, J=12.2 Hz, 1H), 6.46 (s, 2H), 6.46 (d, J=12.2 Hz, 1H), 3.83 (s, 3H), 3.65 (s, 6H), 2.88 (sextet, J=7.0 Hz, 1H), 1.27 (d, J-7.0 Hz, 6H); CIMS (isobutane) m/e 313 (MH+, 100). Anal. (C₂₀H₂₄O₃) C, H.

(Z)-1-(4-t-Butylphenyl)-2-(3,4,5-trimethoxyphenyl)ethene (15g): 192 mg; 31%; oil; ¹H NMR (CLCl₃, 200 MHz) δ7.29 (d, J=8.4 Hz, 2H), 7.23 (d, J=8.4 Hz, 2H), 6.60 (d, J=12.2 Hz, 1H), 6.46 (d, J=12.2 Hz, 1H), 6.45 (s, 2H), 3.83 (s, 3H), 3.64 (s, 6H), 1.29 (s, 9H); CIMS (isobutane) m/e 327 (MH+, 100%). Anal. (C₂₁H₂₆O₃) C, H.

(Z)-(4-Methoxyphenyl)-2-(3,4-dimethoxyphenyl)ethene (15h): 280 mg; 46%; oil; ¹H NMR (CLCl₃, 200 MHz) δ7.23 (d, J=8.8 Hz, 2H), 6.83-6.75 (m, 5H), 6.46 (s, 2H), 3.87 (s, 3H), 3.79 (s, 3H), 3.65 (s, 3H); CIMS (isobutane) m/e 271 (MH+, 100). Anal. (C₁₇H₁₈O₃) C, H.

(Z)-1-(3,5-Dimethoxyphenyl)-2-(4-methoxyphenyl)ethene (15i): 241 mg; 45%; oil; ¹H NMR (CDCl₃, 200 MHz) δ7.22 (d, J=8.8 Hz, 2H), 6.77 (d, J=8.8 Hz, 2H), 6.54 (d, J=12.2 Hz, 1H), 6.46 (d, J=2.3 Hz, 2H), 6.44 (d, J=12.2 Hz, 1H), 6.32 (t, J=2.3 Hz, 1H), 3.79 (s, 3H), 3.67 (s, 6H); CIMS (isobutane) m/e 271 (MH+, 100). Anal. (C₁₇H₁₈O₃) C, H.

(Z)-1-[4-(Benzyloxy)-3,5-(dimethoxy)phenyl]-2-(4-methoxyphenyl)ethene (15j): 294 mg; 33%; oil; ¹H NMR (CDCl₃, 200 MHz) δ7.52-7.45 (m, 2H), 7.41-7.26 (m, 3H), 7.21 (d, J=8.7 Hz, 2H), 6.78 (d, J=8.75 Hz, 2H), 6.52 (d, J=12.1 Hz, 1H), 6.49 (s, 2H), 6.42 (d, J=12.1 Hz, 1H), 5.01 (s, 2H), 3.79 (s, 3H), 3.66 (s, 6H); CIMS (isobutane) m/e 377 (MH+, 100). Anal. C₂₄H₂₄O₄) C, H.

(Z)-1-[4-{(t-Butyldimethylsilyl)-oxy}-3,5-(dimethoxy)-phenyl]-2-(4-methoxyphenyl)ethene (15k): 277 mg; 35%; oil; ¹H NMR (CDCl₃, 200 MHz) δ7.23 (d, J=8.8 Hz, 2H) 6.76 (δ, J=8.8 Hz, 2H), 6.49 (s, 2H), 6.45 (s, 2H), 3.78 (s, 3H), 3.63 (s, 6H), 1.02 (s, 9H), 0.14 (s, 6H);

$^{13}$C NMR (CDCl$_3$, 50 MHz) d 159.21 151.90, 134.04, 129.63, 129.21, 113.95, 106.47, 55.86, 55.51, 26.06, 18.96, −4.49. Anal. (C$_{23}$H$_{22}$O$_4$Si) C, H.

(E)-1-(4-n-Propoxyphenyl)-2-(3,4,5-trimethoxyphenyl)ethene (16b): 187 mg; 28%; mp 82°–83° C.; $^1$H NMR (CDCl$_3$, 200 MHz); δ7.44 (d, J=8.8 Hz, 2H), 6.95–6.87 (m, 4H), 6.72 (s, 2H), 3.93 (t, J=6.6 Hz, 2H), 3.91 (s, 6H), 3.89 (s, 3H), 1.82 (sextet, J=6.6 Hz, 2H), 1.04 (t, J=6.6 Hz, 3H); CIMS (isobutane) m/e 329 MH+, 100). Anal. (C$_{20}$H$_{24}$O$_4$) C, H.

(E)-(4-Methylphenyl)-2-(3,4,5-trimethoxyphenyl)ethene (16d): 121 mg; 21%; mp 125°–127° C.; $^1$H NMR (CDCl$_3$, 200 MHz) δ7.40 (d, J=8.1 Hz, 2H), 7.16 (d, J=8.1 Hz, 2H), 6.98 (s, 2H), 6.73 (s, 2H), 3.91 (s, 6H), 3.87 (s, 3H), 2.35 (s, 3H); $^{13}$C NMR (CDCl$_3$, 200 MHz) δ153.84, 138.19, 137.90, 134.81, 133.68, 129.80, 128.50, 128.00, 126.71, 103.74, 61.12, 56.25, 21.30; CIMS (isobutane) m/e 285 (MH+, 100). Anal. (C$_{18}$H$_{20}$O$_3$) C, H.

(E)-(4-Ethylphenyl)-2-(3,4,5-trimethoxyphenyl)ethene (16e): 182 mg; 30%; mp 98°–100° C.; $^1$H NMR (CDCl$_3$, 200 MHz) δ7.44 (d, J=8.1 Hz, 2H), 7.20 (d, J=8.1 Hz, 2H), 7.00 (s, 2H), 6.74 (s, 2H), 3.92 (s, 6H), 3.87 (s, 3H), 2.66 q, J=7.4 Hz, 2H), 1.26 (t, J=7.4 Hz, 3H); CIMS (isobutane) m/e 299 (MH+, 100). Anal. (C$_{19}$H$_{22}$O$_3$) C, H.

(E)-[4-(2-Propyl)phenyl]-2-(3,4,5-trimethoxyphenyl)ethene (16f): 151 mg; 24%; mp 74°–75° C.; $^1$H NMR (CDCl$_3$, 200 MHz) d 7.45 (d, J=8.2 Hz, 2H), 7.23 (d, J=8.2 Hz, 2H), 7.00 (s, 2H), 6.74 (s, 2H), 3.93 (s, 6H), 3.87 (s, 3H), 2.92 (sextet, J=7.0 Hz, 1H), 1.27 (d, J=7.0 Hz, 6H); CIMS (isobutane) m/e 313 (MH+, 100). Anal. (C$_{20}$H$_{24}$O$_3$) C, H.

(E)-1-(4-t-Butylphenyl)-2-(3,4,5-trimethoxyphenyl)ethene (16g): 143 mg; 23%; mp 127°–128° C.; $^1$H NMR (CDCl$_3$, 200 MHz) δ7.46 (d, J=8.7 Hz, 2H), 7.38 (d, J=8.7 Hz, 2H), 7.0 (s, 2H), 6.74 (s, 2H), 3.92 (s, 6H), 3.87 (s, 3H), 1.34 (s, 9H); CIMS (isobutane) m/e 327 (MH+, 100%). Anal. (C$_{21}$H$_{26}$O$_3$) C, H.

(E)-(4-Methoxyphenyl)-2-(3,4-dimethoxyphenyl)ethene (16h): 110 mg; 20%; mp 135°–137° C.

(E)-1-(3,5-Dimethoxyphenyl)-2-(4-methoxyphenyl)ethene (16i): 123 mg; 23%; mp 55°–56° C.

(E)-1-[4-(Benzyloxy)-3,5-(dimethoxy)phenyl]-2-(4-methoxyphenyl)ethene (16j): 207 mg; 28%; mp 104°–105° C.; $^1$H NMR (CDCl$_3$, 200 MHz) δ7.55–7.48 (m, 2H), 7.45 (d, J=8.8 Hz, 2H, 7.40–7.25 (m, 3H), 6.98 (d, J=16.1 Hz, 1H), 6.90 (d, J=8.8 Hz, 2H), 6.89 (d, J=16.1 Hz, 1H), 6.71 (s, 2H), 5.03 (s, 2H), 3.87 (s, 6H), 3.83 (s, 3H); CIMS (isobutane) m/e 377 (MH+, 100). Anal. (C$_{24}$H$_{24}$O$_4$) C, H.

(E)-1-[4-{(t-Butyldimethylsilyl)-oxy}-3,5-(dimethoxy)-phenyl]-2-(4-methoxyphenyl)ethene (16k): 224 mg; 28%; mp 118°–120° C.; $^1$H NMR (CDCl$_3$, 200 MHz) δ7.42 (δ, J=8.8 Hz, 2H), 6.91 (s, 2H), 6.88 (d, J=8.8 Hz, 2H), 6.69 (s, 2H), 3.84 (s, 6H), 3.82 (s, 3H), 1.01 (s, 9H), 0.14 (s, 6H); $^{13}$C NMR (CDCl$_3$, 50 MHz) δ159.67, 152.33, 130.97, 130.87, 127.98, 127.49, 127.04, 114.59, 103.93, 56.08, 55.61, 26.03, 18.54, −4.42. Anal. (C$_{23}$H$_{32}$O$_4$Si) C, H.

Preparation of acetates 15i and 16i. A solution of n-Bu$_4$NF in THF (1M, 2 mL, 2 mmol) was added to a solution of stilbenes 15k and 16k (400 mg, 1 mmol) in THF (5 mL) and the mixture was stirred at 0° C. After 30 min., acetic anhydride (0.5 mL) was added, and stirring was continued at room temperature for 24 h. Solvents were evaporated at reduced pressure and the residue was mixed with water (50 mL). The product was extracted with ether (2×25 mL) and the ether solution was washed with water (2×100 mL). Evaporation of the solvents and purification of the crude product by preparative TLC using 40% EtOAc in hexane as the eluent afforded the desired products.

(Z)-1-(4-Acetoxy-3,5-dimethoxyphenyl)-2-(4-methoxyphenyl)ethene (15l): 111 mg; 33%; oil; $^1$H NMR (CDCl$_3$, 200 MHz) δ7.24 (d, J=8.6 Hz, 2H), 6.78 (d, J=8.6 Hz, 2H), 6.55 (d, J=12.1 Hz, 1H), 6.53 (s, 2H), 6.43 (d, J=12.1 Hz, 1H), 3.77 (s, 3H), 3.64 (s, 6H), 2.32 (s, 3H); $^{13}$C NMR (CDCl$_3$, 50 MHz) δ169.27, 159.27, 152.24, 136.00, 130.66, 130.53, 129.79, 128.84, 127.93, 113.90, 105.85, 56.11, 55.37, 20.51; CIMS (isobutane) m/e 329 (MH+, 100). Anal. (C$_{19}$H$_{20}$O$_5$) C, H.

(E)-1-(4-Acetoxy-3,5-dimethoxyphenyl)-2-(4-methoxy-phenyl)ethene (16l): 137 mg; 41%; mp 129°–131° C.; $^1$H NMR (CDCl$_3$, 200 MHz) δ7.45 (d, J=8.8 Hz, 2H), 6.97–6.88 (m, 4H), 6.73 (s, 2H), 3.87 (s, 6H), 3.83 (s, 3H), 2.35 (s, 3H); $^{13}$C NMR (CDCl$_3$, 50 MHz) δ169.35, 159.87, 152.70, 136.55, 130.18, 128.95, 128.13, 126.73, 114.48, 103.16 56.28, 55.48, 20.55; CIMS (isobutane) m/e 329 (MH+, 100). Anal. (C$_{19}$H$_{20}$O$_5$) C, H.

General procedure for the preparation of dihydrostilbenes 17a–e. A mixture of E-stilbenes (16) and the corresponding Z-stilbenes (15) (1 mmol) in EtOAc was hydrogenated at 40 psi in the presence of 10% palladium on charcoal (50 mg) for 4 h. The catalyst was removed by filtration, and the filtrate was concentrated, yielding the dihydrostilbene derivatives 17a–c. Analytical samples were prepared by preparative thin-layer chromatography on silica gel using 20% EtOAc in hexane as the eluent.

1-(4-Ethoxyphenyl)-2-(3,4,5-trimethoxyphenyl)ethane (17a): 250 mg; 80%; oil; $^1$H NMR (CDCl$_3$, 200 MHz) δ7.06 (d, J=8.5 Hz, 2H), 6.80 (d, J=8.5 Hz, 2H), 6.34 (s, 2H), 4.32 (q, J=7.3 Hz, 2H), 3.81 (s, 3H), 3.80 (s, 6H), 2.82 (s, 4H), 1.40 (t, J=7.3 Hz, 3H) ; CIMS (isobutane) m/e 317 (MH+, 100%). Anal. (C$_{19}$H$_{24}$O$_4$) C, H.

1-(4-n-Propoxyphenyl)-2-(3,4,5-trimethoxyphenyl)ethane (17b): 284 mg; 86%; oil; $^1$H NMR (CDCl$_3$, 200 MHz) δ7.09 (d, J=8.6 Hz, 2H), 6.83 (d, J=8.6 Hz, 2H), 6.37 (s, 2H), 3.90 (t, J=6.6 Hz, 2H), 3.82 (s, 9H), 2.84 (s, 4H), 1.80 (m, 2H), 1.03 (t, J=7.4 Hz, 3H) ; CIMS (isobutane) m/e 331 (MH+, 100). Anal. (C$_{20}$H$_{26}$O$_4$) C, H.

1-(4-Methylthiophenyl)-2-(3,4,5-trimethoxyphenyl)ethane (17c): 276 mg; 86%; mp 52°–54° C.; $^1$H NMR (CDCl$_3$, 200 MHz) δ7.21 (d, J=8.1 Hz, 2H), 7.11 (d, J=8.1 Hz, 2H), 6.36 (s, 2H), 3.82 (bs, 9H), 2.86 (bs, 4H), 2.47 (s, 3H); CIMS (isobutane) m/e 319 (MH+, 100). Anal. (C$_{18}$H$_{22}$O$_3$S) C, H.

1-(4-Methylphenyl)-2-(3,4,5-trimethoxyphenyl)ethane (17d): 247 mg; 86%; mp 51°–52° C.; $^1$H NMR (CDCl$_3$, 200 MHz) δ7.09 (s, 4H), 6.38 (s, 2H), 3.83 (s, 3H), 3.82 (s, 6H), 2.85 (bs, 4H), 2.32 (s, 3H); CIMS (isobutane) m/e 287 (MH+, 100). Anal. (C$_{18}$H$_{22}$O$_3$) C, H.

1-(4-Ethylphenyl)-2-(3,4,5-trimethoxyphenyl)ethane (17e): 261 mg; 87%; oil: $^1$H NMR (CDCl$_3$, 200 MHz) δ7.12 (s, 4H), 6.37 (s, 2H), 3.83 (s, 3H), 3.82 (s, 6H), 2.86 (bs, 4H), 2.63 (q J=7.6 Hz, 2H), 1.23 (t, J=7.6 Hz, 3H); CIMS (isobutane) m/e 299 (MH+, 100). Anal. (C$_{19}$H$_{22}$O$_3$) C, H.

General procedure for the preparation of Compounds 17f–g. A mixture of 1-(4-hydroxyphenyl)-2-(3,4,5-trimethoxyphenyl)ethane (18) 288 mg, 1 mmol), aminoalkyl chloride hydrochloride 19a–b (1.1 mmol) and potassium carbonate (276 mg, 2 mmol) in acetone (15 mL) was heated at reflux for 12 h, and the solids were removed by filtration. The filtrate was concentrated, and the residue was purified by column chromatography on silica gel using 5% methanol in $CHCl_3$ as the eluent. All these compounds were obtained as viscous oils.

1-[4-(2-N,N-Dimethylaminoethoxy)phenyl])-2-(3,4,5-trimethoxyphenyl)ethane (17f): 243 mg; 68%; oil; $^1$H NMR ($CDCl_3$, 500 MHz) $\delta$7.08 (d, J=8.5 Hz, 2H), 6.85 (d, J=8.5 Hz, 2H), 6.36 (s, 2H), 4.09 (t, J=5.5 Hz, 2H), 3.82 (s, 3H), 3.81 (s, 6H), 2.85–2.80 (m, 6H), 2.41 (s, 6H); CIMS (isobutane) m/e 360 (MH+, 100). Anal. ($C_{21}H_{29}O_4$) C, H.

1-[4-(2-N,N-Diethylaminoethoxy)phenyl])-2-(3,4,5-trimethoxyphenyl)ethane (17g): 296 mg; 76%; oil; $^1$H NMR ($CDCl_3$, 500 MHz) $\delta$7.10 (d, J=8.5 Hz, 2H), 6.84 (d, J=8.5 Hz, 2H), 6.38 (s, 2H), 4.08 (t, J=6.2 Hz, 2H), 3.85 (s, 3H), 3.84 (s, 6H), 2.94 (t, J=6.2 Hz, 2H), 2.86–2.82 (m, 4H), 2.71 (q, J=7.1 Hz, 4H), 1.11 (t, J=7.1 Hz, 6H); CIMS (isobutane) m/e 388 (MH+, 100). Anal. ($C_{23}H_{33}NO_4$) C, H.

Typical procedure for preparation of compounds 17h–j. A solution of compound 20a (2 mmol) in THF (20 mL) was added to a well-stirred solution of LDA (2 mmol) in THF (22 mL) at −78° C., and stirring continued for 30 min. To this 4-methoxybenzyl bromide (21a) (2 mmol) was added, and stirring continued at −78° C. for 1 h and at room temperature for 6 h. The reaction mixture was quenched by the addition of glacial acetic acid (2 mL) and the solvents were distilled off at reduced pressure. The residue was treated with water (20 mL) and the solvents were distilled off at reduced pressure. The residue was treated with water (20 mL) and the product was extracted with ether (2×70 mL). The combined ether extracts were washed with water and dried ($Na_2SO_4$). Evaporation of the ether and re-crystallization of the residue from $CH_2Cl_2$-hexane gave compound 17h. Compounds 17i and 17j were prepared by using the same method.

3-(4-Methoxyphenyl)-2-(3,4,5-trimethoxyphenyl)-propanonitrile (17h): 320 mg; 49%; mp 82°–83° C.; $^1$H NMR ($CDCl_3$, 200 MHz) $\delta$7.05 (d, J=8.5 Hz, 2H), 6.83 (d, J=8.5 Hz, 2H), 6.41 (s, 2H), 3.89 (t, J=7.2 Hz, 1H), 3.84 (s, 3H), 3.81 (s, 6H), 3.78 (s, 3H), 3.12–3.07 (m, 2H); CIMS (isobutane) m/e 328 (MH+, 100). Anal. ($C_{19}H_{21}O_4$) C, H.

2-(4-Methoxyphenyl)-3-(3,4,5-trimethoxyphenyl)-propanonitrile (17i): 450 mg; 69%; mp 102°–103° C.; $^1$H NMR ($CDCl_3$, 200 MHz) $\delta$7.13 (d, J=8.5 Hz, 2H), 6.85 (d, J=8.5 Hz, 2H), 6.28 (s, 2H), 3.92 (t, J=6.7 Hz, 1H), 3.80 (s, 3H), 3.76 (s, 3H), 3.75 (s, 6H), 3.06–3.00 (m, 2H); CIMS (isobutane) m/e 328 (MH+, 100). Anal. ($C_{19}H_{21}NO_4$) C, H.

Methyl 2-(4-methoxyphenyl)-3-(3,4,5-trimethoxyphenyl)n-proponate (17j): 533 mg; 74%; mp 84°–5° C.; $^1$H NMR ($CDCl_3$, 200 MHz) $\delta$7.22 (d, J=8.5 Hz, 2H), 6.85 (d, J=8.5 Hz, 2H), 6.29 (s, 2H), 3.80 (s, 3H), 3.78 (s, 6H), 3.77 (s, 3H), 3.62 (s, 3H), 3.42–3.24 (m, 2H), 3.00 (m, 1H); CIMS (isobutane) m/e 361 (MH+, 100%). Anal. ($C_{20}H_{24}O_6$) C, H.

General procedure for the preparation of Compounds 23a–c. A mixture of phenylacetic acid 22a–b (2 mmol), benzaldehyde 13l–m (2 mmol) and triethylamine (0.5 mL) in acetic anhydride (5 mL) was heated at reflux for 12 h and poured into hot saturated sodium carbonate solution (50 mL) and left overnight. The mixture was extracted with ether (2×50 mL), and the ether extracts were discarded. The aqueous solution was acidified with dil. HCl and the precipitated product was filtered and dried. Recrystallization from EtOAc-hexane gave pure product.

(E)-3-(4-Methoxyphenyl)-2-(3,4,5-trimethoxyphenyl)-prop-2-enoic acid (23a): 523 mg; 76%; mp 187°–189° C.; $^1$H NMR ($CDCl_3$, 200 MHz) $\delta$9.8 (bs, 1H), 7.89 (s, 1H), 7.07 (d, J=8.9 Hz, 2H), 6.73 (d, J=8.9 Hz, 2H), 6.47 (s, 2H), 3.91 (s, 3H), 3.79 (s, 6H), 3.78 (s, 3H); $^{13}$C NMR ($CDCl_3$, 50 MHz) $\delta$173.90, 161.31, 154.15, 142.79, 138.04, 133.26, 131.51, 129.09, 127.07, 114.19, 106.87, 61.14, 56.25, 55.43; CIMS (isobutane) m/e 345 (MH+, 100). Anal. ($C_{19}H_{20}O_6$) C, H.

(E)-3-(3-Methoxyphenyl)-2-(3,4,5-trimethoxyphenyl)-prop-2-enoic acid (23b): 483 mg; 70%; mp 178°–180° C.; $^1$H NMR ($CDCl_3$, 200 MHz) $\delta$8.70 (bs, 1H), 7.90 (s, 1H), 7.15 (t, J=8.1 Hz, 1H), 6.85–6.76 (m, 2H), 6.62 (bs, 1H), 6.49 (s, 2H), 3.88 (s, 3H), 3.78 (s, 6H), 3.55 (s, 3H); CIMS (isobutane) m/e 345 (MH+, 100). Anal. ($C_{19}H_{20}O_6$) C, H.

(E)-2-(4-Methoxyphenyl)-3-(3,4,5-trimethoxyphenyl)-prop-2-enoic acid (23c): 468 mg; 68%; mp 206°–207° C.

Preparation of compounds 24a–b. Conc. $H_2SO_4$ (0.5 mL) was added to a stirred solution of carboxylic acid 23a–b (172 mg, 0.5 mmol) in absolute methanol (20 mL), and the mixture was heated under reflux for 6 h. About 90% of the excess methanol was removed by evaporation, and the residue was poured into ice-water (300 mL). The product was extracted with ether (2×40 mL), and the combined extracts were washed with 2% aqueous NaOH solution (2×50 mL) followed by water (200 mL). Evaporation of the ether from the dried ($Na_2SO_4$) solution gave the desired products.

(E)-Methyl 3-(4-methoxyphenyl)-2-(3,4,5-trimethoxyphenyl)-prop-2-enoate (24a): 316 mg; 88%; mp 74°–75° C.; $^1$H NMR ($CDCl_3$, 200 MHz) $\delta$7.77 (s, 1H), 7.03 (d, J=9.0 Hz, 2H), 6.72 (d, J=9.0 Hz, 2H), 6.44 (s, 2H), 3.91 (s, 3H), 3.81 (s, 3H), 3.78 (s, 6H), 3.77 (s, 3H); CIMS (isobutane) m/e 359 (MH+, 100). Anal. ($C_{20}H_{22}O_6$) C, H.

(E)-Methyl 3-(3-methoxyphenyl)-2-(3,4,5-trimethoxy-phenyl)-prop-2-enoate (24b): 308 mg; 86%; mp 87°–88° C.; $^1$H NMR ($CDCl_3$, 200 MHz) $\delta$7.79 (s, 1H), 7.13 (t, 1 J=8.1 Hz, 1H), 6.82–6.70 (m, 2H), 6.59 (bs, 1H), 6.46 (s, 2H), 3.88 (s, 3H), 3.83 (s, 3H), 3.77 (s, 6H), 3.54 (s, 3H); CIMS (isobutane) m/e 359 (MH+, 100). Anal. ($C_{20}H_{22}O_6$) C, H.

(E)-N-Methyl-[3-(4-methoxyphenyl)-2-(3,4,5-trimethoxyphenyl)]-prop-2-enoamide (24c). A mixture of carboxylic acid 23a (172 mg, 0.5 mmol) and thionyl chloride (1 mL) in benzene (10 mL) was refluxed for 6 h. The excess thionyl chloride and benzene were removed at reduced pressure and the residue was kept under vacuum for 30 min. It was subsequently mixed with aqueous methylamine solution (40%, 5 mL) and kept at room temperature for 2 h. The precipitated product was filtered, washed sequentially with 2% NaOH solution and water, and dried. An analytical sample was prepared by recrystallization from EtOAc-hexane. 156 mg; 87%; mp 172°–174° C.; $^1$H NMR ($CDCl_3$, 200 MHz) $\delta$7.79 (s, 1H), 6.99 (d, J=8.8 Hz, 2H), 6.71 (d, J=8.8 Hz, 2H), 6.46 (s, 2H), 5.10 (bq, 1H), 3.94 (s, 3H), 3.81 (s, 6H), 3.76 (s, 3H), 2.87 (d, J=4.8 Hz, 3H); CIMS (isobutane) m/e 358 (MH+, 100). Anal. ($C_{20}H_{23}O_5$) C, H.

Preparation of compounds 24d–f. A solution of ethylamine (0.5 mL) or the appropriate amino alcohol (0.5 mmol) in THF (5 mL) was added to a solution of the acid chlorides (prepared from 23a–b in 0.5 mmol scale, as described above) in THF (10 mL). The mixture was stirred for 3 h. Solvents were removed at reduced pressure, and the residue was poured onto ice (200 g). The product was extracted with ether (2×20 mL), washed with water, and dried (Na$_2$SO$_4$). Evaporation of ether gave crude products. Product 24d was purified by recrystallization from EtOAc-hexane and the liquid products 24e and 24f were purified by column chromatography on silica gel using ether as the eluent.

(E)-N-Ethyl-[3-(4-methoxyphenyl)-2-(3,4,5-trimethoxyphenyl)]-prop-2-enoamide (24d): 149 mg; 80%; mp 152°-154° C.; $^1$H NMR (CDCl$_3$, 200 MHz) δ7.77 (s, 1H), 6.99 (d, J=8.4 Hz, 2H), 6.70 (d, J=8.4 Hz, 2H), 6.46 (s, 2H), 5.58 (bt, 1H), 3.95 (s, 3H), 3.80 (s, 6H), 3.76 (s, 3H), 3.36 (q, J=7.1 Hz, 2H), 1.11 (t, J=7.1 Hz, 3H); CIMS (isobutane) m/e 372 (MH+, 100). Anal. C$_{21}$H$_{25}$NO$_5$) C, H.

(E)-(2-N,N-Diethylamino)ethyl-3-(4-methoxyphenyl)-2-(3,4,5-trimethoxyphenyl)-prop-2-enoate (24e): 192 mg; 87%; oil; $^1$H NMR (CDCl$_3$, 200 MHz) δ7.77 (s, 1H), 7.06, (d, J=8.8 Hz, 2H), 6.72 (d, J=8.8 Hz, 2H), 6.44 (s, 2H), 4.28 (t, J=6.1 Hz, 2H), 3.90 (s, 3H), 3.78 (s, 6H), 3.77 (s, 3H), 2.77 (t, J=6.1 Hz, 2H), 2.55 (q, J=7.2 Hz, 4H), 1.01 (t, J=7.2 Hz, 6H); $^{13}$C NMR (CDCl$_3$, 50 Mhz) δ168.49, 160.90, 154.06, 140.53, 137.88, 132.88, 132.16, 130.19, 127.42, 114.10, 106.89, 63.94, 61.14, 56.25, 55.41, 50.98, 47.89, 12.04; CIMS (isobutane) m/e 444 (MH+, 100). Anal. (C$_{25}$H$_{33}$NO$_6$) C, H.

(E)-(2-N,N-Diethylamino)ethyl-3-(3-methoxyphenyl)-2-(3,4,5-trimethoxyphenyl)-prop-2-enoate (24f): 201 mg; 91%; oil; $^1$H NMR (CDCl$_3$, 200 MHz) δ7.78 (s, 1H), 7.13 (d, J=7.9 Hz, 1H), 6.80–6.74 (m, 2H), 6.61–6.59 (m, 1H), 6.46 (s, 2H), 4.30 (t, J=6.1 Hz, 2H), 3.87 (s, 3H), 3.78 (s, 6H), 3.54 (s, 3H), 2.77 (t, J=6.1 Hz, 2H), 2.56 (q, J=7.1 Hz, 4H), 1.05 (t, J=7.1 Hz, 6H); CIMS (isobutane) m/e 444 (MH+, 100 ). Anal. (C$_{25}$H$_{33}$NO$_6$) C, H.

3,4,4',5-Tetramethoxybenzophenone (27). Anhydrous AlCl$_3$ (260 mg, 2 mmol) was added to a well-stirred solution of 3,4,5-trimethoxybenzoyl chloride (25) (461 mg, 2 mmol) and anisole (216 mg, 2 mmol) at 0° C. in CH$_2$Cl$_2$ (25 mL). The mixture was stirred while allowing it to warm to room temperature. After 6 h, the resultant dark reaction mixture was poured into ice cold 5% HCl (20 mL), and the CH$_2$Cl$_2$ layer was separated. The aqueous layer was extracted with an additional 30 mL of CH$_2$Cl$_2$, and the combined CH$_2$Cl$_2$ solutions were washed with saturated sodium bicarbonate solution. Evaporation of solvents from the dried CH$_2$Cl$_2$ extract and purification of the residue by chromatography on a column of silica gel, using 5% EtOAc in hexane as eluent, gave product 27 (487 mg, 80%); mp 72°-73° C.; $^1$H NMR (CDCl$_3$, 200 MHz) δ7.83 (d, J=8.7 Hz, 2H), 7.03 (s, 2H), 6.98 (d, J=8.7 Hz, 2H), 3.94 (s, 3H), 3.90 (s, 3H), 3.88 (s, 6H); CIMS (isobutane) m/e 303 (MH+, 100). Anal. (C$_{17}$H$_{18}$O$_5$), C, H.

4-Methoxyphenyl-(3,4,5-trimethoxyphenyl)methanol (28). Sodium borohydride (76 mg, 2 mmol) was added in small portions to a well-stirred solution of 3,4,4',5-tetramethoxybenzophenone (27) (302 mg, 1 mmol) in ethanol (15 mL) at 0° C. in 15 min and the resultant mixture was stirred for 3 h at room temperature. The reaction was quenched by careful addition of glacial acetic acid (1 mL), and the solvents were removed at reduced pressure. The residue was poured into water, and the product was extracted with ether (2×50 mL). The combined ether extracts were washed with saturated NaHCO$_3$ solution, followed by water, and dried (Na$_2$SO$_4$). Evaporation of solvents and crystallization of the residue from EtOAc-hexane gave product 28 as a white crystalline solid (287 mg, 94%); mp 104°-105° C.; $^1$H NMR (CDCl$_3$, 200 MHz) δ7.29 (d, J=8.7 Hz, 2H), 6.88 (d, J=8.7 Hz, 2H), 6.60 (s, 2H), 5.73 (d, J=3.2 Hz, 1H), 3.82 (s, 9H), 3.80 (s, 3H), 2.32 (d, J=3.2 Hz, 1H); CIMS (isobutane) m/e 305 (MH+, 100). Anal. (C$_{17}$H$_{20}$O$_5$) C, H.

4-Methoxyphenyl-(3,4,5-trimethoxyphenyl)methane (29). A solution of 28 (304 mg, 1 mmol) in EtOAc (20 mL) was hydrogenated at 60 psi in the presence of 10% Pd-C (60 mg) for 12 h. The solution was filtered, and solvents were evaporated. The crude product was purified by crystallization from EtOAc and hexane (183 mg, 60%); mp 66°-67° C.; $^1$H NMR (CDCl$_3$, 200 MHz) δ7.12 (d, J=8.5 Hz, 2H), 6.85 (d, J=8.5 Hz, 2H), 6.39 (s, 2H), 3.87 (s, 2H), 3.82 (s, 3H), 3.81 (s, 6H), 3.79 (s, 3H); CIMS (isobutane) m/e 289 (MH+, 100). Anal. (C$_{17}$H$_{20}$O$_4$) C, H.

2,3,4,7-Tetramethoxyphenanthrene (32). A mixture of 30a and 31a (1.1 g 3.6 mmol) was dissolved in cyclohexane (500 ml) containing iodine (60 mg) and acetophenone (0.22 ml, 0.5 eq). The solution was irradiated with a 450 W medium pressure mercury UV lamp for 6 h with stirring and cooling. TLC showed that the starting material had disappeared. The solvent was evaporated and the residue subjected to flash chromatography (ether:hexane, 30:70 by volume, silica gel 230–400 mesh) to give 32a (460 mg) and 32c (560 mg, 92.7% total yield): 32a, pale yellow oil; IR (KBr) 836 (2H adjacent), 760 cm$^{-1}$ (3H adjacent); $^1$H NMR (CDCl$_3$, 500 MHz) δ7.30-7.50 (m, 3H), 7.00–7.10 (m, 3H), 4.00 (s, br, 9H), 3.70 (s, 3H). EIMS m/e 298 (M+, 58), 283 (11); Anal. (C$_{18}$H$_{18}$O$_4$) C, H.

2,3,4,7-Tetramethoxyphenanthrene (32c). This compound was obtained as white crystals from ethyl acetate and hexane as described above: mp 142°-144° C.; IR (KBr) 866 (1H), 831 cm$^{-1}$ (2H adjacent); $^1$H NMR (CDCl$_3$, 500 MHz) δ9.41 (d, 1H), 7.60 (s, 2H), 7.23–7.21 (m, 2H), 7.08 (s, 1H). 4.03 (s, 3H), 4.01 (s, 3H), 4.00 (s, 3H), 3.96 (s, 3H); EIMS m/e 298 (M+, 100), 283 (41). Anal. (C$_{18}$H$_{18}$O$_4$): C, H.

2,3,4,6-Tetramethoxyphenanthrene (32b). Compound 23b (460 mg, 58% yield) was prepared by irradiation of a mixture of 30b and 31b (800 mg, 2.66 mmol) in hexane (500 mL) as described above: mp 68°-70° C.; IR (KBr) 865 (1H), 843 cm$^{-1}$ (2H adjacent); $^1$H NMR (CDCl$_3$, 200 MHz) δ9.06 (d, 1H, J=4 Hz), 7.75 (d, 1H, J=8 Hz), 7.60 (d, 1H, J=8.6 and 8.8 Hz), 7.47 (d, 1H, J=8 Hz 7.22 (dd 1H J=8.6 and 2.8 Hz), 7.08 (s, 1H), 4.02 (s, 6H), 4.01 (s, 3H), 4.00 (s, 3H). EIMS m/e 298 (M+, 100), 283 (45). Anal. (C$_{18}$H$_{18}$O$_4$), C, H.

2,3,4,8-Tetramethoxyphenanthrene (32d). The stilbene mixture containing 30c and 31c (1010 mg, 3.36 mmol) in cyclohexane (500 mL) containing iodine (53 mg) and acetophenone (1.71 mmol, 0.5 eq) was irradiated as in the above synthesis of 32a and 32c to give 32d (760 mg, 76%): mp 80°-82° C.; IR (KBr) 846 (2H adjacent), 790 cm$^{-1}$ (3H adjacent); $^1$H NMR (CDCl$_3$, 200 Mhz) δ9.12 (d, 1H, J=10 Hz), 8.20 (d, 1H, J=10 Hz), 7.57 (m, 2H), 7.10 (s, 1H), 6.99 (d, 1H, J=8 Hz), 4.03 (s, 6H), 4.02 (s, 3H), 4.00 (s, 3H); EIMS m/e 298 (M+, 100), 283 (40). Anal. (C$_{18}$H$_{18}$O$_4$) C, H.

2-(4-Methoxyphenyl)-3-(3,4,5-trimethoxyphenyl)propionic acid (33). A mixture of the ester 17j (3.0 g, 8.3 mmol) in ethanol (50 mL) and potassium hydroxide (4.0 g, 71 mmol) in ethanol:water (60 mL, 4:1 by volume)

was heated at reflux under Ar until most of the starting material disappeared (about 24 h). The reaction solution was poured into ice-cold water (500 mL) and acidified with 20% sulfuric acid (200 mL), extracted with ether (100, 100, 50 mL), washed with water (50 mL) and saturated sodium chloride solution (50 mL), and dried over anhydrous sodium sulfate. Evaporation of the filtrate and flash chromatography (ether: hexane, 70:30 by volume, silica gel 230–400 mesh) gave 33 as a yellow oil (1.97 g, 79.1%): IR (film) 3231 (br), 3005, 2933, 1733, 1703, 1590, 1513, 1462, 1421, 1246, 1180, 1123 cm$^{-1}$; $^1$H NMR (CDCl$_3$, 200 MHz) $\delta$7.32 (d, 2H, J=10 Hz), 6.85 (d, 2H, J=10 Hz), 6.83 (s, 2H), 3.80 (s, 3H), 3.79 (s, 3H), 3.77 (m, 1H), 3.74 (s, 6H), 3.31 (m, 1H), 2.95 (m, 1H). FABMS m/e 347 (MH$^+$, 39.2).

2-(4-Methoxyphenyl)-4,5,6-trimethoxyindan-3-one (34). A solution of the acid 33 (0.5 g, 1.4 mmol) in phosphorous oxychloride (5 mL, 53.4 mmol) was heated at reflux for 3 min. The dark red solution was poured onto crushed ice (about 30 g) and extracted with ether (50, 20, and 20 mL). The combined ether layer was dried over anhydrous sodium sulfate. Evaporation of the filtrate gave a gray solid. Recrystallization of this gray solid from ethyl acetate and hexane afforded pale gray crystals 0.32 g (69.6%): mp 104°–106° C.; IR (KBr) 3010, 2960, 1697, 1595, 1512, 1323, 1251, 1139 cm$^{-1}$; $^1$H NMR (CDCl$_3$, 200 MHz) $\delta$7.11 (d, 2H, J=8 Hz), 6.85 (d, 2H, J=8 Hz), 6.71 (s, 1H), 4.03 (s, 3H), 3.96 (s, 3H), 3.87 (s, 3H), 3.78 (s, 3H), 3.78 (m, 1H), 3.54 (m, 1 H), 3.10 (m, 1H); EIMS m/e 328 (M$^+$, 98). Anal. (C$_{19}$H$_{20}$O$_5$), C, H.

2-(4-Methoxyphenyl)-4,5,6-trimethoxyindane (35). A mixture of the ketone 34 (250 mg, 0.74 mmol) and 10% Pd-C (100 mg) in acetic acid (40 mL) was subjected to hydrogenolysis at 42 psi hydrogen pressure until the absorption of hydrogen ceased. Filtration and evaporation of the reaction solution gave an oil. It was purified by flash chromatography (ether:hexane, 70:30 by volume, silica gel 230–400 mesh) to afford 35 as a colorless oil(230 mg, 96.2%). TLC only showed one spot. $^1$H NMR (CDCl$_3$, 500 MHz) $\delta$7.22 (d, 2H, J=8 Hz), 6.72 (d, 2H, J=8 Hz), 6.59 (s, 1H), 3.90 (s, 3H), 3.88 (s, 3H), 3.84 (s, 3H), 3.80 (s, 3H), 3.63 (m, 1H), 3.36 (m, 1H), 3.26 (m, 1H), 2.97 (m, 2H). EIMS m/e 314 (M$^+$, 100). Anal. (C$_{19}$H$_{22}$O$_4$) C, H.

1-(4'-Methoxybenzyl)-5,6,7-trimethoxyisoquinoline Methiodide (Takatonine Iodide 37). A solution of 36 (200 mg, 0.59 mmol) in anhydrous decahydronaphthalene (5 mL) containing palladium black (20 mg) was heated at reflux for 2 h under Ar. The reaction mixture was filtered through a celite pad, and the celite pad was rinsed with CHCl$_3$ (10 mL). After the CHCl$_3$ was evaporated, the residue was dissolved in ether (10 mL), and MeI (0.5 mL) was added. The resulting solution was kept at room temperature overnight. The yellow crystalline precipitate was filtered and washed with ether (5 mL) to give takatonine iodide (37) as yellow plates (174.1 mg, 61.3%): m.p. 180°–182° C.; $^1$H NMR (CDCl$_3$, 200 MHz) $\delta$8.72 (d, br, 1H, J=6 Hz), 8.32 (d, 1H, J=6 Hz), 7.40 (s, 1H), 7.01 (d, 2H, J=8 Hz), 6.84 (d, 2H, J=8 Hz), 5.11 (s, 2H), 4.61 (s, 3H), 4.14 (s, 3H), 4.10 (s, 3H), 4.01 (s, 3H), 3.77 (s, 3H). The $^1$H NMR spectrum of 6 was identical with the reported $^1$H NMR spectrum of takatonine iodide.

1-(4'-Methoxybenzyl)-5,6,7-trimethoxy-1,2,3,4-tetrahydroisoquinoline (38). Sodium borohydride (460 mg, 12.9 mmol) was added portionwise over a period of 30 min to a solution of 36 (460 mg, 1.36 mmol) in methanol (5 mL) and the reaction solution was stirred at room temperature for 1 h. The reaction solution was evaporated under reduced pressure to dryness. The residue was dissolved in water (5 mL) and basified with ammonium hydroxide solution, then extracted with ether (30, 20, and 10 mL). The combined ether layer was dried over anhydrous sodium sulfate. Evaporation of the filtrate and flash chromatography (ether, silica gel 230–400 mesh) gave compound 38 as an oil (450 mg, 96.0%): $^1$H NMR (CDCl$_3$, 200 MHz) $\delta$7.18 (d, 2H, J=8 Hz), 6.87 (d, 2H, J=8 Hz), 6.49 (s, 1H), 4.06 (m, 1H), 3.86 (s, 3H), 3.85 (s, 3H), 3.81 (s, 3H), 3.80 (s, 1H), 3.16 (m, 2H), 2.87 (m, 2H), 2.68 (t, 2H, J=6 Hz), 1.84 (s, br, 1H); FABMS m/e 344 (MH$^+$, 41).

1-(4'-Methoxybenzoyl)-5,6,7-trimethoxyisoquinoline (39). A solution of 36 (250 mg, 0.73 mmol) and DDQ (188 mg, 0.81 mmol) in anhydrous THF (2 mL) was heated at reflux overnight. Preparative TLC purification (ether, precoated silica gel plate, 1000 microns) gave 39 as an oil (125 mg, 48.4%): IR (neat) 2924, 2851, 1659, 1560, 1475, 1260, 1159, 1122 cm$^{-1}$; $^1$H NMR (CDCl$_3$, 200 MHz) $\delta$8.48 (d, 1H, J=6 Hz), 7.98 (d, 1H, J=6 Hz), 7.95 (d, 2H, J=8 Hz), 7.37 (s, 1H), 6.96 (d, 2H, J=8 Hz), 4.08 (s, 3H), 4.03 (s, 3H), 3.93 (s, 3H), 3.88 (s, 3H); CIMS (isobutane) m/e, 354 (MH$^+$, 100).

1-(4'-Methoxybenzoyl)-5,6,7-trimethoxyisoquinoline Methiodide (40). A solution of 39 (70 mg, 0.2 mmol) in anhydrous benzene (2 mL) and iodomethane (0.6 mL) was heated at reflux for 24 h under Ar. The reaction mixture was evaporated to dryness and the residue was partitioned between distilled water (10 mL) and CHCl$_3$ (10 mL). The CHCl$_3$ was extracted with H$_2$O (2×5 mL), and the combined aqueous extracts were washed with ether (5 mL). Evaporation of the distilled water solution gave a yellow solid 40 (60 mg, 60.6%): $^1$H NMR (CDCl$_3$, 200 MHz) $\delta$8.95 (d, 1H, J=6 Hz), 8.52 (d, 1H, J=6 Hz), 8.11 (d, br, 2H, J=8 Hz), 7.10 (d, 2H, J=8 Hz), 6.73 (s, 1H), 4.53 (s, 3H), 4.15 (s, 3H), 4.14 (s, 3H), 3.92 (s, 3H), 3.80 (s, 3H); FABMS calcd. for C$_{21}$H$_{22}$INO: 368.1498 (cation). Found: 368.1489.

1-(4'-Methoxybenzyl)-5,6,7-trimethoxy-2-methyl-1,2,3,4-tetrahydroisoquinoline (Tetrahydrotakatonine, 41). A solution of 38 (400 mg, 1.2 mmol) in formic acetic anhydride (80 mL) was stirred at room temperature overnight. A clear yellow solution was obtained. The solvent was evaporated to dryness. To this residue water (5 mL) was added, and the aqueous solution was extracted with CH$_2$Cl$_2$ (20, 10, and 10 mL). The CH$_2$Cl$_2$ layer was washed successively with 10% NaOH solution (5 mL), water (5 mL), saturated aqueous NaCl (5 mL), and dried over anhydrous sodium sulfate. Evaporation of the filtrate gave an oil (590 mg). A solution of this oil (450 mg) in anhydrous toluene (10 mL) containing POCl$_3$ (2 mL) was heated at reflux for 3 h under Ar. TLC showed that starting material was consumed. After evaporation of the solvent, the resulting brown residue was dissolved in methanol (30 mL). NaBH$_4$ (1.6 g) was added over 0.5 h, and the reaction solution was stirred at room temperature for 2 h. Evaporation of the solvent gave a residue which was extracted with CH$_2$Cl$_2$ (20, 10, and 10 mL). The organic layer was washed successively with water (10 mL) and saturated aqueous NaCl (10 mL) and dried over anhydrous sodium sulfate. Evaporation of the filtrate and flash chromatography (CHCl$_3$, then CHCl$_3$:EtOH, 96:4 by volume, silica gel 230–400 mesh) gave 41 as an oil (225 mg, 52.5%): $^1$H NMR (CDCl$_3$, 200 MHz) $\delta$7.02 (d, 2H, J=8 Hz), 6.80 (d, 2H, J=8 Hz), 5.87 (s, 1H), 3.84 (s, 3H), 3.83 (s, 3H), 3.78 (s, 3H), 3.67 (t, 1H, J=6 Hz), 3.55 (s, 3H), 3.13 (m, 2H), 2.75 (m, 4H), 2.51 (s, 3H); FABMS m/e 358 (MH+, 100). The ¹H NMR spectrum of 41 was consistent with the previously presented ¹H NMR of tetrahydrotakatonine.

N-(2,3,4-trimethoxyphenethyl)acetamide (43). Acetyl chloride (1.3 mL, 1.45 g, 18.2 mmol) was added dropwise to a stirred suspension of compound 42 (3 g, 12.1 mmol) in 2.0N NaOH solution (27 mL, 54.0 mmol) cooled in an ice bath. The resulting solution was stirred at 0° C. for 1 h. The reaction solution was extracted with CHCl₃ (50, 30, and 20 mL) and the combined CHCl₃ layer was washed with saturated NaCl solution and dried over anhydrous Na₂SO₄. Evaporation of the filtrate gave a pale yellow oil that was subjected to flash chromatography (ether, silica gel 230–400 mesh) to give compound 43 as an oil (2.75 g, 89.9%): ¹H NMR (CDCl₃, 200 MHz) δ6.83 (d, 1H, J=8 Hz), 6.62 (d, 1H, J=8 Hz), 5.84 (s, br, 1H), 3.90 (s, 3H), 3.87 (s, 3 H), 3.85 (s, 3H), 3.44 (q, 2H, J=6 Hz), 2.76 (t, 2H, J=6 Hz), 1.93 (s, 3H); EIMS m/e 253 (M+, 72).

1-Methyl-5,6,7-trimethoxy-3,4-dihydroisoquinoline (44). A solution of the acetamide 43 (280 mg, 1.1 mmol) in toluene (5 mL) containing POCl₃ (0.8 mL, 8.5 mmol) was heated at reflux under Ar for 2 h. The excess POCl₃ and the solvent were evaporated under vacuum. The black residue was washed with petroleum ether (10 mL). The residue was dissolved in distilled water (10 mL) and made basic by 5% NH₄OH aq (10 mL). The aqueous solution was extracted with CHCl₃ (20, 10, and 5 mL). The combined CHCl₃ layer was washed successively with water (10 mL) and saturated NaCl solution (10 mL) and dried over anhydrous Na₂SO₄. Evaporation of the filtrate and chromatography (ether:ethanol, 98:2 by volume, silica gel 230–400 mesh) gave compound 44 as a pale brown oil (230 mg, 89.2%): ¹H NMR (CDCl₃, 200 MHz) δ6.84 (s, 1H), 3.92 (s, 3H), 3.89 (s, 3H), 3.85 (s, 3H), 3.61 (t, 2H, J=8 Hz), 2.64 (t, 2H, J=8 Hz), 2.36 (s, 3H). EIMS m/e 235 (M+, 84).

2,5-Dimethoxybenzoyl Chloride (45). A mixture of 2,5-dimethoxybenzoic acid (25 g, 137.2 mmol) and thionyl chloride (35 mL, 470.6 mmol) was heated at reflux under Ar for 4 h. The reaction solution was evaporated to dryness and the residue was purified by high vacuum distillation at 127° C./2 mm Hg to give compound 45 as a pale yellow oil (26.5 g, 96.7%). When standing at room temperature, this oil changed to yellow crystals, m.p. 36°–38° C.

2-(2',5'-Dimethoxybenzoyl)-1-methylene-5,6,7-trimethoxy-1,2,3,4-tetrahydroisoquinoline (46). A solution of compound 45 (746 mg, 3.7 mmol) in anhydrous benzene (2 mL) was slowly added at room temperature to a solution of compound 44 (880 mg, 3.7 mmol) in anhydrous benzene (10 mL) containing triethylamine (568 mg, 5.6 mmol, 0.78 mL). The resulting solution was heated at reflux with stirring under Ar for 2 h. White NH₄Cl precipitated and was removed by filtration. The filtrate was evaporated to dryness and the residue was subjected to flash chromatography (ether:triethylamine, 99:1 by volume, silica gel 230–300 mesh) to give compound 46 as an oil (1.3 g, 87.8%): ¹H NMR (CDCl₃, 200 MHz) δ6.87 (s, 1H), 6.85 (d, 1H, J=10 Hz), 6.80 (d, 1H, J=3 Hz), 6.70 (d, 1H, J=10 Hz), 5.21 (s, br 1H), 4.55 (s, br, 1H), 3.90 (s, 6H), 3.88 (s, 3H), 3.84 (s, 3H), 3.75 (s, 3H), 3.41 (s, br, 2H), 2.88 (t, 2H, J=6 Hz). CIMS (isobutane) m/e 400 (MH+, 100).

5-Hydro-8-oxo-2,3,4,10-tetramethoxy-6H-dibenzo-(a,g)quinolizine (47). A solution of compound 46 (1.59 g, 4.0 mmol) in methanol (500 mL) containing triethylamine (0.5 mL) was irradiated with 450-W medium pressure mercury lamp at room temperature for about 2 h with stirring. Evaporation of the solvent gave a yellow syrup that was subjected to flash chromatography (ether, silica gel 230–400 mesh) to give a yellow solid. Recrystallization of the solid from methanol gave compound 47 as yellow needles (350 mg, 23.8%): m.p. 196°–198° C.; ¹H NMR (CDCl₃, 200 MHz) δ7.84 (d, 1H, J=4 Hz), 7.51 (d, 1H, J=8 Hz), 7.26 (d,d, 1H, J=8 and 4 Hz), 7.09 (s, 1H), 6.89 (s, 1H), 4.34 (t, 2H, J=6 Hz), 3.97 (s, 3H), 3.94 (s, 6H), 3.91 (s, 3H), 2.96 (t, 2H, J=6 Hz). CIMS (isobutane) m/e 368 (MH+, 100). Anal. (C₂₁H₂₁O₅): C, H.

5,8,13,13a-Tetrahedro-2,3,4,10-tetramethoxy-6H-dibenzo-(a,g)quinolizine (48). A suspension of LiAlH₄ (1.4 mL, 1.4 mmol, 5 eq, 1.0M in THF) was added dropwise to a solution of compound 47 (100 mg, 0.27 mmol) in anhydrous THF (15 mL) with stirring at room temperature under At. The reaction mixture was stirred under reflux for 2 h. A yellow solution developed. The excess LiAlH₄ was decomposed by adding water until no hydrogen bubbles appeared. The residue was extracted with ether:THF (7:3 by volume, 30, 20 mL). The combined organic layer was filtered through a glass wool pad, and the filtrate was evaporated to dryness. The residue was dissolved in fresh methanol (10 mL), and NaBH₄ (125 mg, 3.28 mmol) was added in several portions. The reaction solution was stirred at reflux under Ar for 1.5 h. The reaction was evaporated to dryness under vacuum. The residue was dissolved in 10% HCl (5 mL), neutralized with solid K₂CO₃ to pH 8, extracted with CHCl₃ (20, 10, 10 mL), and dried over anhydrous Na₂SO₄. Evaporation of the filtrate obtained after removal of the Na₂SO₄ gave a pale yellow oil. Preparative silica gel TLC (ether, silica gel precoated plate, 1000 microns) purification gave compound 48 (92 mg, 95.1%). Recrystallization of compound 48 from methanol gave pale yellow needles (22.0 mg), m.p. 104°–106° C.: ¹H NMR (CDCl₃, 200 MHz) δ7.07 (d, 1H, J=8 Hz), 6.75 (dd, 1H, J=8 and 2 Hz), 6.62 (d, 1H, J=2 Hz), 6.57 (s, 1H), 3.88 (s, 6H), 3.87 (s, 3H), 3.79 (s, 3H), 3.79 (m, 3H), 3.21 (m, 2H), 2.85 (m, 3H), 2.52 (m, 1H). FABMS (Glycerol) m/e 356 (MH+, 47). Anal. (C₂₁H₂₅NO₄): C, H.

The above preferred embodiments and examples are given to illustrate the scope and spirit of the present invention. These embodiments and examples will make apparent to those skilled in the art other embodiments and examples. These other embodiments are also examples within the contemplation of the present invention. Therefore, the present invention should be limited only by the appended claims.

What is claimed is:

1. A compound of the formula:

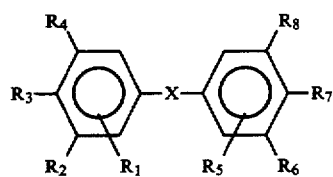

and pharmaceutically acceptable salts thereof wherein X is a cis ethylene radical of the formula:

$Y_1$ and $Z_1$ are both hydrogen; $R_1$, $R_5$, $R_6$ and $R_8$ are independently H, halo, amino, lower alkylamino, diloweralkylamino, mercapto, lower alkylthio, amino lower alkyl, lower alkanoyl, nitro, $CF_3$, amino lower alkoxy, lower alkylamino lower alkoxy, diloweralkylamino lower alkoxy, $R_2$, $R_3$ and $R_4$ are lower alkoxy;

$R_7$ is lower alkoxy, amino, lower alkylamino, alkyl of 1-3 carbon atoms, diloweralkylamino, mercapto, lower alkylthio, amino lower alkyl, lower alkanoyl, nitro, $CF_3$, amino lower alkoxy, lower alkylamino lower alkoxy, and diloweralkylamino lower alkoxy.

2. The compound according to claim 1 wherein lower alkoxy is methoxy.

3. The compound according to claim 1 wherein $R_5$ is hydrogen or halo.

4. The compound according to claim 1 wherein $R_1$, $R_6$ and $R_8$ are hydrogen.

5. The compound according to claim 1 wherein $R_1$, $R_6$, $R_8$ are hydrogen and $R_5$ is hydrogen or halo.

6. The compound according to claim 1 wherein $R_7$ is lower alkoxy, lower alkyl, thio lower alkyl, mercapto, diloweralkylamino, amino or monoloweralkylamino.

7. The compound according to claim 1 wherein $R_5$ is halo or hydrogen, $R_7$ is lower alkoxy, lower alkyl, thio lower alkyl, mercapto, diloweralkylamino, amino, or monoloweralkylamino.

8. The compound according to claim 1 wherein $R_7$ is methoxy, ethoxy, propoxy, nitro, dimethylamino, methyl, isopropyl or t-butyl.

9. The compound according to claim 1 wherein $R_5$ is Cl or hydrogen and $R_7$ is methoxy, ethoxy, propoxy, nitro, dimethylamino, methyl, isopropyl or t-butyl.

10. The compound according to claim 1 having the formula:

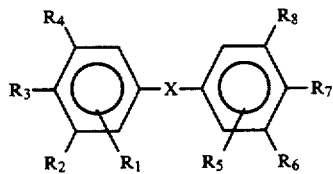

or pharmaceutically acceptable salts thereof wherein $R_2$, $R_3$ and $R_4$ are alkoxy containing 1-3 carbon atoms;

X is a cis ethylene radical of the formula:

$Y_1$ and $Z_1$ are both hydrogen;

$R_1$, $R_6$ and $R_8$ are hydrogen;

$R_7$ is alkoxy containing 1-3 carbon atoms; amino, alkylamino containing 1-3 carbon atoms, dialkylamino containing 1-3 carbon atoms; alkylthio containing 1-3 carbon atoms or mercapto and $R_5$ is hydrogen or halo.

11. The compound according to claim 10 wherein $R_5$ is hydrogen and $R_7$ is alkoxy, amino, alkylamino, or dialkylamino.

12. The compound according to claim 10 wherein $R_7$ is methoxy, amino, methylamino or dimethylamino.

13. The compound according to claim 11 wherein $R_7$ is methoxy, amino, methylamino, or dimethylamino.

14. The compound according to claim 1 wherein the compound is (Z)-1-(4-methoxyphenyl)-2-(3,4,5-trimethoxyphenyl)ethene.

15. The compound according to claim 1 wherein the compound is (Z)-1-(4-methoxy-2-chlorophenyl)-2-(3,4,5-trimethoxyphenyl)ethene, (Z)-1-(4-N,N-dimethylaminophenyl)-2-(3,4,5-trimethoxyphenyl)ethene, (Z)-1-(4-propoxyphenyl)-2-(3,4,5-trimethoxyphenyl)ethene; or (Z)-1-(4-thiomethylphenyl)-2-(3,4,5-trimethoxyphenyl)ethene.

16. The compound according to claim 1 wherein the compound is (Z)-1-(4-ethylphenyl)-2-(3,4,5-trimethoxyphenyl-ethene), (Z)-1-(4-methylphenyl)-2-(3,4,5-trimethoxyphenyl)ethene, or (Z)-1-(4-isopropylphenyl)-2-(3,4,5-trimethoxy-phenyl)ethene.

17. (E)-1-(4-N,N-dimethylamino)-2-(3,4,5-trimethoxyphenyl)ethene.

18. A pharmaceutical composition comprising a pharmaceutically effective amount of a compound of the formula:

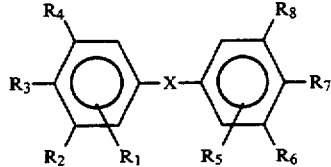

and pharmaceutically acceptable salts thereof wherein X is a cis ethylene radical of the formula:

$Y_1$ and $Z_1$ are both hydrogen; $R_1$, $R_5$, $R_6$ and $R_8$ are independently H, halo, amino, lower alkylamino, diloweralkylamino, mercapto, lower alkylthio, amino lower alkyl, lower alkanoyl, nitro, $CF_3$, amino lower alkoxy, lower alkylamino lower alkoxy, diloweralkylamino lower alkoxy, $R_2$, $R_3$ and $R_4$ are lower alkoxy;

$R_7$ is lower alkoxy, amino, lower alkylamino, alkyl of 1-3 carbon atoms, diloweralkylamino, mercapto, lower alkylthio, amino lower alkyl, lower alkanoyl, nitro, $CF_3$, amino lower alkoxy, lower alkylamino lower alkoxy, and diloweralkylamino lower alkoxy; and a pharmaceutical carrier therefor.

19. The pharmaceutical composition according to claim 18 wherein lower alkoxy is methoxy.

20. The pharmaceutical composition according to claim 18 wherein $R_5$ is hydrogen or halo.

21. The pharmaceutical composition according to claim 18 wherein $R_1$, $R_6$ and $R_8$ are hydrogen.

22. The pharmaceutical composition according to claim 18 wherein $R_1$, $R_6$, $R_8$ are hydrogen and $R_5$ is hydrogen or halo.

23. The pharmaceutical composition according to claim 18 wherein $R_7$ is lower alkoxy, lower alkyl, thio lower alkyl, mercapto, diloweralkylamino, amino or monoloweralkylamino.

24. The pharmaceutical composition according to claim 18 wherein $R_5$ is halo or hydrogen, $R_7$ is lower alkoxy, lower alkyl, thio lower alkyl, mercapto, diloweralkylamino, amino, or monoloweralkylamino.

25. The pharmaceutical composition according to claim 18 wherein $R_7$ is methoxy, ethoxy, propoxy, nitro, dimethylamino, methyl, isopropyl or t-butyl.

26. The pharmaceutical composition according to claim 18 wherein $R_5$ is Cl or hydrogen and $R_7$ is methoxy, ethoxy, propoxy, nitro, dimethylamino, methyl isopropyl or t-butyl.

27. The pharmaceutical composition according to claim 18 having the formula:

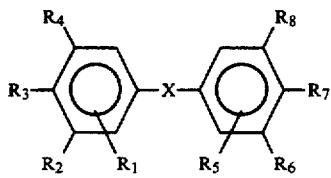

or pharmaceutically acceptable salts thereof wherein $R_2$, $R_3$ and $R_4$ are alkoxy containing 1-3 carbon atoms;

X is a cis ethylene radical of the formula:

$Y_1$ and $Z_1$ are both hydrogen;

$R_1$, $R_6$ and $R_8$ are hydrogen;

$R_7$ is alkoxy containing 1-3 carbon atoms; amino, alkylamino containing 1-3 carbon atoms, dialkylamino containing 1-3 carbon atoms; alkylthio containing 1-3 carbon atoms or mercapto and $R_5$ is hydrogen or halo; and a pharmaceutical carrier therefor.

28. The pharmaceutical composition according to claim 27 wherein $R_5$ is hydrogen and $R_7$ is alkoxy, amino, alkylamino, or dialkylamino.

29. The pharmaceutical composition according to claim 27 wherein $R_7$ is methoxy, amino, methylamino or dimethylamino.

30. The pharmaceutical composition according to claim 27 wherein $R_7$ is methoxy, amino, methylamino, or dimethylamino.

31. The pharmaceutical composition according to claim 18 wherein the compound is (Z)-1-(4-methoxyphenyl)-2-(3,4,5-trimethoxyphenyl)ethene.

32. The pharmaceutical composition according to claim 18 wherein the compound is (Z)-1-(4-methoxy-2-chlorophenyl)-2-(3,4,5-trimethoxyphenyl)ethene, (Z)-1-(4-N,N-dimethylaminophenyl)-2-(3,4,5-trimethoxyphenyl)ethene, (Z)-1-(4-propoxyphenyl)-2-(3,4,5-trimethoxyphenyl)ethene; or (Z)-1-(4-thiomethylphenyl)-2-(3,4,5-trimethoxyphenyl)ethene.

33. The pharmaceutical composition according to claim 18 wherein the compound is (Z)-1-(4-ethylphenyl)-2-(3,4,5-trimethoxyphenyl ethene), (Z)-1-(4-methylphenyl)-2-(3,4,5-trimethoxyphenyl)ethene or (Z)-1-(4-isopropylphenyl)-2-(3,4,5-trimethoxyphenyl)ethene.

34. A pharmaceutical composition comprising a pharmaceutically effective amount of a (E)-1-(4-N,N-dimethylamino)-2-(3,4,5-trimethoxyphenyl)ethene and a pharmaceutical carrier therefor.

* * * * *